(12) United States Patent
Bell et al.

(10) Patent No.: US 8,987,200 B2
(45) Date of Patent: Mar. 24, 2015

(54) POLYCATIONIC CALCIUM MODULATOR PEPTIDES FOR THE TREATMENT OF HYPERPARATHYROIDISM AND HYPERCALCEMIC DISORDERS

(75) Inventors: Gregory Bell, Tiburon, CA (US); Sarah Walter, Redwood City, CA (US); Felix Karim, Walnut Creek, CA (US)

(73) Assignee: KAI Pharmaceuticals, Inc., South San Francisco, CA (US)

( * ) Notice: Subject to any disclaimer, the term of this patent is extended or adjusted under 35 U.S.C. 154(b) by 767 days.

(21) Appl. No.: 11/941,857

(22) Filed: Nov. 16, 2007

(65) Prior Publication Data

US 2009/0023652 A1     Jan. 22, 2009

Related U.S. Application Data

(60) Provisional application No. 60/859,597, filed on Nov. 16, 2006.

(51) Int. Cl.
*A61K 38/29*     (2006.01)
*C07K 14/635*    (2006.01)
*A61K 38/17*     (2006.01)

(52) U.S. Cl.
CPC ....................................... *A61K 38/17* (2013.01)
USPC ........................................................... 514/11.8

(58) Field of Classification Search
CPC ..................................................... A61K 38/17
See application file for complete search history.

(56) References Cited

U.S. PATENT DOCUMENTS

| | | | |
|---|---|---|---|
| 5,246,925 A | 9/1993 | Deluca et al. | |
| 5,587,497 A | 12/1996 | Deluca et al. | |
| 5,602,116 A | 2/1997 | Knutson et al. | |
| 5,688,489 A | 11/1997 | Peers et al. | |
| 5,837,218 A * | 11/1998 | Peers et al. | 424/1.69 |
| 5,861,386 A | 1/1999 | Knutson et al. | |
| 5,869,473 A | 2/1999 | Knutson et al. | |
| 6,031,003 A | 2/2000 | Nemeth et al. | |
| 6,051,567 A | 4/2000 | Abrahamson et al. | |
| 6,165,977 A | 12/2000 | Mochly-Rosen | |
| 6,265,392 B1 | 7/2001 | Abrahamson et al. | |
| 6,274,169 B1 | 8/2001 | Abrahamson et al. | |
| 6,290,665 B1 | 9/2001 | Utterberg | |
| 6,855,693 B2 | 2/2005 | Mochly-Rosen et al. | |
| 6,903,083 B2 | 6/2005 | Knutson et al. | |
| 7,081,444 B2 | 7/2006 | Mochly-Rosen | |
| 7,265,092 B2 | 9/2007 | Li | |
| 2003/0036627 A1 | 2/2003 | Monteiaro et al. | |
| 2004/0018976 A1 | 1/2004 | Feder et al. | |
| 2005/0187156 A1* | 8/2005 | Mochly-Rosen | 514/12 |
| 2006/0153867 A1* | 7/2006 | Li | 424/188.1 |
| 2007/0066514 A1 | 3/2007 | Haberberger et al. | |
| 2008/0249016 A1 | 10/2008 | Henriksen et al. | |
| 2009/0023652 A1 | 1/2009 | Bell et al. | |
| 2011/0028394 A1 | 2/2011 | Karim et al. | |

FOREIGN PATENT DOCUMENTS

| | | |
|---|---|---|
| CA | 2145214 A1 | 8/1996 |
| JP | 2000336099 | 12/2000 |
| WO | WO 92/08476 A1 | 5/1992 |
| WO | WO 95/06056 A1 | 3/1995 |
| WO | WO 99/47173 A2 | 9/1999 |
| WO | WO 02/062396 A2 | 8/2002 |
| WO | WO 02/070547 A1 | 9/2002 |
| WO | WO 03/082923 A1 | 10/2003 |
| WO | WO 2004/093821 A2 | 11/2004 |
| WO | WO 2005/049647 A2 | 6/2005 |
| WO | WO 2005/059124 A2 | 6/2005 |
| WO | WO 2005/072340 A2 | 8/2005 |
| WO | WO 2007035782 * | 3/2007 |
| WO | WO 2007/038172 A2 | 4/2007 |
| WO | WO 2008/067199 A2 | 6/2008 |
| WO | WO 2008/089491 A2 | 7/2008 |
| WO | WO 2009/046220 A2 | 4/2009 |
| WO | WO 2009/075773 A2 | 6/2009 |
| WO | WO 2011/014707 A2 | 2/2011 |

OTHER PUBLICATIONS

Block et al., N. Engl. J. Med. (2004) 350(15):1516-1525.
Brown et al., J. Bone Miner. Res. (1991) 6:1217-1225.
Csukai et al., J. Biol. Chem. (1997) 272:29200-29206.
Nagano and Nemeth, J. Pharmacol. Sci. (2005) 97:355-360.
Nemeth et al., PNAS USA (1998) 95:4040-4045.
Daria Mochly-Rosen, List of peptides provided for experimental use sent to Dr. Nicholas Webster, University of California, San Diego, San Diego, California, U.S., Feb. 25, 1996.
Daria Mochly-Rosen, List of peptides provided for experimental use sent to Dr. James A. Fagin, University of Cincinnati, Cincinnati, Ohio, U.S., Apr. 3, 1996.
John A. Johnson, List of peptides provided for experimental use sent to Drs. William Karnes and/or Shaun Weller, Mayo Foundation, SW Rochester, Minnesota, U.S. Dec. 16, 1996.
List of peptides provided for experimental use sent to Dr. Lobby on Feb. 25, 1997.
Che-Hong Chen, List of peptides provided for experimental use and related correspondence sent to and from Dr. Kevin Claffey, Beth Israel Deaconess Medical Center, Boston, Massachusetts, U.S., Jun. 2, 1997.
Che-Hong Chen, List of peptides provided for experimental use sent to Dr. Piero Biancani, East Greenwich, Rhode Island, U.S., Jun. 2, 1997.

(Continued)

*Primary Examiner* — Thomas S Heard
(74) *Attorney, Agent, or Firm* — McDermott Will Emery LLP

(57) ABSTRACT

The present invention provides methods and kits for treating hyperparathyroidism, bone disease and/or hypercalcemic disorders. In particular, methods for lowering serum PTH and serum calcium using polycationic calcium modulator peptides are provided. The calcium modulator peptides can be used to treat subjects having, for example: primary, secondary or tertiary hyperparathyroidism; hypercalcemia of malignancy; metastatic bone disease; or osteoporosis.

4 Claims, 15 Drawing Sheets

(56) References Cited

OTHER PUBLICATIONS

Kevin P. Clafferty, Letter discussing peptides and related search results sent to Dr. Dania Mochly-Rosen, Stanford University School of Medicine, Stanford, California, U.S., Apr. 15, 1997.

Che-Hong Chen, List of peptides provided for experimental use and related journal article (Miyagawa et al.) sent to Dr. R. Kent Hermsmeyer, Oregon Regional Primate Research Center, Beaverton, Oregon, U.S., Jan. 5, 1998.

List of peptides provided for experimental use sent to Dr. Lobo, University of California, San Francisco, San Francisco, California, U.S., Feb. 11, 1998.

Che-Hong Chen, List of peptides provided for experimental use and related correspondence sent to and from Dr. Jeffery Knauf, University of Cincinnati, Cincinnati, Ohio, U.S., Jul. 13, 1999.

Kevin P. Claffey, e-mail correspondence regarding peptides sent to Dr. Che-Hong Chen, Jun. 2, 1997.

Che-Hong Chen, List of peptides provided for experimental use sent to Dr. Richard A. Clark, State University of New York, Stony Brook, Stony Brook, New York, U.S., Jun. 2, 1997.

Richard A. Clark, e-mail correspondence regarding peptides sent to and from Dr. Daria Mochly-Rosen, Jun. 2, 1997.

Che-Hong Chen, List of peptides provided for experimental use and related correspondence sent to and from Dr. Susie Mihailidou, Royal North Shore Hospital, St. Leonards, Australia, Jul. 13, 1998.

Che-Hong Chen, List of peptides provided for experimental use sent to Dr. Mohamed Boutjdir, VA Medical Center, Brooklyn, New York, U.S., Aug. 14, 1998.

Che-Hong Chen, List of peptides provided for experimental use sent to Dr. John D. Levine, University of California, San Francisco, San Francisco, California, U.S., Mar. 10, 1999.

Daria Mochly-Rosen, Material Transfer Agreement and List of peptides provided for experimental use sent to Dr. Jon D. Levine, University of California, San Francisco, San Francisco, California, U.S., Feb. 25, 1999.

Che-Hong Chen, List of peptides provided for experimental use sent to Dr. Derek Miles Yellon, Hatter Institute for Cardiovascular Studies, University of College Hospital and Medical School, London, England, United Kingdom, Jun. 25, 1998.

Che-Hong Chen, List of peptides provided for experimental use sent to Dr. Adrienne Gordon, University of California, San Francisco, San Francisco, California, U.S., Sep. 10, 1998.

Che-Hong Chen, List of peptides provided for experimental use and related correspondence sent to and from Dr. Derek Miles Yellon, Hatter Institute for Cardiovascular Studies, University of College Hospital and Medical School, London, England, United Kingdom, Oct. 14, 1998.

Che-Hong Chen, List of peptides provided for experimental use and related correspondence regarding peptides project outline sent to and from Dr. Fiorenzo Battaini, University of Milano, Milano, Italy, Oct. 15, 1998.

Che-Hong Chen, List of peptides provided for experimental use and related correpondence sent to and from Dr. Yasuki Kihara, Kyoto University, Kyoto, Japan, Oct. 15, 1998.

Che-Hong Chen, List of peptides provided for experimental use and related correspondence sent to and from Dr. Naoaki Saito, Kobe University, Kobe, Japan, Oct. 15, 1998.

Daria Mochly-Rosen, Material Transfer Agreement, List of peptides provided for experimental use, and related correspondence sent to and from Dr. Mita Das, University of Colorado Health Sciences Center, Denver, Colorado, U.S., Jan. 11, 1999.

Che-Hong Chen, List of peptides provided for experimental use and related correspondence sent to and from Dr. Rafael Nesher, Hebrew University-Hadassah Medical Center, Jerusalem, Israel, Feb. 10, 1999.

Daria Mochly-Rosen, Material Transfer Agreement, List of peptides provided for experimental use, and related correspondence sent to and from Dr. Steven Pelech, University of British Columbia, British Columbia, Canada, Feb. 10, 1999.

Che-Hong Chen, List of peptides provided for experimental use and related correspondence sent to and from Dr. Naoaki Saito, Kobe University, Kobe, Japan, Feb. 10, 1999.

List of peptides provided for experimental use sent to Dr. Imogen Coe, York University, Ontario, Canada, Apr. 8, 1999.

Che-Hong Chen, List of peptides provided for experimental use and related correspondence sent to and from Dr. Mireia Gomez-Angelats, Research Triangle Park, North Carolina, U.S., Jul. 13, 1999.

Daria Mochly-Rosen, Material Transfer Agreement, List of peptides provided for experimental use, and related correspondence sent to and from Dr. Jau-Shyong Hong, NIEHS, NIH, Research Triangle Park, North Carolina, U.S., Jul. 13, 1999.

Che-Hong Chen, List of peptides provided for experimental use and related correspondence sent to Dr. Anne-Marie Schmitt-Verhulst, Centre d'Immunologie INSERM-CNRS de Marseille-Luminy, Marseilles, France, Jul. 14, 1999.

Daria Mochly-Rosen, Material Transfer Agreement and List of peptides provided for experimental use sent to Dr. John D. Roberts, NIEHS, NIH, Research Triangle Park, North Carolina, U.S., Jul. 14, 1999.

Che-Hong Chen, List of peptides provided for experimental use sent to Dr. Jeffery Knauf, University of Cincinnati, Cincinnati, Ohio, U.S., Aug. 10, 1999.

Daria Mochly-Rosen, Material Tranfer Agreement sent to Dr. Johannes W. Hell, University of Wisconsin Medical School, Madison, Wisconsin, U.S., Sep. 22, 1999.

Che-Hong Chen, Material Transfer Agreement, List of peptides provided for experimental use, and related correspondence sent to and from Dr. Yukitaka Shizukuda, University of Illinois, Chicago, Illinois, U.S., Nov. 5, 1999.

Daria Mochly-Rosen, Material Transfer Agreement sent to Dr. Hesam Dehghani, University of Guelph, Ontario, Canada, Nov. 8, 1999.

Joan Brugge for Dr. Cindy Miranti, Harvard Medical School, Boston, Massachusetts, U.S., Material Transfer Agreement and related correspondence sent to and from Dr. Dada Mochly-Rosen, Dec. 21, 1999.

Daria Mochly-Rosen, Material Transfer Agreement and List of peptides provided for experimental use and related correspondence sent to and from Dr. Alexei Kourakine, Buck Center, San Francisco, California, U.S., Jan. 7, 2000.

Daria Mochly-Rosen, Material Transfer Agreement, List of peptides provided for experimental use and related correspondence sent to and from Dr. Ti-Zhi Su, Parke-Davis, Ann Arbor, Michigan, U.S., Jan. 28, 2000.

Daria Mochly-Rosen, Material Transfer Agreement and List of peptides provided for experimental use sent to Dr. Clive Baumgarten, Virginia Commonwealth University, Richmond, Virginia, U.S., Feb. 3, 2000.

Che-Hong Chen, List of peptides provided for experimental use and related correspondence sent to and from Dr. Fiorenzo Battaini, University of Milano, Milano, Italy, Nov. 2, 1998.

Daria Mochly-Rosen, Material Transfer Agreement and List of peptides provided for experimental use sent to Dr. Pedro A. Jose, Georgetown University Hospital, Washington, DC, U.S., Feb. 17, 1999.

Che-Hong Chen, List of peptides provided for experimental use sent to Dr. Karen M. Ridge, Northwestern University, Chicago, Illinois, U.S., Apr. 4, 2000.

Aizawa et al., Anesthesiology (2004) 101(2):381-389.
Alessandri-Haber et al., J Neurosci (2006) 26(14):3864-3874.
Aley and Levine, Exp Brain Res (2003) 148(4):482-487.
Aley et al., J Neurosci (2000) 20(12):4680-4685.
Apple et al., Ann Thorac Surg (2006) 82(2):664-671.
Banci et al., J Biol Chem (2002) 277(15):12988-12997.
Begley et al., Biochem Biophys Res Commun (2004) 318(4):949-954.
Besena et al., J Biol Chem (2004) 279(32):33154-33160.
Braun and Mochly-Rosen, J Mol Cell Cardiol (2003) 35(8):895-903.
Bright and Mochly-Rosen, Stroke (2005) 36(12):2781-2790.
Bright et al., J Neurosci (2004) 24(31):6880-6888.
Brzoska et al., PNAS USA (1995) 92(17):7824-7828.

(56) References Cited

OTHER PUBLICATIONS

Buhagiar et al., Am J Physiol Cell Physiol (2001) 281(3):C1059-C1063.
Cardone et al., J Cell Biol (1994) 124(5):717-727.
Cardone et al., J Cell Biol (1996) 133(5):997-1005.
Chang and Tepperman, Br J Pharmacol (2003) 140(1):41-52.
Chaudary et al., J Pharmacol Exp Ther (2004) 310(3):1190-1198.
Chen et al., Chem Biol (2001) 140:1-7.
Chen et al., PNAS USA (1999) 96(22):12784-12789.
Chen et al., PNAS USA (2001) 98(20):11114-11119.
Churchill et al., Circ Res (2005) 97(1):78-85.
Csukai and Mochly-Rosen, Methods Mol Biol (1998) 88:133-139.
Csukai and Mochly-Rosen, Pharmacol Res (1999) 39(4):253-259.
Dehghani et al., Reproduction (2005) 130(4):453-465.
Dell et al., J Biol Chem (2002) 277(51):49888-49895.
Dempsey et al., Am J Physiol Lung Cell Mol Physiol (2000) 279(3):L429-L438.
Diamond et al., Ann N Y Acad Sci (1991) 625:473-487.
Dina et al., Pain (2005) 115(1-2):191-203.
Disatnik et al., Cell Growth Differ (1994) 5(8):873-880.
Disatnik et al., Exp. Cell Res (1994) 210(2):287-297.
Disatnik et al., J Cell Sci (2002) 115(Pt. 10):2151-2163.
Disatnik et al., J Mol Cell Cardiol (1995) 27(11):2473-2481.
Disatnik et al., PNAS USA (1994) 91(2):559-563.
Dorn and Mochly-Rosen, Annu Rev Physiol (2002) 64:407-429.
Dorn et al., PNAS USA (1999) 96(22):12798-12803.
Endermann and Mochly-Rosen, Methods Mol Biol (2003) 233:307-325.
Endermann et al., Anal Biochem (2003) 313(2):345-347.
Garcia-Navarro et al., Mol Cell Endocrinol (1994) 103(1-2)133-138.
Gray et al., J Biol Chem (1997) 272(49):30945-30951.
Gray et al., J Biol Chem (2004) 279(5):3596-3604.
Gregory et al., J Mol Cell Cardiol (2004) 36(2):313-318.
Hool, Curr Pharm Des (2005) 11(4):549-559.
Hu et al., Am J. Physiol Heart Circ Physiol (2000) 279(6):H2658-H2664.
Hudecz et al., Med Res Rev (2005) 25(6):679-736.
Hundle et al., J Biol Chem (1997) 272(23):15028-15035.
Ikeno et al., Cardiovasc Res (2007) 73(4):699-709.
Inagaki and Mochly-Rosen, J Mol Cell Cardiol (2005) 39(2):203-211.
Inagaki et al., Cardiovasc Res (2006) 70(2):222-230.
Inagaki et al., Circulation (2003) 108(7) 869-875.
Inagaki et al., Circulation (2003) 108(19):2304-2307.
Inagaki et al., Circulation (2005) 111(1):44-50.
Inagaki et al., J Mol Cell Cardiol (2002) 00:1-9.
International Search Report and Written Opinion for PCT/US07/85024, mailed Jul. 7, 2008, 7 pages.
Jaburek et al., Circ. Res. (2006) at <http://circres.ahajournals.org> [DOI:10.1161/01.RES.0000245106.80628.d3].
Jin et al., Am J Physiol Hearth Circ Physiol (2002) 282(6):H1970-H1977.
Johnson and Mochly-Rosen, Circ Res (1995) 76(4):654-663.
Johnson et al., Circ Res (1996) 79(6):1086-1099.
Johnson et al., J Biol Chem (1996) 271(40):24962-24966.
Johnson et al., Life Sci (1995) 57(11):1027-1038.
Joseph et al., Pain (2003) 105(1-2):143-150.
Kheifets et al., J Biol Chem (2006) 281(32):23218-23226.
Knauf et al., J Biol Chem (1999) 274(33):23414-23425.
Knauf et al., J Clin Endocrinol Metab (2002) 87(5):2150-2159.
Koponen et al., J Neurochem (2003) 86(2):442-450.
Lange-Asschenfeldt et al., J Cereb Blood Flow Metab (2004) 24(6):636-645.
Laudanna et al., J Biol Chem (1998) 273(46):30306-30315.
Li et al., Br J Pharmacol (2005) 144(3):301-307.
Liu et al., J Mol Cell Cardiol (1999) 31(10):1937-1948.
Mackay and Mochly-Rosen, Cardiovasc Res (2001) 50(1):65-74.
Mackay and Mochly-Rosen, J Mol Cell Cardiol (2000) 32(8):1585-1588.
Mackay and Mochly-Rosen, J Biol Chem (1999) 274(10):6272-6279.
Mackay and Mochly-Rosen, J Mol Cell Cardiol (2001) 33(7):1301-1307.
Malhotra et al., Am J Physiol Heart Circ Physiol (2005) 289(4):H1343-H1350.
Marinovic et al., Anesthesiology (2005) 103(3):540-547.
Miller et al., Oncogene (2004) 1-5.
Miyamae et al., PNAS USA (1998) 95(14):8262-8267.
Mochly-Rosen, Science (1995) 268(5208):247-251.
Mochly-Rosen and Gordon, Faseb J. (1998) 12(1):35-42.
Mochly-Rosen and Kauvar, Semin Immunol (2000) 12(1):55-61.
Mochly-Rosen and Kauvar, Adv Pharmacol (1998) 44:91-145.
Mochly-Rosen et al., Adv Enzyme Regul (2001) 41:87-97.
Mochly-Rosen et al., Biochem Soc Trans (1995) 23(3):596-600.
Mochly-Rosen et al., Biochemistry (1992) 31(35):8120-8124.
Mochly-Rosen et al., Cell Regul (1990) 1(9):693-706.
Mochly-Rosen et al., Circ Res (2000) 86(11):1173-1179.
Mochly-Rosen et al., J Biol Chem (1991) 266(23):14866-14868.
Mochly-Rosen et al., PNAS USA (1991) 88(9):3997-4000.
Mukherjee et al., Circulation (2006) 114(1 Suppl):I308-I313.
Murriel and Mochly-Rosen, Arch Biochem Biophys (2003) 420(2):246-254.
Murriel et al., J Biol Chem (2004) 279(46):47985-47991.
Parada et al., Neuroscience (2003) 120(1):219-226.
Parada et al., Pain (2005) 113(1-2):185-190.
Pastori et al., Transplantation (2004) 77(11):1627-1631.
Pitchford et al., J Neurosci (1992) 12(11):4540-4544.
Raval et al., J Cereb Blood Flow Metab (2005) 25(6):730-741.
Raval et al., J Neurosci (2003) 23(2):384-391.
Ridge et al., Mol Biol Cell (2002) 13(4):1381-1389.
Robia et al., Am J Physiol Heart Circ Physiol (2005) 289(5):H1941-H1950.
Rodriguez et al., Biochemistry (1999) 38(42):13787-13794.
Rodriguez et al., FEBS Lett (1999) 454(3):240-246.
Ron and Mochly-Rosen, J Biol Chem (1994) 269(34):21395-21398.
Ron and Mochly-Rosen, PNAS USA (1995) 92(2):492-496.
Ron et al., J Biol Chem (1995) 270(41):24180-24187.
Ron et al., PNAS USA (1994) 91(3):839-843.
Satoh et al., Am J Physiol Gastrointest Liver Physiol (2006) [DOI:10.1152/AJPGI.00579.2005].
Schechtman and Mochly-Rosen, Methods Enzymol (2002) 345:470-489.
Schechtman and Mochly-Rosen, Oncogene (2001) 20(44):6339-6347.
Schechtman et al., J Biol Chem (2004) 279(16):15831-15840.
Schechtman et al., Methods Mol Biol (2003) 233:351-357.
Schechtman et al., Methods Mol Biol (2003) 233:345-350.
Shimoni and Liu, Am J Physiol Heart Circ Physiol (2003) 284(4):H1168-H1181.
Shumilla et al., J Pain (2005) 6(8):535-549.
Simon et al., Curr Biol (1993) 3(12):813-821.
Simon et al., Proc Bio Sci (1991) 243(1307)165-171.
Smith and Mochly-Rosen, Biochem Biophys Res Commun (1992) 188(3):1235-1240.
Smith et al., J Biol Chem (1996) 271(28):16753-16757.
Souroujon and Mochly-Rosen, Nat Biotechnol (1998) 16(10):919-924.
Souroujon et al., J Biol Chem (2004) 279(17):17617-17624.
Stebbins and Mochly-Rosen, J Biol Chem (2001) 276(32):29644-29650.
Sweitzer et al., J Pharmacol Exp Ther (2004) 309(2):616-625.
Sweitzer et al., Pain (2004) 110(1-2):281-289.
Szabo et al., Alcohol Clin Exp Res (2005) 29(9):1749-1752.
Tanaka et al., Circulation (2004) 110(Suppl 11):II194-II199.
Tanaka et al., J Thorac Cardiovasc Surg (2005) 129(5):1160-1167.
Vallentin and Mochly-Rosen, J Biol Chem (2007) 282(3):1650-1657.
Van Baal et al., J Biol Chem (2005) 280(11):9870-9878.
Wang et al., Neuropharmacology (2004) 47(1):136-145.
Way et al., Trends Pharmacol Sci (2000) 21(5):181-187.
Wu et al., J Biol Chem (2000) 275(39):29927-29930.
Xiao et al., Am J Physiol Cell Physiol (2001) 281(5):C1477-C1486.

(56) References Cited

OTHER PUBLICATIONS

Xiao et al., Biochem Biophys Res Commun (2003) 306(4):1019-1025.
Yedovitzky et al., J Biol Chem (1997) 272(3):1417-1420.
Zhang et al., Circ Res (1997) 80(5):720-729.
Zhou et al., J Invest Dermatol (1996) 107(2):248-252.
Goodman, Recent developments in the management of secondary hyperparathyroidism, Kidney Int., vol. 59, No. 3, pp. 1187-1201 (2001).
Goodman et al., "The calcimimetic agent AMG 073 lowers plasma parathyroid hormone levels in hemodialysis patients with secondary hyperparathyroidism", J. Am. Soc. Nephrol., vol. 13, No. 4, pp. 1017-1024 (2002).
Goto et al., "Heparin, protamine, and ionized calcium in vitro and in vivo", Anesth. Analg., vol. 64, No. 11, pp. 1081-1084 (1985).
Gunn and Gaffney, "Clinical and laboratory features of calcium-sensing receptor disorders: a systematic review", Ann. Clin. Biochem., vol. 41, Pt. 6, pp. 441-458 (2004).
Gustaffson et al., "Discovery of a class of calcium sensing receptor positive allosteric modulators; 1-(benzothiazol-2-yl)-1-phenylethanols", Bioorg Med Chem Lett., vol. 20, No. 19, 5918-5921 (2010).
Handlogten et al., "Ca(2+)-sensing receptor is a promiscuous divalent cation sensor that responds to lead", Am. J. Physiol. Renal. Physiol., vol. 279, No. 6, pp. F1083-F1091 (2000).
Hauache et al., "Effects of a calcimimetic compound and naturally activating mutations on the human Ca2+ receptor and on Ca2+ receptor/metabotropic glutamate chimeric receptors", Endocrinology, vol. 141, No. 11, pp. 4156-4163 (2000).
Hebert, "Therapeutic use of calcimimetics", Annu. Rev. Med., vol. 57, pp. 349-364 (2006).
Helman et al., "Molecular cloning and primary structure of human chromogranin A (secretory protein I) cDNA", J. Biol. Chem., vol. 263, No. 23, pp. 11559-11563 (1988).
Hendy et al., "Chapter 3 calcium-sensing receptor and associated diseases", Prog. Mol. Biol. Transl. Sci., vol. 89, pp. 31-95 (2009).
Henley et al., "The calcimimetic AMG 641 abrogates parathyroid hyperplasia, bone and vascular calcification abnormalities in uremic rats", Eur. J. Pharmacol., vol. 616, No. 1-3, pp. 306-313 (2009).
Hofer, "Review series on the extracellular Ca(2+)-sensing receptor", J. Cell. Mol. Med., vol. 11, No. 5, pp. 906-907 (2007).
Hofer and Brown, "Extracellular calcium sensing and signaling", Nat. Rev. Mol. Cell Biol., vol. 4, No. 7, pp. 530-538 (2003).
Hong et al., "Effect of D-amino acid substitution on the stability, the secondary structure, and the activity of membrane-active peptide", Biochem. Pharmacol., vol. 58, No. 11, pp. 1775-1780 (1999).
Hrabak, "Common ligands of G-protein-coupled receptors and arginine-utilizing enzymes", Br. J. Pharmacol., vol. 147, No. 8, pp. 835-837 (2006).
Hu, "Allosteric modulators of the human calcium-sensing receptor: structures, sites of action, and therapeutic potentials", Endocr. Metab. Immune Disord. Drug Targets, vol. 8, No. 3, pp. 192-197 (2008).
Hu et al., "Identification of acidic residues in the extracellular loops of the seven-transmembrane domain of the human Ca2+ receptor critical for response to Ca2+ and a positive allosteric modulator", J. Biol. Chem., vol. 277, 48, pp. 46622-46631 (2002).
Hu and Spiegel, "Structure and function of the human calcium-sensing receptor: insights from natural and engineered mutations and allosteric modulators", J. Cell Mol. Med., vol. 11, 5, pp. 908-922 (2007).
Huang et al., "Multiple Ca(2+)-binding sites in the extracellular domain of the Ca(2+)-sensing receptor corresponding to cooperative Ca(2+) response", Biochemistry., vol. 48, No. 2, pp. 388-398 (2009).
Ikari et al., "Activation of a polyvalent cation-sensing receptor decreases magnesium transport via claudin-16", Biochim. Biophys. Acta, vol. 1778, No. 1, pp. 283-290 (2008).
Johnston et al., "Protamine-induced hypocalcemia", Endocrinology, vol. 87, No. 6, pp. 1211-1217 (1970).

Lee et al., "Allosteric activation of the extracellular Ca2+-sensing receptor by L-amino acids enhances ERK1/2 phosphorylation", Biochem. J., vol. 404, No. 1, pp. 141-149 (2007).
Lien et al., "Effects of cinacalcet on bone mineral density in patients with secondary hyperparathyroidism", Nephrol. Dial. Transplant, vol. 20, No. 6, pp. 1232-1237 (2005).
Luthman et al., "The hypocalcemic response to protamine as a measure of bone resorption", Acta Vet. Scand., vol. 14, No. 3, pp. 428-435 (1973).
Luthman and Korpe, "Vitamin D status and hypocalcemic response to protamine in exercised and non-exercised dairy cows", Acta Vet. Scand., vol. 34, No. 1, pp. 53-57 (1993).
Ma et al., "Characterization of highly efficacious allosteric agonists of the human calcium-sensing receptor", J. Pharmacol Exp. Ther., vol. 337, No. 1, pp. 275-284 (2011).
Maclean, "KAI-4169: A Novel Calcium Sensing Receptor (CaSR) Agonist for the Treatment of CKD-MBD", TIDES Meeting Boston May 2011.
Magno et al., "The calcium-sensing receptor: a molecular perspective", Endocr. Rev., vol. 32, No. 1, pp. 3-30 (2011).
Marie, "The calcium-sensing receptor in bone cells: a potential therapeutic target in osteoporosis", Bone, vol. 46, No. 3, pp. 571-576 (2010).
Martin et al., "KAI-4169, a Novel Peptide for the Treatment of Chronic Kidney Disease—Mineral and Bone Disorder, in a Phase I Study in Healthy Males", (Posted: FR-PO1238) American Society of Nephrology, Philadelphia, Nov. 2011.
Martin et al., "Characterization of KAI-4169, A Novel Peptide for the Treatment of Chronic Kidney Disease Mineral and Bone Disorder, in a Single-dose Study in Hemodialysis Subjects", (Posted: FR-PO1256) American Society of Nephrology, Philadelphia, Nov. 2011.
Martin et al., "The Effect of KAI-4169, a Novel Treatment for Chronic Kidney Disease—Mineral and Bone Disorder, on Serum Phosphorus Kinetics Post-Hemodialysis", (Poster: FR -PO1232) American Society of Nephrology, Philadelphia, Nov. 2011.
McLarnon et al., "Aminoglycoside antibiotics induce pH-sensitive activation of the calcium-sensing receptor", Biochem. Biophys. Res. Commun., vol. 297, No. 1, pp. 71-77 (2002).
Mendoza et al., "Direct upregulation of parathyroid calcium-sensing receptor and vitamin D receptor by calcimimetics in uremic rats", Am. J. Physiol. Renal. Physiol., vol. 296, No. 3, pp. F605-F613 (2009).
Mizobuchi et al., "Calcimimetic compound upregulates decreased calcium-sensing receptor expression level in parathyroid glands of rats with chronic renal insufficiency", J. Am. Soc. Nephrol., vol. 15, No. 10, pp. 2579-2587 (2004).
Moe et al., "R-568 reduces ectopic calcification in a rat model of chronic kidney disease-mineral bone disorder (CKD-MBD)", Nephrol. Dial. Transplant, vol. 24, No. 8, pp. 2371-2377 (2009).
Mun et al., "A double mutation in the extracellular Ca2+-sensing receptor's venus flytrap domain that selectively disables L-amino acid sensing", J. Biol. Chem., vol. 280, No. 32, pp. 29067-29072 (2005).
Mun et al., "The Venus Fly Trap domain of the extracellular Ca2+-sensing receptor is required for L-amino acid sensing", J. Biol. Chem., vol. 279, No. 50, pp. 51739-51744 (2004).
Chattopadhyay et al., "Regulation of secretion of PTHrP by Ca(2+)-sensing receptor in human astrocytes, astrocytomas, and meningiomas", Am. J. Physiol. Cell Physiol., vol. 279(3): C691-C699 (2000).
Church et al., "Characterization of histamine secretion from mechanically dispersed human lung mast cells: effects of anti-IgE, calcium ionophore A23187, compound 48/80, and basic polypeptides", J. Immunol., vol. 129, No. 5, pp. 2116-2121 (1982).
Lagunoff et al., "Agents that release histamine from mast cells", Ann. Rev. Pharmacol. Toxicol., vol. 23, pp. 331-351 (1983).
Miller et al., "RACK1 regulates Src-mediated Sam68 and p190RhoGAP signaling", Oncogene, vol. 23, pp. 5682-5686 (2004).
Satoh et al., "PKC-delta and -epsilon regulate NF-kappaB activation induced by cholecystokinin and TNF-alpha in pancreatic acinar cells", Am. J. Physiol. Gastrointest. Liver Physiol., vol. 287, No. 3, p. G582-591 (2004).

(56) References Cited

OTHER PUBLICATIONS

Arenas et al., "Implementation of 'K/DOQI clinical practice guideline for bone metabolism and disease in chronic kidney disease' after the introduction cinacalcet in a population of patients on chronic haemodialysis", Nephrology Dialysis Transplantation, vol. 22, No. 6, pp. 1639-1644 (2007).
Conigrave et al., "Dietary protein and bone health: roles of amino acid-sensing receptors in the control of calcium metabolism and bone homeostasis", Annu. Rev. Nutr., vol. 28, pp. 131-155 (2008).
Goodman "Calcimimetic agents for the treatment of secondary hyperparathyroidism", Semin. Nephrol., vol. 24, No. 5, pp. 460-463 (2004).
Harris et al., "Pharmacokinetics, pharmacodynamics, and safety of cinacalcet hydrochloride in hemodialysis patients at doses up to 200 mg once daily", Am. J. Kidney Dis., vol. 44, No. 6, pp. 1070-1076 (2004).
International Search Report from PCT Patent Application No. PCT/US2008/051706 mailed Sep. 24., 2008, application now published as International Patent Publication No. WO2008/089491 on Jul. 24, 2008.
International Search Report from related PCT Patent Application No. PCT/US2010/043792 mailed Apr. 26, 2011, application now published as International patent Publication No. WO2011/014707 on Feb. 3, 2011.
International Search Report from related PCT Patent Application No. PCT/US2012/041759 mailed Sep. 26, 2012.
Padhi and Harris, "Clinical pharmcokinetic and pharmacodynamic profile of cinacalcet hydrochloride", Clin. Pharmaocokinetics, vol. 48, No. 5, pp. 303-311 (2009).
Platt et al., "Middle-term use of cinacalcet in paediatric dialysis patients", Pediatr. Nephrol., vol. 25, No. 1, pp. 143-148 (2009).
Schaefer et al., "Efficacy of cinacalcet administered with the first meal after dialysis: the SENSOR study", Clinical Nephrology, vol. 70, No. 2, pp. 126-134 (2008).
Ureña and Frazão, "Calcimimetic agents: Review and perspectives", Kidney International, vol. 63, Supplement 85, pp. S91-S96 (2003).
Abes et al., "Vectorization of morpholino oligomers by the (R-Ahx-R)4 peptide allows efficient splicing correction in the absence of endosomolytic agents", J. Contr. Rel., vol. 116, No. 3, pp. 304-313 (2006).
Aladren, "Cinacalcet reduces vascular and soft tissue calcification in secondary hyperparathyroidism (SHPT) in hemodialysis patients", Clin. Nephrol., vol. 71, No. 2, pp. 207-213, (2009).
Almirall et al., "Effects of cinacalcet on vascular calcification in haemodialysis patients", Nephrol. Dial. Transplant, vol. 25, No. 8, pp. 2800 (2002).
Anderson et al., "The effect of protamine derivatives on calcium metabolism in patients with malignancy", Br. J. Cancer., vol. 21, No. 1, pp. 48-55 (1967).
Antonsen et al., "A calcimimetic agent acutely suppresses parathyroid hormone levels in patients with chronic renal failure", Rapid communication, Kidney Int., vol. 53, No. 1, pp. 223-227 (1998).
Arey et al., "A novel calcium-sensing receptor antagonist transiently stimulates parathyroid hormone secretion in vivo", Endocrinology, vol. 146, No. 4, pp. 2015-2022 (2005).
Aridor et al., "Exocytosis in mast cells by basic secretagogues: evidence for direct activation of GTP-binding proteins", J. Cell Biol., vol. 111, pp. 909-917 (1990).
Bakker et al., "8R-lisuride is a potent stereospecific histamine H1-receptor partial agonist", Mol. Pharmacol., vol. 65, No. 3, pp. 538-549 (2004).
Baruch et al., "KAI-4169, a novel Peptide Agonist of the Calcium Sensing Receptor for the Treatment of Secondary Hyperparathyroidism" Endocrine Society 93rd Annual Meeting (ENDO 2011), Boston Jun. 4-8, 2011 (Endocr Rev 32: P2-98) (2011).
Bell et al., "Calcimimetic KAI-4169 Reduces Parathyroid Hormone (PTH) Dose-dependently", (Poster#:SA23) ISN World Congress of Nephrology, Vancouver, Apr. 8-12, 2011.

Block et al., "The impact of calcimimetics on mineral metabolism and secondary hyperparathyroidism in end-stage renal disease", Kidney Int. Suppl., vol. 87, pp. S131-S136 (2003).
Block et al., "Results of a Phase 2 study evaluating the safety and efficacy of KAI-4169, a novel peptide for the treatment of chronic kidney disease—mineral and bone disorder in hemodialysis subjects", (Poster: LBCT-P03147) American Society of Nephrology, Philadelphia, Nov. 2011.
Breitwieser, "Calcium sensing receptors and calcium oscillations: calcium as a first messenger", Curr. Top. Dev. Biol., vol. 73, pp. 85-114 (2006).
Brennan and Conigrave, "Regulation of cellular signal transduction pathways by the extracellular calcium-sensing receptor", Curr. Pharm. Biotechnol., vol. 10, No. 3, pp. 270-281 (2009).
Brown et al., "Decreased calcium-sensing receptor expression in hyperplastic parathyroid glands of uremic rats: role of dietary phosphate", Kidney Int., vol. 55, 4pp. 1284-1292 (1999).
Brown, "Clinical utility of calcimimetics targeting the extracellular calcium-sensing receptor (CaSR)", Biochem. Pharmacol., vol. 80, No. 3, pp. 297-307 (2010).
Brown et al., "Cloning and characterization of an extracellular Ca(2+)-sensing receptor from bovine parathyroid", Nature, vol. 366 No. 6455, pp. 575-580 (1993).
Brown et al., "Quabain and low extracellular potassium inhibit PTH secretion from bovine parathyroid cells by a mechanism that does not involve increases in the cytosolic calcium concentration", Metabolism, vol. 36, No. 1, pp. 36-42 (1987).
Brown et al., "Neomycin mimics the effects of high extracellular calcium concentrations on parathyroid function in dispersed bovine parathyroid cells", Endocrinology, vol. 128, No. 6, pp. 3047-3054 (1991).
Brown and Macleod, "Extracellular calcium sensing and extracellular calcium signaling", Physiol. Rev., vol. 81, No. 1, pp. 239-297 (2001).
Busque et al., "L-type amino acids stimulate gastric acid secretion by activation of the calcium-sensing receptor in parietal cells", Am. J. Physiol. Gastrointest. Liver Physiol., vol. 289 No. 4, pp. G664-G669. (2005).
Caudrillier et al., "Calcium-sensing receptor as a potential modulator of vascular calcification in chronic kidney disease", J. Nephrol., vol. 23, No. 1, pp. 17-22 (2010).
Chen and Goodman, "Role of the calcium-sensing receptor in parathyroid gland physiology", Am. J. Physiol. Renal Physiol., vol. 286, No. 6, pp. F1005-F1011 (2004).
Colloton et al., "Cinacalcet HCl attenuates parathyroid hyperplasia in a rat model of secondary hyperparathyroidism", Kidney Int., vol. 67, No. 2, pp. 467-476 (2005).
Conigrave and Brown, "Taste receptors in the gastrointestinal tract. II. L-amino acid sensing by calcium-sensing receptors: implications for GI physiology", Am. J. Physiol. Gastrointest Liver Physiol., vol. 291, No. 5, pp. G753-G761 (2006).
Conigrave et al., "Dietary protein and bone health: roles of amino acid-sensing receptors in the control of calcium metabolism and bone homeostasis", Annu. Rev. Nutr., vol. 28, pp. 24.1-24.25 (2008).
Conigrave et al., "L-amino acid sensing by the calcium-sensing receptor: a general mechanism for coupling protein and calcium metabolism?", Eur. J. Clin. Nutr., vol. 56, No. 11, pp. 1072-1080 (2002).
Conigrave et al., "Physiological significance of L-amino acid sensing by extracellular Ca(2+)-sensing receptors", Biochem. Soc. Trans., vol. 35, Pt. 5, pp. 1195-1198 (2007).
Conigrave et al., "L-amino acids regulate parathyroid hormone secretion", J. Biol. Chem., vol. 279, No. 37, pp. 38151-38159 (2004).
Conigrave et al., "Aromatic L-amino acids activate the calcium-sensing receptor", J. Nutr., vol. 137, No. 6 Suppl. 1, pp. 1524S-1527S, discussion 1548S (2007).
Conigrave et al. "L-amino acid sensing by the extracellular Ca2+-sensing receptor", Proc. Natl. Acad. Sci. USA, vol. 97, No. 9, pp. 4814-4819 (2000).
Conigrave et al., "Cooperative multi-modal sensing and therapeutic implications of the extracellular Ca(2+) sensing receptor", Trends Pharmacol. Sci., vol. 10, pp. 401-407 (2000).

(56) References Cited

OTHER PUBLICATIONS

Delaney, "Managing bone mineral disorders in CKD: an overview of current therapies", J. Ren. Care, vol. 35, Suppl 1, pp. 107-110 (2009).
Fan et al., "Mutational analysis of the cysteines in the extracellular domain of the human Ca2+ receptor: effects on cell surface expression, dimerization and signal transduction", FEBS Lett., vol. 436, No. 3, pp. 353-356 (1998).
Fasciotto et al., "Pancreastatin, a presumed product of chromogranin-A (secretory protein-I) processing, inhibits secretion from porcine parathyroid cells in culture", Endocrinology, vol. 125, No. 3, pp. 1617-1622 (1989).
Foreman and Lichtenstein, "Induction of histamine secretion by polycations", Biochim. Biophys. Acta, vol. 629, No. 3, pp. 587-603 (1980).
Geibel et al., "Calcium-sensing receptor abrogates secretagogue-induced increases in intestinal net fluid secretion by enhancing cyclic nucleotide destruction", Proc. Natl. Acad. Sci. USA, vol. 103, No. 25, pp. 9390-9397 (2006).
Gogusev et al., "Depressed expression of calcium receptor in parathyroid gland tissue of patients with hyperparathyroidism", Kidney Int., vol. 51, No. 1, pp. 328-336 (1997).
Pologe et al., "Primary structure and subcellular localization of the knob-associated histidine-rich protein of *Plasmodium falciparum*", PNAS USA, vol. 84, pp. 7139-7143 (1987).
Spormann et al., "Carboxypeptidase yscS: gtene structure and function of the vacular enzyme", Eur. J. Biochem., vol. 197, pp. 399-405 (1991).
Yu et al., "Two-dimensional NMR studies and secondary structure of cobrotoxin in aqueous solution", Eur. J. Biochem., vol. 193, pp. 789-799 (1990).
Nagano, "Pharmacological and clinical properties of calcimimetics: calcium receptor activators that afford an innovative approach to controlling hyperparathyroidism", Pharmacol. Ther., vol. 109, No. 3, pp. 339-365 (2006).
Navarro et al., "Toxicological and pharmacological effects of D-arginine", Basic Clin. Pharmacol.Toxicol., vol. 97, No. 3, pp. 149-154 (2005).
Nemeth and Fox, "Calcimimetic Compounds: a Direct Approach to Controlling Plasma Levels of Parathyroid Hormone in Hyperparathyroidism", Trends Endocrinol. Metab., vol. 10, No. 2, pp. 66-71 (1999).
Nemeth, "Pharmacodynamics of the type II calcimimetic compound cinacalcet HCl", J. Pharm. Exp. Ther., vol. 38, pp. 627-635 (2004).
Pace et al., "Dimerization of the calcium-sensing receptor occurs within the extracellular domain and is eliminated by Cys → Ser mutations at Cys101 and Cys236", J. Biol. Chem., vol. 274, vol. 17, pp. 11629-11934 (1999).
Pickthorn et al., "PK/PD Modeling of Transdermal Delivery of a Novel Peptide, KAI-4169, for the Treatment of Chronic Kidney Disease-Bone and Mineral Disorder (CKD-MBD)", (Poster: FR-PO1245) American Society of Nephrology, Philadelphia, Nov. 2011.
Potts et al., "*Protamine: a powerful* in vivo *inhibitor of bone resorption*", Calcif. Tissue Int., vol. 36, vol. 2, pp. 189-193 (1984).
Price et al., "Artery calcification in uremic rats is increased by a low protein diet and prevented by treatment with ibandronate", Kidney Int., vol. 70, No. 9, pp. 1577-1583 (2006).
Quinn et al., "Ca2+-sensing receptor: a target for polyamines", Am. J. Physiol., vol. 273, No. 4, Pt. 1, pp. C1315-C1323 (1997).
Ray et al., "Elucidation of the role of peptide linker in calcium-sensing receptor activation process", J. Biol. Chem., vol. 282, No. 8, pp. 5310-5317 (2007).
Ray et al., "The role of cysteines and charged amino acids in extracellular loops of the human Ca(2+) receptor in cell surface expression and receptor activation processes", Endocrinology, vol. 145, No. 8, pp. 3892-3903 (2004).
Ray et al., "Identification of the cysteine residues in the amino-terminal extracellular domain of the human Ca(2+) receptor critical for dimerization. Implications for function of monomeric Ca(2+) receptor", J. Biol. Chem., vol. 274, No. 39, pp. 27642-27650 (1999).

Ray and Northup, "Evidence for distinct cation and calcimimetic compound (NPS 568) recognition domains in the transmembrane regions of the human Ca2+ receptor", J. Biol. Chem., vol. 277, No. 21, pp. 18908-18913 (2002).
Rey et al., "Amino acid-stimulated Ca2+ oscillations produced by the Ca2+-sensing receptor are mediated by a phospholipase C/inositol 1,4,5-trisphosphate-independent pathway that requires G12, Rho, filamin-A, and the actin cytoskeleton", J. Biol. Chem., vol. 280, No. 24, pp. 22875-22882 (2005).
Riccardi et al., "Novel regulatory aspects of the extracellular Ca2+-sensing receptor, CaR", Pflugers Arch., vol. 458, No. 6, pp. 1007-1022 (2009).
Riccardi and Gamba, "The many roles of the calcium-sensing receptor in health and disease", Arch. Med. Res., vol. 30, No. 6, pp. 436-448 (1999).
Rodriguez et al., "The calcium-sensing receptor: a key factor in the pathogenesis of secondary hyperparathyroidism", Am. J. Physiol. Renal Physiol., vol. 288, No. 2, pp. F253-F264 (2005).
Sandak et al., "Agonists and allosteric modulators of the calcium-sensing receptor and their therapeutic applications", Mol. Pharmacol., vol. 76, No. 6, pp. 1131-1144. (2009).
Sajid-Crockett et al., "Cinacalcet for the treatment of primary hyperparathyroidism", Metabolism, vol. 57, No. 4, pp. 517-521 (2008).
Shen et al., "The PK/PD Relationship of a Novel peptide, KAI-4169 Following a Single-Dose Administration to Healthy Young Males", Endocrine Society 93rd Annual Meeting (ENDO 2011), Boston Jun. 4-8, 2011 (Endocr Rev 32; p. 1-23) (2011).
Shoback et al., "The calcimimetic cinacalcet normalizes serum calcium in subjects with primary hyperparathyroidism", J. Clin. Endocrinol. Metab., vol. 88, No. 12, pp. 5644-5649 (2003).
Shoback et al., "Relationship between parathyroid hormone secretion and cytosolic calcium concentration in dispersed bovine parathyroid cells", Proc. Natl. Acad. Sci. USA., vol. 81, No. 10, pp. 3113-3117 (1984).
Stoelting et al., "Haemodynamic changes and circulating histamine concentrations following protamine administration to patients and dogs", Can. Anaesth. Soc. J., vol. 31, No. 5, pp. 534-540 (1984).
Trivedi et al., "Recent updates on the calcium-sensing receptor as a drug target", Curr. Med. Chem., vol. 15, No. 2, pp. 178-186 (2008).
Wada et al., "Calcimimetic NPS R-568 prevents parathyroid hyperplasia in rats with severe secondary hyperparathyroidism", Kidney Int., vol. 57, No. 1, pp. 50-58 (2000).
Walter et al., "Preclinical PK and PD relationship for KAI-4169, a novel peptide agonist of the calcium sensing receptor", Endocirine Society, 93rd Annual Meeting, Boston Jun. 4-8, 2011, Endocr. Rev., vol. 32, pp. P1-P198 (2011).
Walter et al., "KAI-4169, a Novel Peptide Agonist of the Calcium Sensing Receptor, Suppresses Parathyroid Hormone, Parathyroid Gland Hyperplasia and Ectopic Calcification in a Rodent Model of Chronic Renal Dysfunction", (Poster: FR-PO1222) American Society of Nephrology, Philadelphia, Nov. 2011.
Ward et al., "Disulfide bonds in the extracellular calcium-polyvalent cation-sensing receptor correlate with dimer formation and its response to divalent cations in vitro", J. Biol. Chem., vol. 273, No. 23, pp. 14476-14483 (1998).
Ward et al., "Aminoglycosides induce acute cell signaling and chronic cell death in renal cells that express the calcium-sensing receptor", J. Am. Soc. Nephrol., vol. 16, No. 5, pp. 1236-1244 (2005).
Yang et al., "Discovery and structure-activity relationships of trisubstituted pyrimidines/pyridines as novel calcium-sensing receptor antagonists", J. Med. Chem., vol. 52, No. 4, pp. 1204-1208 (2009).
Ye et al., "Amyloid-beta proteins activate Ca(2+)-permeable channels through calcium-sensing receptors", J. Neurosci. Res., vol. 47, No. 5, pp. 547-554 (1997).
Young and Rozengurt, "Amino acids and Ca2+ stimulate different patterns of Ca2+ oscillations through the Ca2+-sensing receptor", Am. J. Physiol. Cell Physiol., vol. 282, No. 6, pp. C1414-C1422 (2002).

(56) References Cited

OTHER PUBLICATIONS

Zhang et al., "L-phenylalanine and NPS R-467 synergistically potentiate the function of the extracellular calcium-sensing receptor through distinct sites", J. Biol. Chem., vol. 277, No. 37, pp. 33736-33741 (2002).

Zhang et al., Three adjacent serines in the extracellular domains of the CaR are required for L-amino acid-mediated potentiation of receptor function, J. Biol. Chem., vol. 277, No. 37, pp. 33727-33735 (2002).

Zhang et al., "The extracellular calcium-sensing receptor dimerizes through multiple types of intermolecular interactions", J. Biol. Chem., vol. 276, No. 7, pp. 5316-5322 (2001).

\* cited by examiner

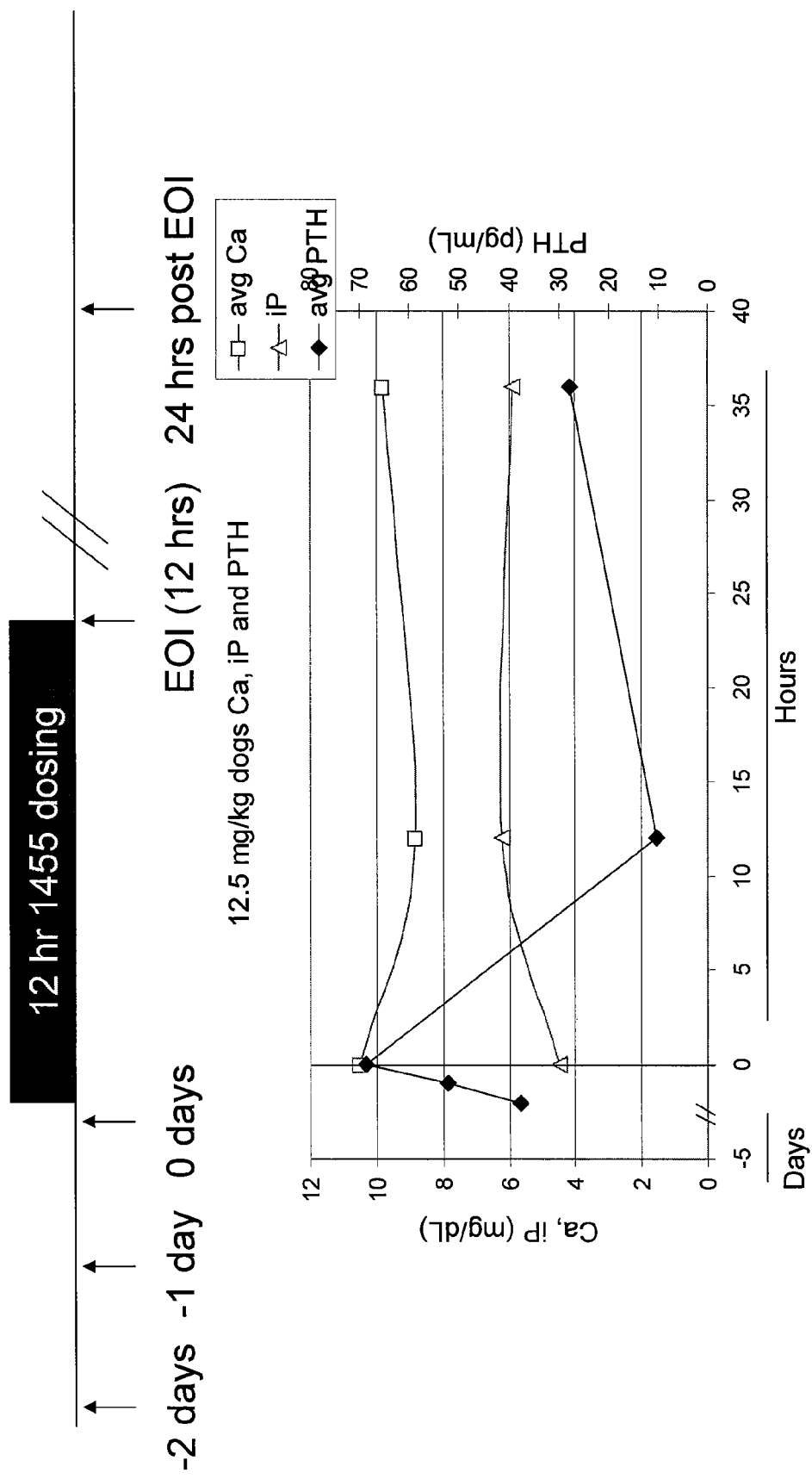
Figure 1. Relationship between PTH, Ca & iP levels

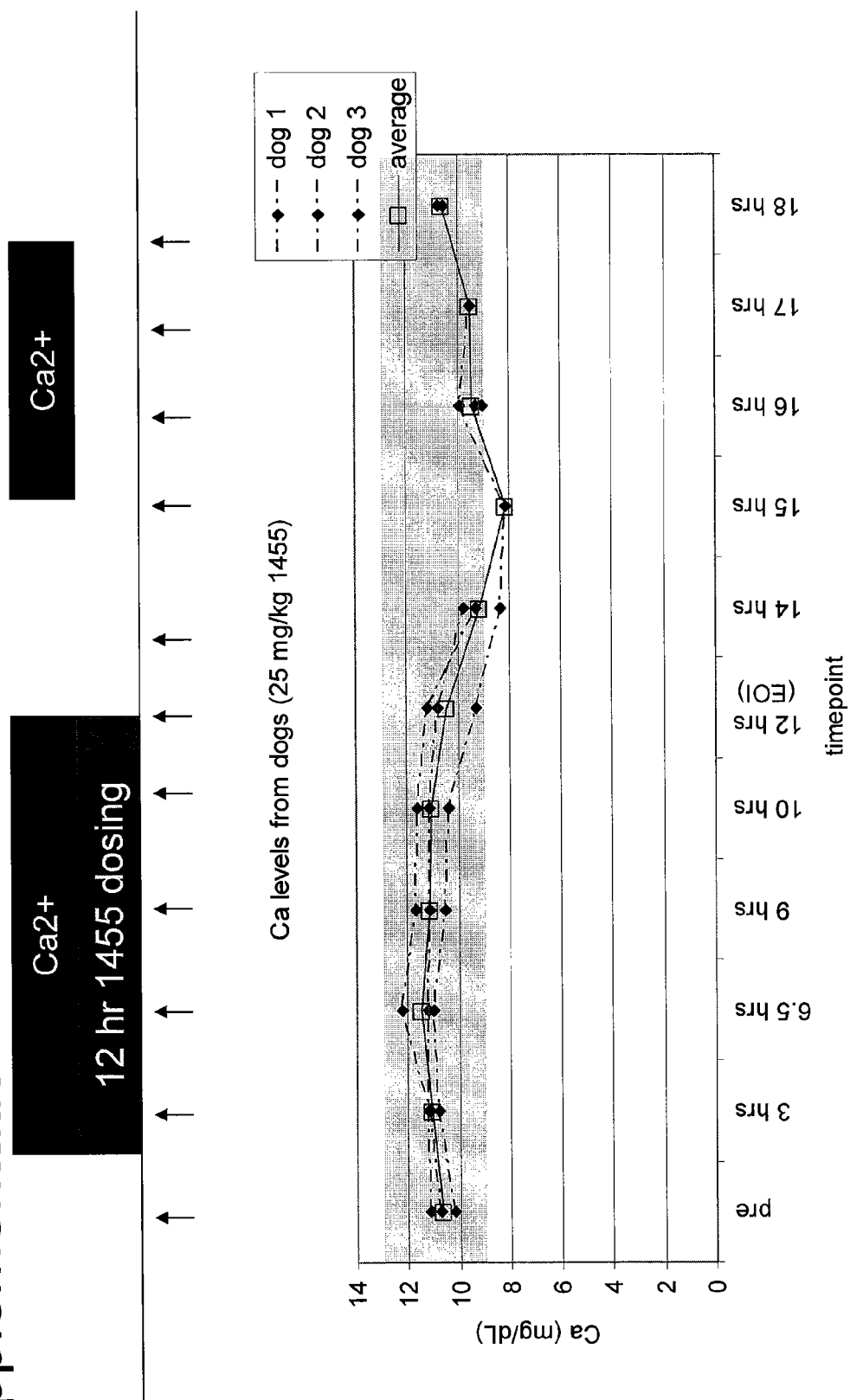
Figure 2. Dog safety pharm (25 mg/kg); Ca2+ supplementation

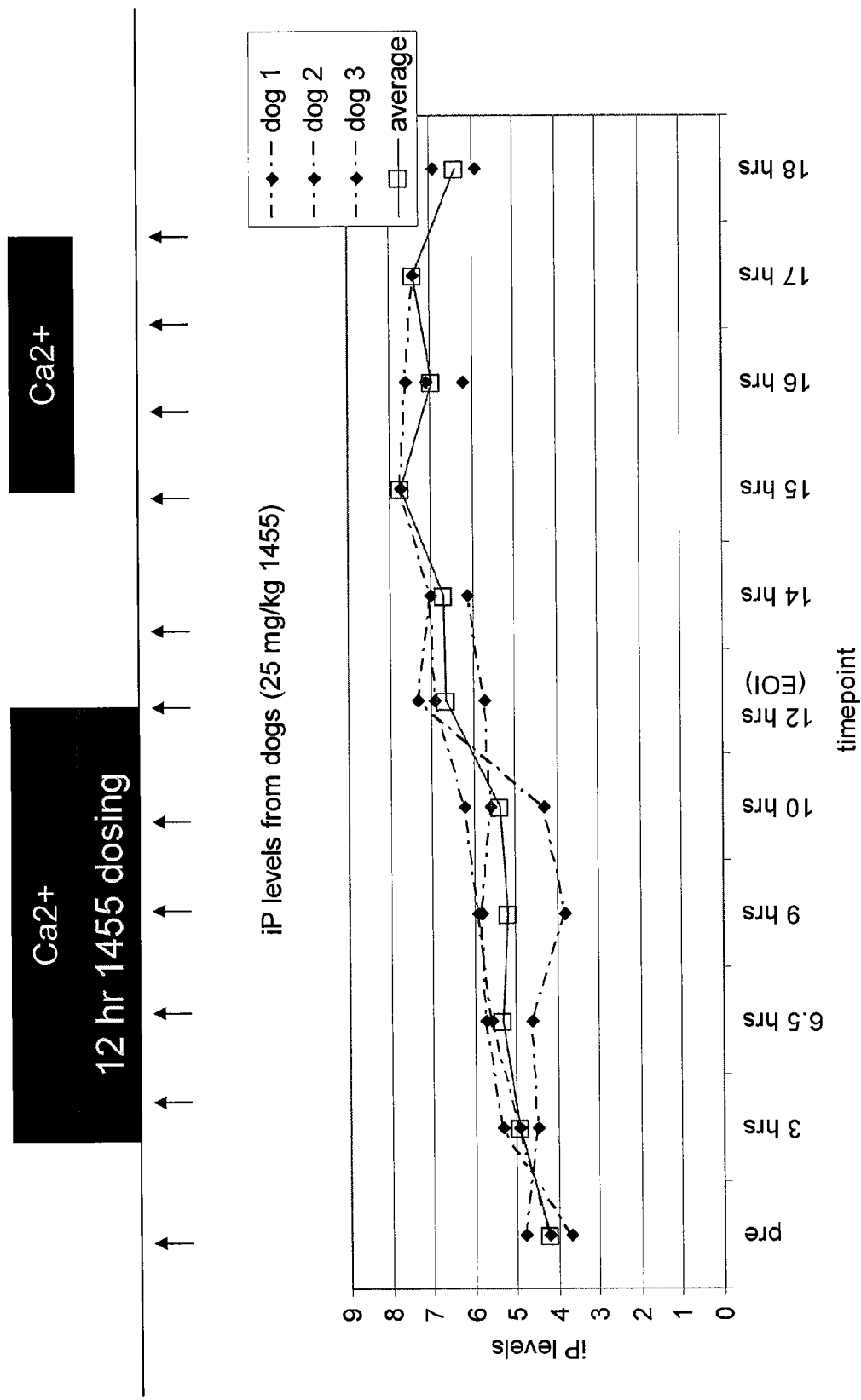
Figure 3. Dog safety pharm (25 mg/kg); Ca2+ supp. iP

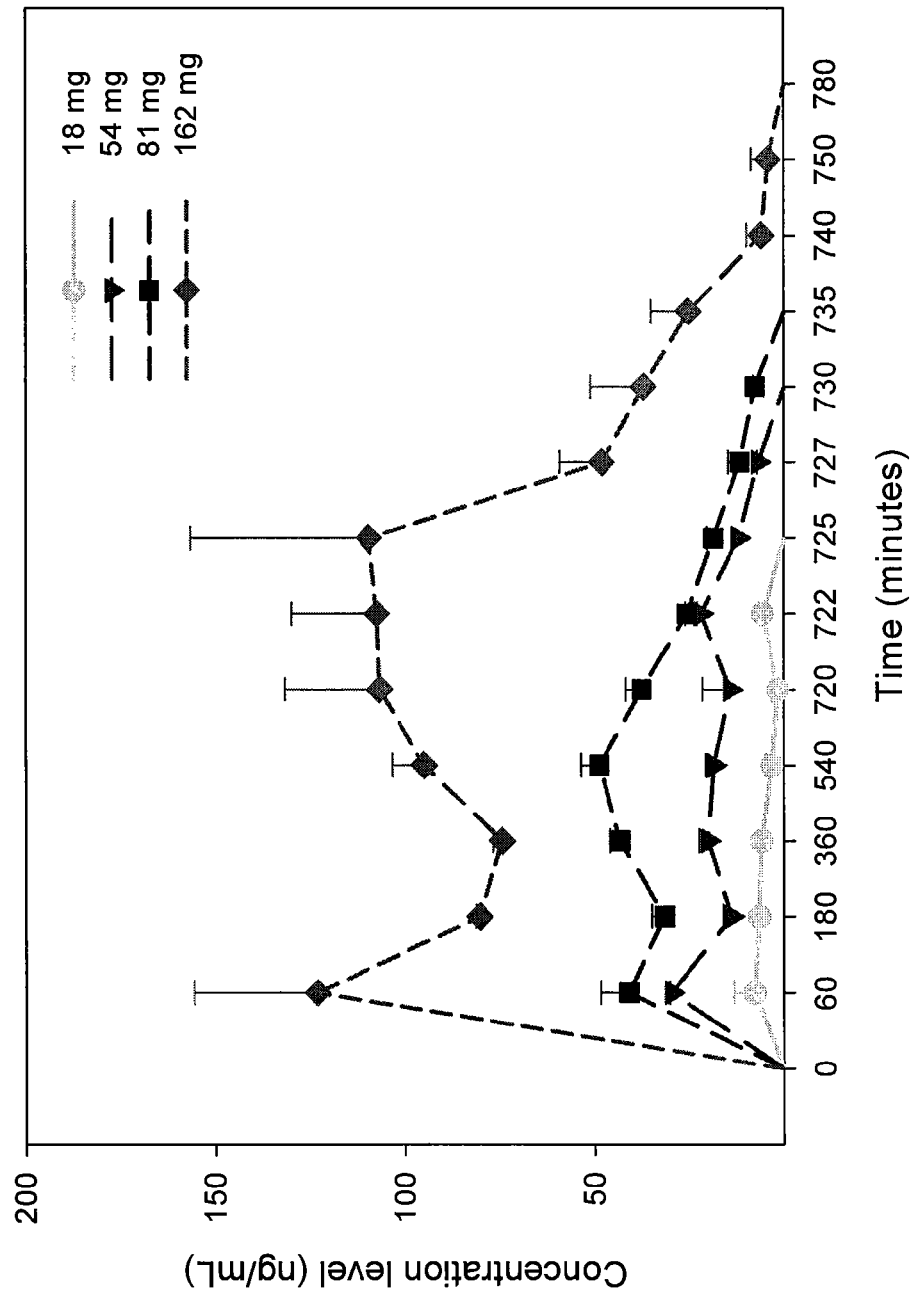
Figure 4. KAI -1455 Plasma Pharmacokinetics

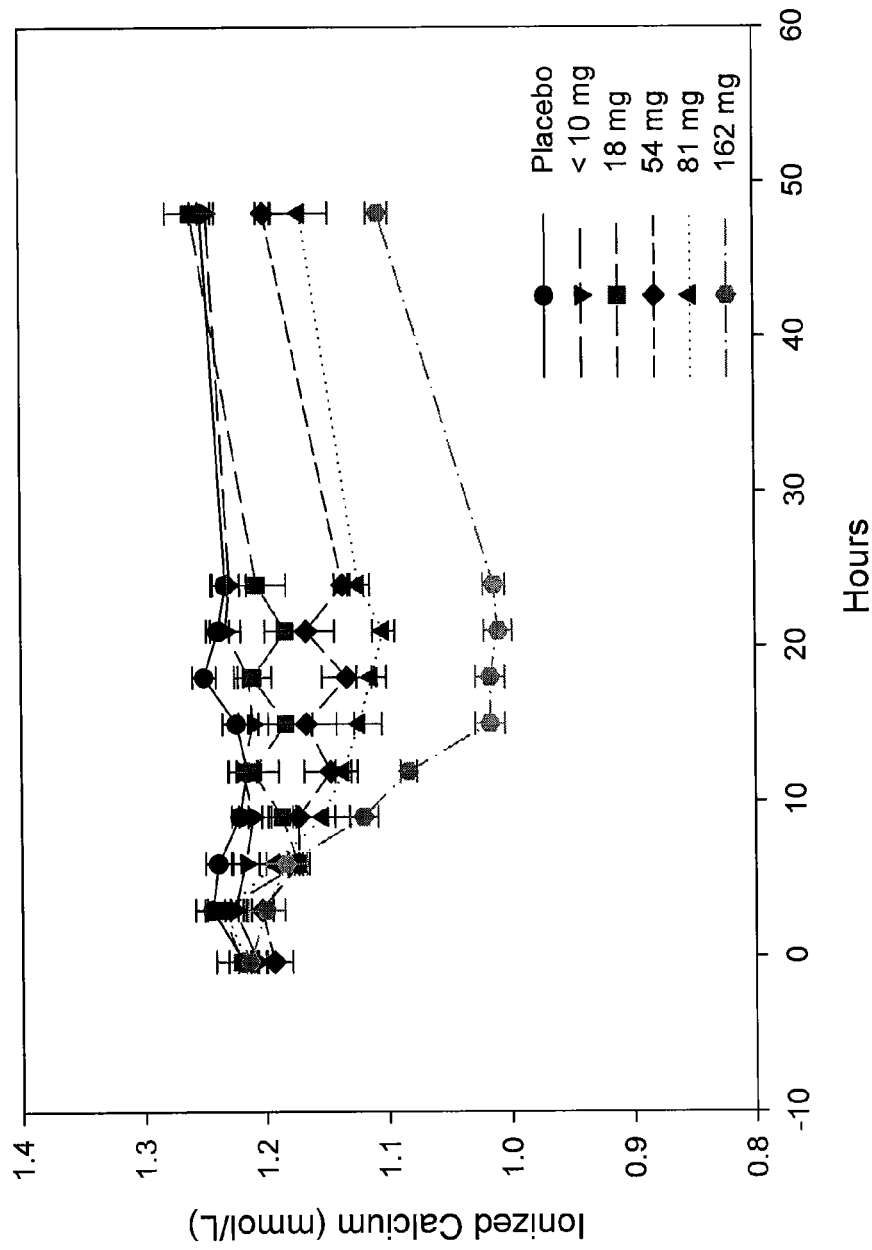
Figure 5. 1455-001: Ionized Calcium by Treatment Group

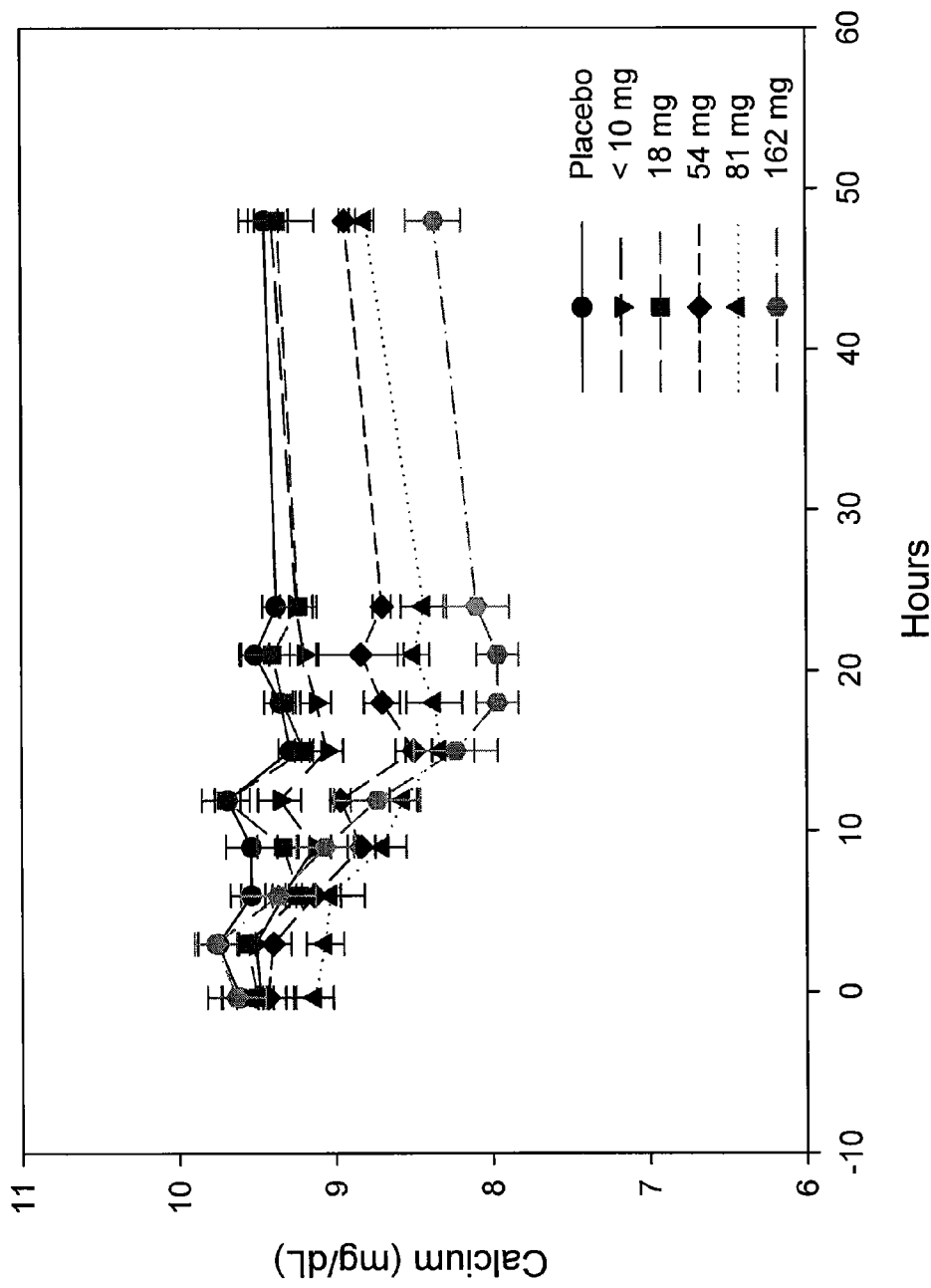
Figure 6. 1455-001: Total Calcium by Treatment Group

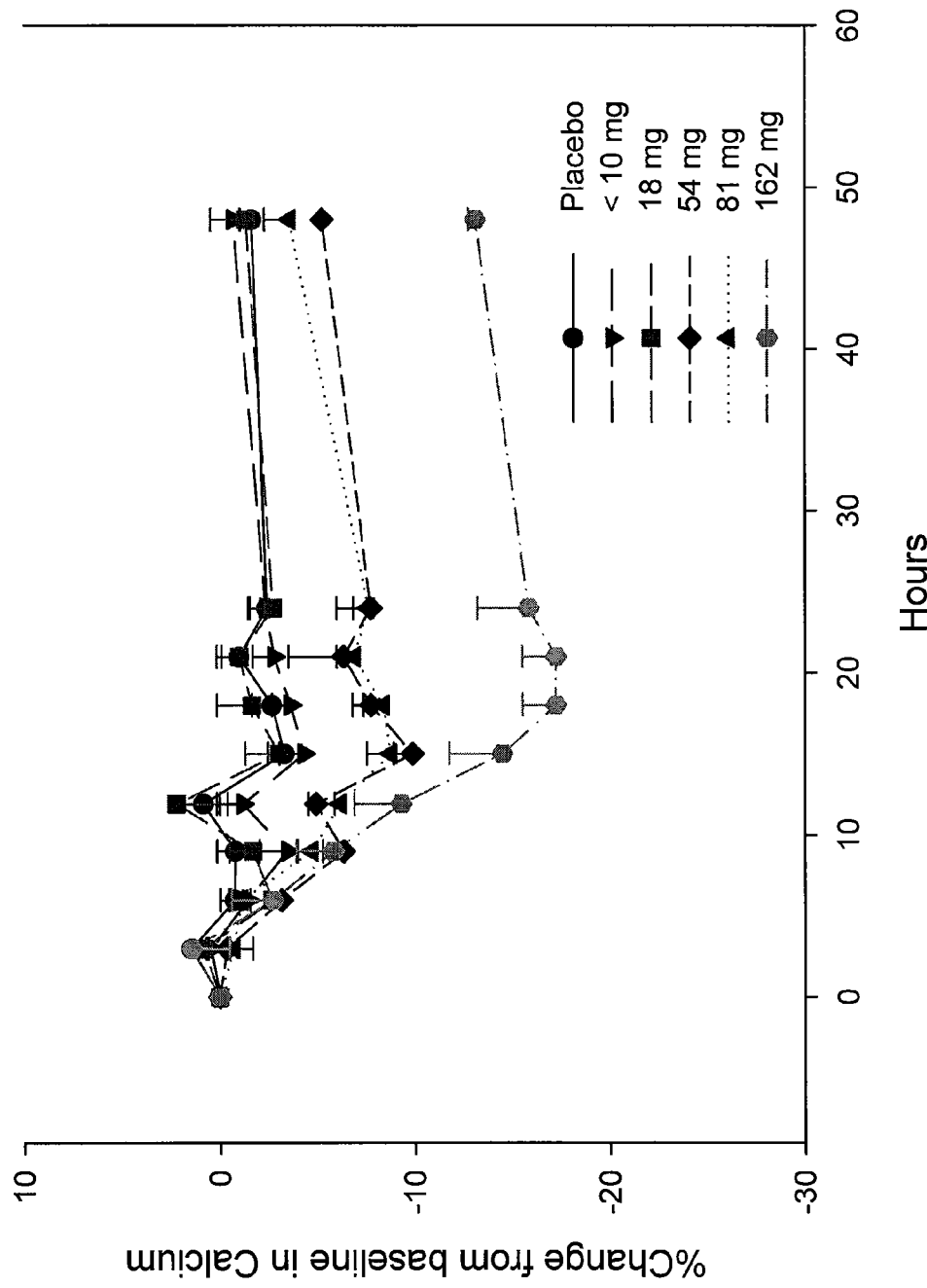
Figure 7. 1455-001: % Change in Calcium by Treatment Groups

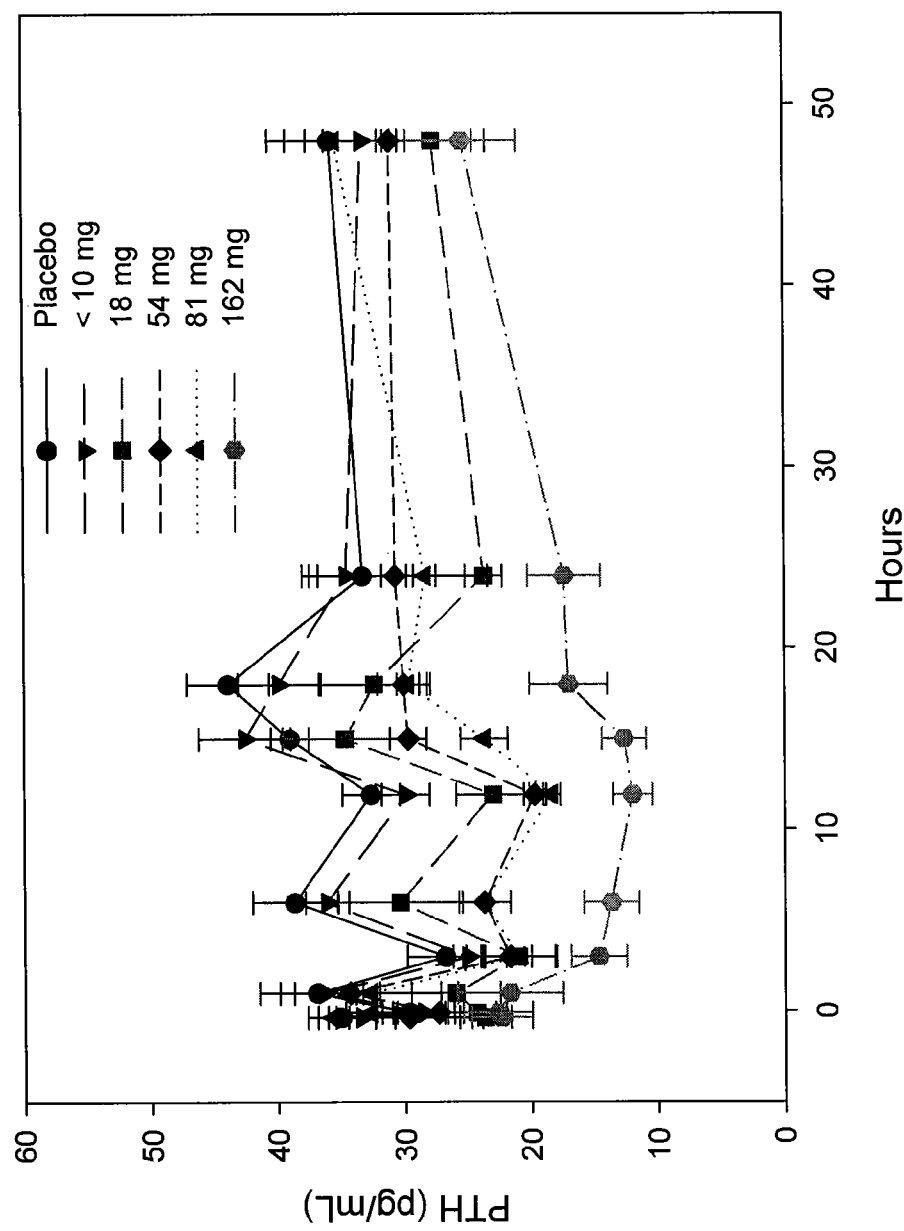
Figure 8. 1455-001: Plasma PTH by Treatment Group

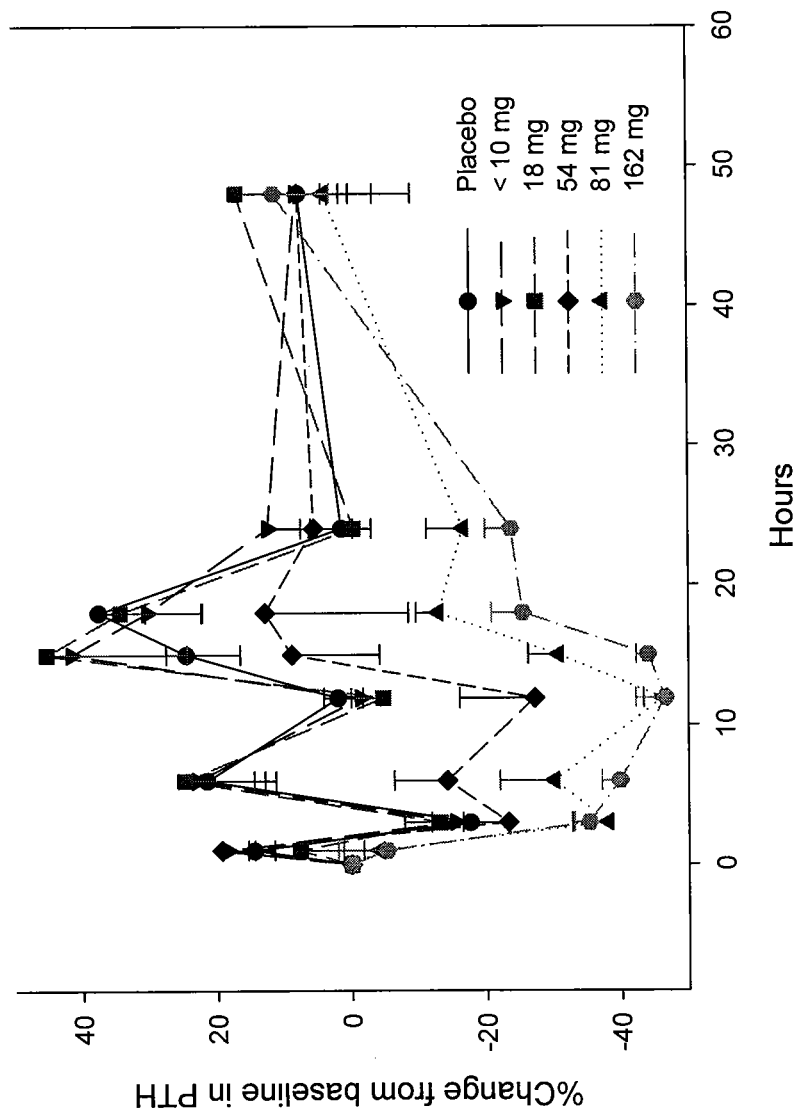
Figure 9. 1455-001: % Change in PTH by Treatment Groups

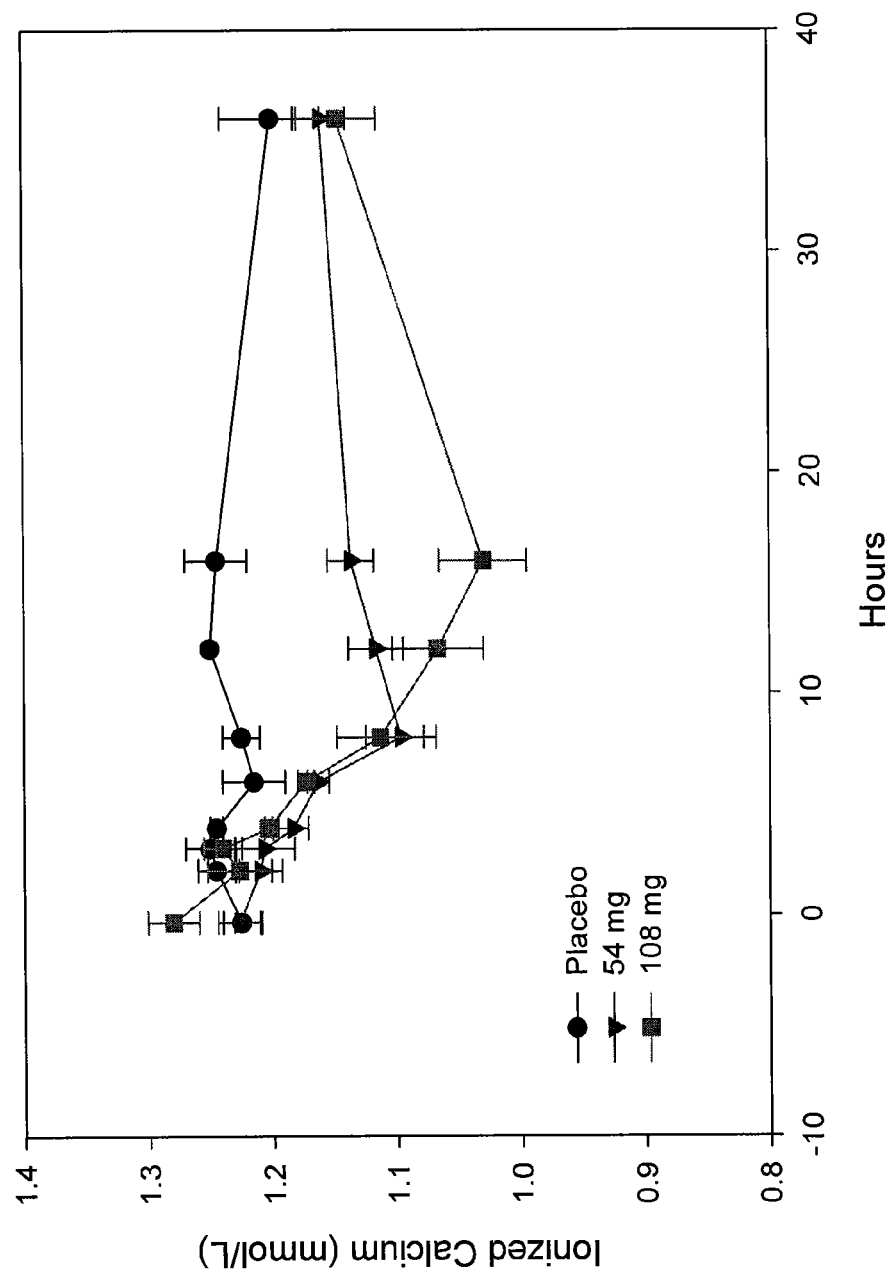
Figure 10. 1455-001: Ionized Calcium by Treatment Group

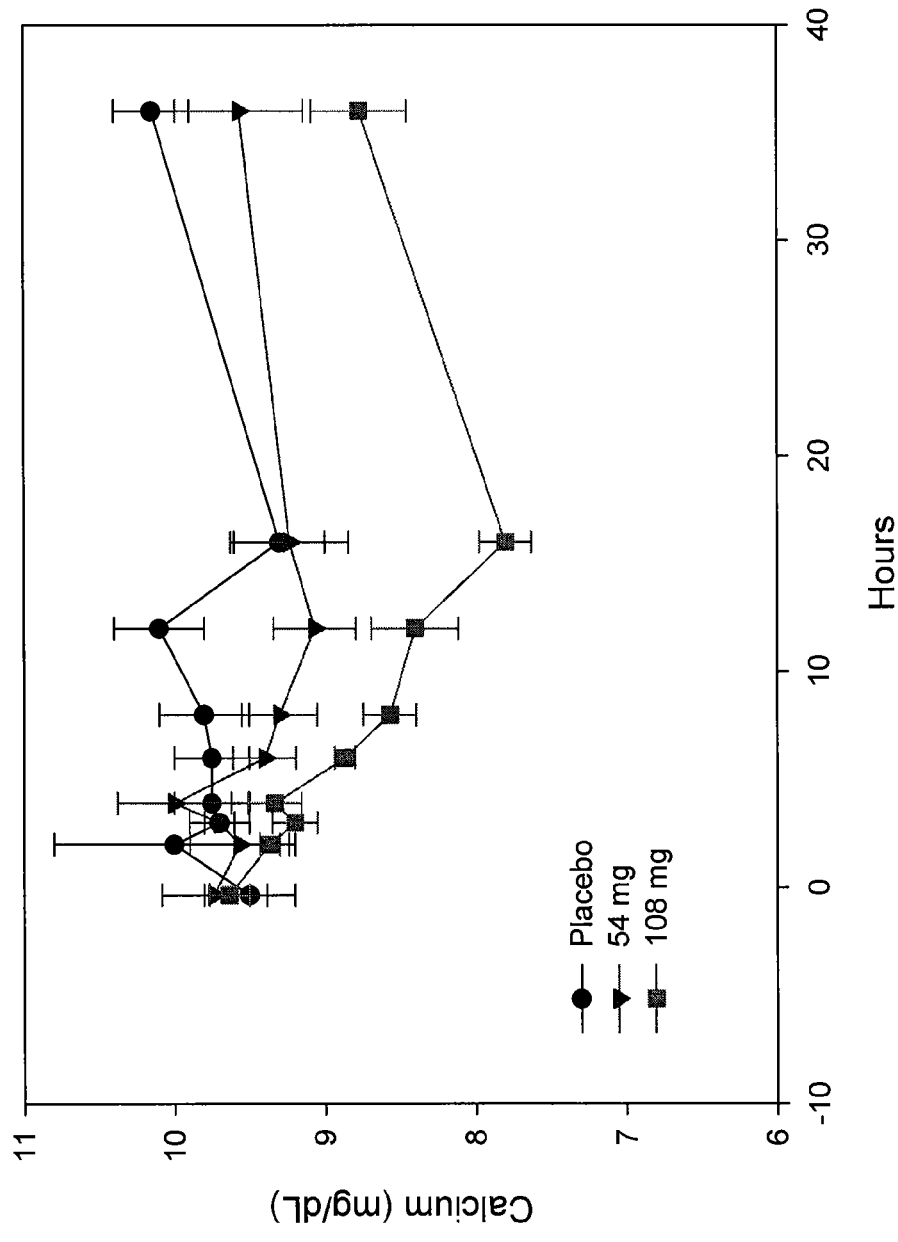
Figure 11. 1455-001: Total Calcium by Treatment Group

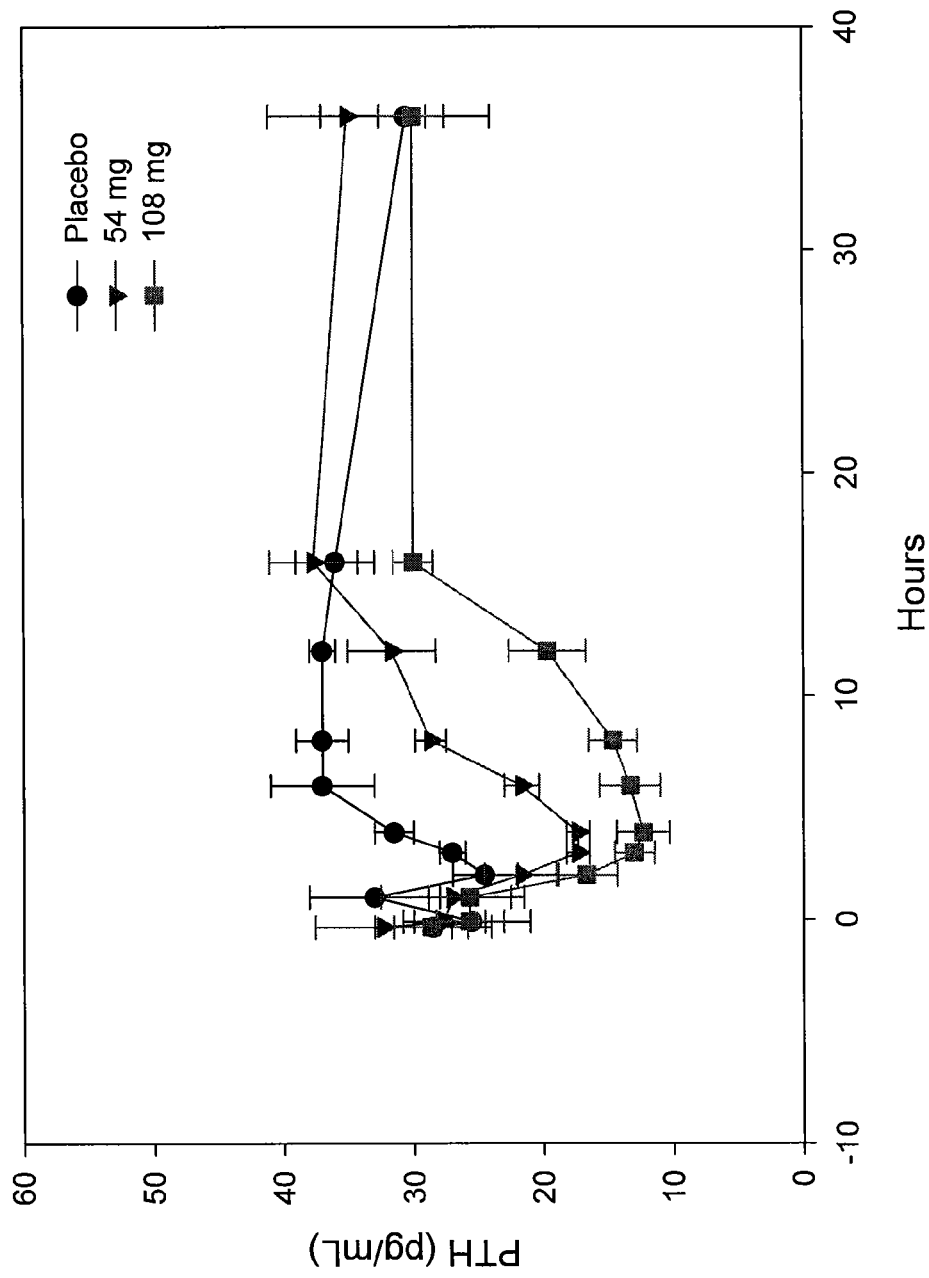
Figure 12. 1455-001: Plasma PTH by Treatment Group

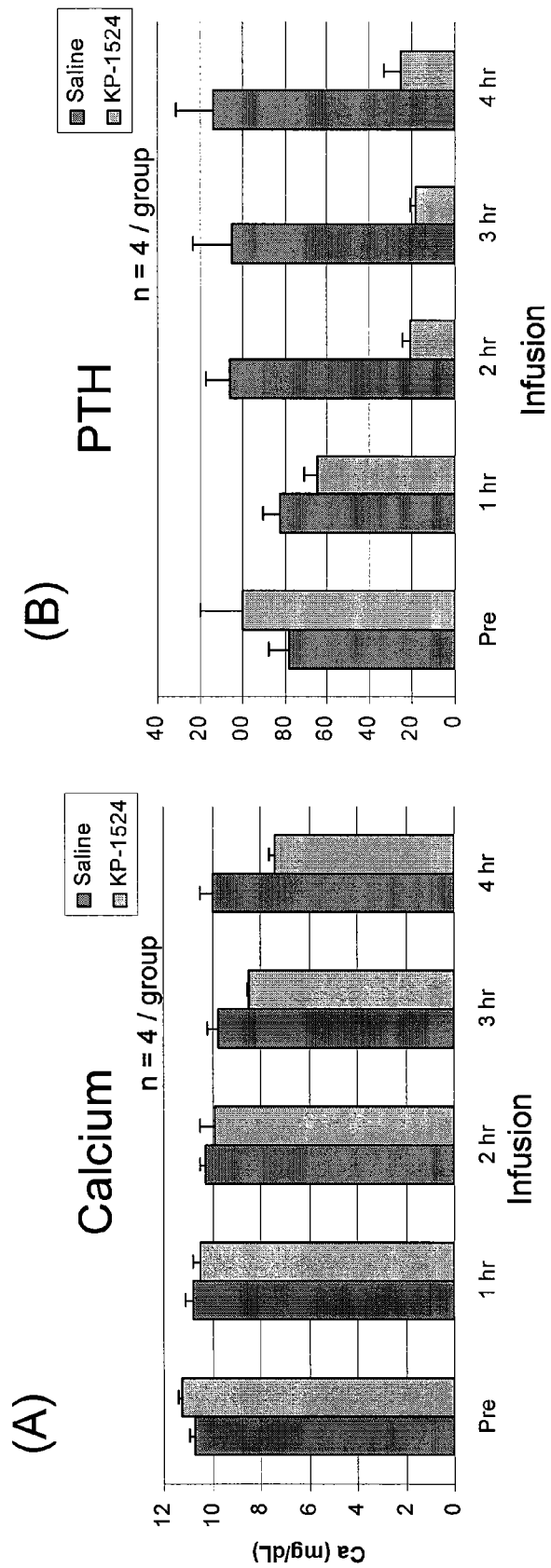
Figure 13. Infusion with KP-1524 Lowers Calcium

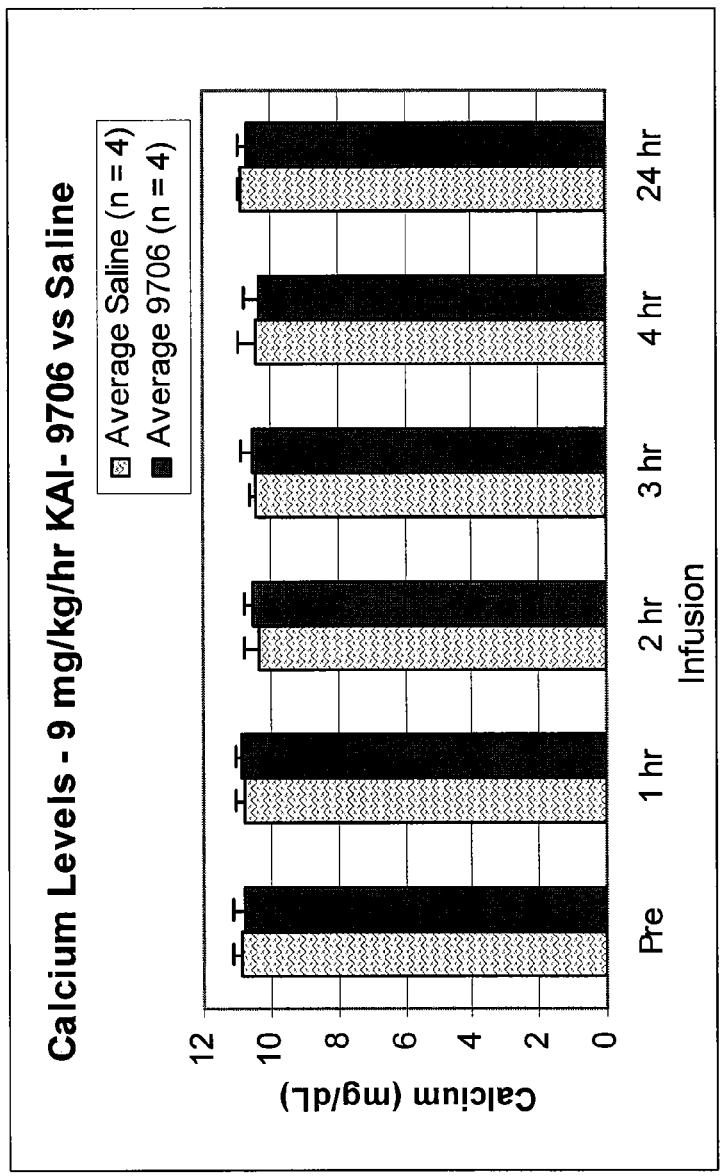
Figure 14. High Dose of un-capped KAI-1455 (9706)

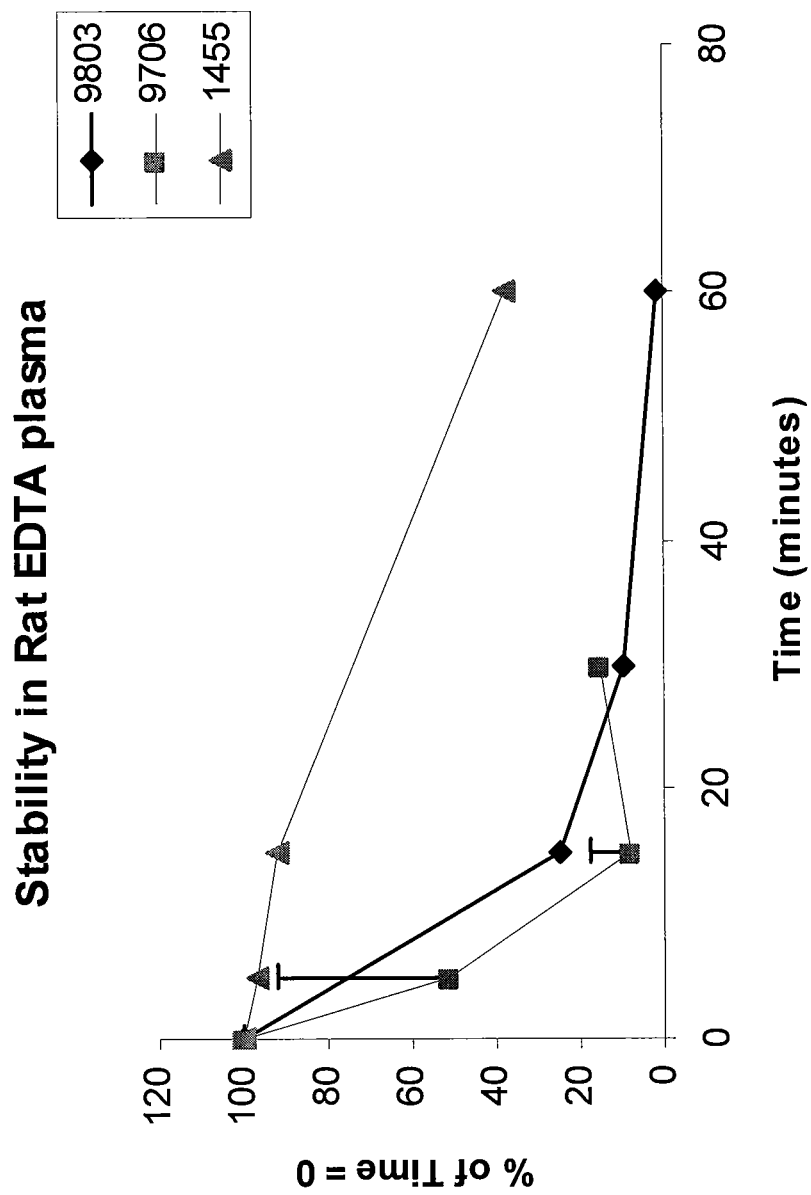
Figure 15. In vitro Plasma Stability Data

POLYCATIONIC CALCIUM MODULATOR PEPTIDES FOR THE TREATMENT OF HYPERPARATHYROIDISM AND HYPERCALCEMIC DISORDERS

CROSS-REFERENCE TO RELATED APPLICATIONS

This application claims priority from U.S. Provisional Application Ser. No. 60/859,597, filed 16 Nov. 2006. The content of this document is incorporated by reference herein in its entirety.

TECHNICAL FIELD

The current invention relates to polycationic calcium modulator peptides and pharmaceutical compositions thereof, and to the use of such peptides and compositions in methods for decreasing parathyroid hormone (PTH) and/or treating hypercalcemia in a subject in need of such treatment.

BACKGROUND ART

Calcium Homeostasis

Calcium homeostasis is the mechanism by which the body maintains adequate calcium levels. The process is highly regulated, and involves a complex interplay between calcium absorption, transport, storage in bones, deposition in other tissues, and excretion.

PTH is the most important regulator of serum calcium levels, and functions to increase the concentration of calcium in the blood by enhancing the release of calcium from bone through the process of bone resorption; increasing reabsorption of calcium from the renal tubules; and enhancing calcium absorption in the intestine by increasing the production of 1,25-$(OH)_2$ vitamin D, the active form of vitamin D. PTH also stimulates phosphorus excretion from the kidney, and increases release from bone.

PTH secretion is regulated by the calcium sensing receptor (CaSR), a G-protein coupled receptor expressed on the cell surface of parathyroid cells, which detects small fluctuations in the concentration of extracellular calcium ion ($Ca^{2+}$) and responds by altering the secretion of PTH. Activation of the CaSR by $Ca^{2+}$ inhibits PTH secretion within seconds to minutes, and this process may be modulated by protein kinase C (PKC) phosphorylation of the receptor. The CaSR is also expressed on osteoblasts and in the kidney, where it regulates renal $Ca^{2+}$ excretion.

In addition, PTH regulates phosphorus homeostasis. PTH stimulates the parathyroid hormone receptor 1 (PTHR1) on both apical (brush border membrane) and basolateral membranes. PTHR1 stimulation leads to an increase in urinary excretion of phosphate (Pi) as a consequence of reduction by internalization of the renal $Na^+$/phosphate (NaPi-IIa) co-transporter on the brush border membrane. PKC activation would be expected to similarly reduce Pi excretion.

PTH is also involved in the regulation of osteoblasts and osteoclasts in bone. PTH increases serum $Ca^{2+}$ by increasing bone resorption and renal absorption of calcium. PTH stimulates osteoblasts to produce RANK ligand (RANKL), which binds to the RANK receptor and activates the osteoclasts, leading to an increase in bone resorption and an increase in serum $Ca^{2+}$. Osteoprotegerin (OPG) is a decoy receptor for RANKL which blocks bone resorption. Osteoporosis is caused by an imbalance between the processes of bone resorption by osteoclasts and bone formation by osteoblasts.

Hypercalcemia and Hyperparathyroidism

The human body contains approximately 1 kg of calcium, 99% of which resides in bone. Under normal conditions, circulating calcium ion ($Ca^{2+}$) is tightly maintained at a level of about 8 to 10 mg/dL (i.e., 2.25-2.5 mmol/L; ~600 mg). Approximately 1 g of elemental calcium ($Ca^{2+}$) is ingested daily. Of this amount, approximately 200 mg/day is absorbed, and 800 mg/day is excreted. In addition, approximately 500 mg/day is released by bone resorption or is deposited into bone. About 10 g of $Ca^{2+}$ is filtered through the kidney per day, with about 200 mg appearing in the urine, and the remainder being reabsorbed.

Hypercalcemia is an elevated calcium level in the blood. Acute hypercalcemia can result in gastrointestinal (anorexia, nausea, vomiting); renal (polyuria, polydipsia), neuro-muscular (depression, confusion, stupor, coma) and cardiac (bradycardia, first degree atrioventricular) symptoms. Chronic hypercalcemia is also associated with gastrointestinal (dyspepsia, constipation, pancreatitis); renal (nephrolithiasis, nephrocalcinosis), neuro-muscular (weakness) and cardiac (hypertension block, digitalis sensitivity) symptoms. Abnormal heart rhythms can result, and EKG findings of a short QT interval and a widened T wave suggest hypercalcemia. Hypercalcemia may be asymptomatic, with symptoms more commonly occurring at high calcium levels (12.0 mg/dL or 3 mmol/l). Severe hypercalcemia (above 15-16 mg/dL or 3.75-4 mmol/l) is considered a medical emergency: at these levels, coma and cardiac arrest can result.

Hypercalcemia is frequently caused by hyperparathyroidism, leading to excess bone resorption and elevated levels of serum calcium. In primary sporadic hyperparathyroidism, PTH is overproduced by a single parathyroid adenoma; less commonly, multiple adenomas or diffuse parathyroid gland hyperplasia may be causative. Increased PTH secretion leads to a net increase in bone resorption, with release of $Ca^{2+}$ and phosphate (Pi). PTH also enhances renal reabsorption of $Ca^{2+}$ and inhibits reabsorption of phosphate (Pi), resulting in a net increase in serum calcium and a decrease in phosphate.

Secondary hyperparathyroidism occurs when a decrease in the plasma $Ca^{2+}$ level stimulates PTH secretion. The most important cause of secondary hyperparathyroidism is chronic renal insufficiency, such as that in renal polycystic disease or chronic pyelonephritis, or chronic renal failure, such as that in hemodialysis patients. Excess PTH may be produced in response to hypocalcemia resulting from low calcium intake, GI disorders, renal insufficiency, vitamin D deficiency, and renal hypercalciuria. Tertiary hyperparathyroidism may occur after a long period of secondary hyperparathyroidism and hypercalcemia.

Malignancy is the most common cause of non-PTH mediated hypercalcemia. Hypercalcemia of malignancy, is an uncommon but severe complication of cancer, affecting between 10% and 20% of cancer patients, and may occur with both solid tumors and leukemia. The condition has an abrupt onset and has a very poor prognosis, with a median survival of only six weeks. Growth factors (GF) regulate the production of parathyroid hormone-related protein (PTHrP) in tumor cells. Tumor cells may be stimulated by autocrine GF to increase production of PTHrP, leading to enhanced bone resorption. Tumor cells metastatic to bone may also secrete PTHrP, which can resorb bone and release additional GF which in turn act in a paracrine manner to further enhance PTHrP production.

Calcimimetic Agents

Calcimimetic agents are drugs that mimic the action of calcium on various tissues. Phenylalkylamine calcimimetic agents with activity on the parathyroid calcium sensing receptor (CaSR) have been described. See Nemeth et al., *Proc.*

*Natl. Acad. Sci.*, 95:4040-4045 (1998). One such agent, Cinacalcet, is marketed for the treatment of hyperparathyroidism. In addition, the CaSR can also sense and respond to other divalent and polyvalent cations, and to organic polycations, such as spermine, hexacyclin, polylysine, polyarginine, protamine, amyloid β-peptides, neomycin, and gentamycin, although these cations are reported to lack selectivity and to possess relatively low potency for the CaSR. See Nagano & Nemeth, *J. Pharmacol. Sci.*, 97:355-360 (2005); see also Brown et al., *J. Bone Miner. Res.*, 6:1217-1225 (1991).

Protein Kinase C

Protein kinase C (PKC) is a key enzyme in signal transduction involved in a variety of cellular functions, including cell growth, regulation of gene expression and ion channel activity. The PKC family of isozymes includes at least 11 different protein kinases which can be divided into at least three subfamilies based on their homology and sensitivity to activators. Members of the classical or cPKC subfamily, alpha, beta ($β_I$, $β_{II}$), and gamma isozymes, contain four homologous domains (C1, C2, C3 and C4) inter-spaced with isozyme-unique (variable or V) regions, and require calcium, phosphatidylserine (PS), and diacylglycerol (DG) or phorbol esters for activation. Members of the novel or nPKC subfamily, delta, epsilon, eta, and theta isozymes, do not require calcium for activation. Finally, members of the atypical or aPKC subfamily, zeta and lambda/iota isozymes, are insensitive to DG, phorbol esters and calcium.

Studies on the subcellular distribution of PKC isozymes demonstrate that activation of PKC results in its redistribution in the cells (also termed translocation), such that activated PKC isozymes associate with the plasma membrane, cytoskeletal elements, nuclei, and other subcellular compartments. It appears that the unique cellular functions of different PKC isozymes are determined by their subcellular location. For example, activated $β_I$ PKC is found inside the nucleus, whereas activated $β_{II}$ PKC is found at the perinucleus and cell periphery of cardiac myocytes. Further, in the same cells, epsilon PKC binds to cross-striated structures (possibly the contractile elements) and cell-cell contacts following activation or after addition of exogenous activated epsilon PKC to fixed cells. The localization of different PKC isozymes to different areas of the cell in turn appears due to binding of the activated isozymes to specific anchoring molecules termed Receptors for Activated C-Kinase (RACKs).

RACKs are thought to function by selectively anchoring activated PKC isozymes to their respective subcellular sites. RACKs bind only activated PKC and are not necessarily substrates of the enzyme. Nor is the binding to RACKs mediated via the catalytic domain of the kinase. Translocation of PKC reflects binding of the activated enzyme to RACKs anchored to the cell particulate fraction and the binding to RACKs is required for PKC to produce its cellular responses. Inhibition of PKC binding to RACKs in vivo inhibits PKC translocation and PKC-mediated function.

cDNA clones encoding RACK1 and RACK2 have been identified. Both are homologs of the beta subunit of G proteins, a receptor for another translocating protein kinase, the beta-adrenergic receptor kinase, beta-ARK. Similar to G-proteins, RACK1, and RACK2 have seven WD40 repeats. Recent data suggest that RACK1 is a selective anchoring protein for activated βII PKC. Studies have shown that RACK2 (also called β'-COP) is a selective binding protein for εPKC. Csukai et al. *J. Biol. Chem.* 1997; 272:29200-29206.

Translocation of PKC is required for proper function of PKC isozymes. Peptides that mimic either the PKC-binding site on RACKs or the RACK-binding site on PKC are isozyme-specific translocation inhibitors of PKC that selectively inhibit the function of the enzyme in vivo.

SUMMARY OF THE INVENTION

The current invention relates to polycationic calcium modulator peptides and pharmaceutical compositions thereof, and to the use of such peptides and compositions in methods for decreasing parathyroid hormone (PTH) and/or for treating hypercalcemia in a subject in need of such treatment.

In one aspect, the invention provides a method for decreasing parathyroid hormone (PTH) levels in a subject, comprising administering a therapeutically effective amount of a calcium modulator peptide to a subject in need thereof, whereby serum PTH is reduced.

In another aspect, the invention provides a method for treating hypercalcemia, comprising administering a therapeutically effective amount of a calcium modulator peptide to a subject in need thereof, whereby serum calcium is reduced.

In another aspect, the invention provides a method for treating bone disease, comprising administering a therapeutically effective amount of a polycationic calcium modulator peptide to a subject in need thereof, whereby bone turnover is reduced.

In some embodiments, the calcium modulator peptide comprises:

a) a polycationic peptide comprising 5 to 20 amino acids which are positively charged at physiological pH, an amino terminus, a carboxy terminus, and a first thiol-containing residue;

wherein the polycationic peptide is chemically modified at the amino terminus, the carboxy terminus, or both; and b) a cargo peptide comprising a second thiol-containing residue;

wherein the second thiol-containing residue is disulfide bonded to the first thiol-containing residue.

In other embodiments, the calcium modulator peptide comprises:

a) a first polycationic peptide comprising at least 3 amino acids which are positively charged at physiological pH, a first amino terminus, a first carboxy terminus, and a first thiol-containing residue;

wherein the first polycationic peptide is chemically modified at the first amino terminus, the first carboxy terminus, or both; and b) a second polycationic peptide comprising at least 3 amino acids which are positively charged at physiological pH, a second amino terminus, a second carboxy terminus, and a second thiol-containing residue;

wherein the second polycationic peptide is chemically modified at the second amino terminus, the second carboxy terminus, or both;

wherein the calcium modulator peptide comprises 6 to 30 amino acids which are positively charged at physiological pH.

In further embodiments, the calcium modulator peptide comprises:

a polycationic peptide comprising 5 to 20 amino acids which are positively charged at physiological pH, an amino terminus, a carboxy terminus, and a first thiol-containing residue;

wherein the polycationic peptide is chemically modified at the amino terminus, the carboxy terminus, or both; and wherein the first thiol-containing residue contains a thiol group which may be present as a free thiol or in a protected form.

In some embodiments, the therapeutically effective amount of the calcium modulator peptide is sufficient to reduce serum PTH by at least 20% for at least 10 hours post-administration of the calcium modulator peptide. In certain embodiments, the decrease in PTH level is determined as the reduction in serum intact PTH. In other embodiments, the therapeutically effective amount of the calcium modulator peptide is sufficient to reduce serum intact PTH by at least 20% below pre-treatment baseline levels for at least 10 hours post-administration of the calcium modulator peptide.

In other embodiments, the therapeutically effective amount of the calcium modulator peptide is sufficient to reduce serum PTH by 30% to 70% for at least 48 hours post-administration of the calcium modulator peptide.

In certain embodiments, the therapeutically effective amount of the calcium modulator peptide is sufficient to reduce serum calcium by at least 5% for at least 10 hours post-administration of the calcium modulator peptide.

In other embodiments, the therapeutically effective amount of the calcium modulator peptide is sufficient to reduce serum calcium by 5% to 20% for at least 48 hours post-administration of the calcium modulator peptide.

The methods of the present invention are useful to treat subjects afflicted with disorders or diseases characterized by elevated levels of serum PTH, elevated levels of serum calcium, or both. In some embodiments, the methods of the present invention may also be useful to treat subjects afflicted with disorders or diseases characterized by decreased levels of serum phosphate.

In some embodiments, the subject is human. In other embodiments, the subject is human and serum PTH is reduced. In certain embodiments, the subject is human and serum calcium is reduced. In further embodiments, the subject is human and bone turnover is reduced.

In some embodiments, the subject is afflicted with primary hyperparathyroidism, secondary hyperparathyroidism, tertiary hyperparathyroidism, hypercalcemia of malignancy, metastatic bone disease (e.g., osteosarcoma), Paget's disease, osteoarthritis, rheumatoid arthritis, osteomalacia, chondrocalcinosis, achondroplasia, osteochondritis, osteogenesis imperfecta, congenital hypophosphatasia, fibromatous lesions, fibrous dysplasia, multiple myeloma, osteolytic bone disease, periprosthetic osteolysis, periodontal disease, osteoporosis, abnormal bone turnover, or high turnover bone disease.

In specific embodiments, the subject is afflicted with primary, secondary or tertiary hyperparathyroidism. In preferred embodiments, the subject is afflicted with secondary hyperparathyroidism (sometimes referred to as SHPT). Reductions of serum PTH in subjects afflicted with SHPT would be expected to reduce bone turnover. In other embodiments, the subject is afflicted with hypercalcemia of malignancy or metastatic bone disease (e.g., osteocarcoma). In further embodiments, the subject is afflicted with osteoporosis.

In one aspect, the invention provides a calcium modulator peptide comprising:
a) a polycationic peptide comprising 5 to 20 amino acids which are positively charged at physiological pH, an amino terminus, a carboxy terminus, and a first thiol-containing residue;
wherein the polycationic peptide is chemically modified at the amino terminus, the carboxy terminus, or both; and
b) a cargo peptide comprising a second thiol-containing residue;
wherein the second thiol-containing residue is disulfide bonded to the first thiol-containing residue.

In another aspect, the invention provides a calcium modulator peptide comprising:
a) a first polycationic peptide comprising at least 3 amino acids which are positively charged at physiological pH, a first amino terminus, a first carboxy terminus, and a first thiol-containing residue;
wherein the first polycationic peptide is chemically modified at the first amino terminus, the first carboxy terminus, or both; and
b) a second polycationic peptide comprising at least 3 amino acids which are positively charged at physiological pH, a second amino terminus, a second carboxy terminus, and a second thiol-containing residue;
wherein the second polycationic peptide is chemically modified at the second amino terminus, the second carboxy terminus, or both;
wherein the calcium modulator peptide comprises 6 to 30 amino acids which are positively charged at physiological pH.

In a further aspect, the invention provides a calcium modulator peptide comprising:
a polycationic peptide comprising 5 to 20 amino acids which are positively charged at physiological pH, an amino terminus, a carboxy terminus, and a first thiol-containing residue;
wherein the polycationic peptide is chemically modified at the amino terminus, the carboxy terminus, or both; and
wherein the first thiol-containing residue contains a thiol group which may be present as a free thiol or in a protected form.

In some such embodiments, the polycationic peptide further comprises a second thiol-containing residue which is disulfide bonded to the first thiol-containing residue. In such cases, formation of a disulfide bond forms a cyclic polycationic calcium modulator peptide.

In another aspect, the present invention provides a calcium modulating peptide as described herein conjugated to polyethylene glycol (PEG) to form a PEGylated peptide. In preferred embodiments, the PEG has an average molecular weight of from about 5 kDa to about 40 kDa.

In a further aspect, the invention provides pharmaceutical compositions comprising a calcium modulating peptide as further described herein and one or more pharmaceutically acceptable excipients.

Peptides useful in the methods of the present invention can be chemically synthesized using conventional solution-phase or solid-phase techniques, or may be recombinantly produced. Pharmaceutical compositions comprising at least one pharmaceutically acceptable excipient and the peptides described are also contemplated for use with the methods provided herein.

The methods of the present invention may be useful for the treatment of hyperparathyroidism, bone disease, and other hypercalcemic disorders. Exemplary diseases include but are not limited to: hyperparathyroidism (primary, secondary and tertiary), hypercalcemia of malignancy, metastatic bone disease, Paget's disease, osteoarthritis, rheumatoid arthritis, osteomalacia, chondrocalcinosis, achondroplasia, osteochondritis, osteogenesis imperfecta, congenital hypophosphatasia, fibromatous lesions, fibrous dysplasia, multiple myeloma, osteolytic bone disease, periprosthetic osteolysis, periodontal disease, osteoporosis, abnormal bone turnover, and other forms of high turnover bone disease.

BRIEF DESCRIPTION OF THE DRAWINGS

FIG. 1 shows the relationship between PTH, serum calcium and serum phosphate (iP) levels in dogs given KAI-1455 at 12.5 mg/kg by 12-hour intravenous infusion.

FIG. 2 shows serum calcium levels in dogs given KAI-1455 at a dose of 25 mg/kg by intravenous infusion over 12 hours, with calcium supplementation (2 mg elemental calcium/kg/hr) during the 12-hour infusion and again from hours 3-6 post-EOI.

FIG. 3 shows serum phosphate levels in dogs given KAI-1455 at a dose of 25 mg/kg by intravenous infusion over 12 hours, with calcium supplementation (2 mg elemental calcium/kg/hr) during the 12-hour infusion and again from hours 3-6 post-EOI.

FIG. 4 shows plasma pharmacokinetics of KAI-1455 in human plasma in subjects administered KAI-1455 at doses of 18, 54, 81 and 162 mg/kg/hr by intravenous infusion over 12 hours. The concentration of KAI-1455 (ng/mL) was determined pre-dose and at 1, 3, 6, 9, 12 hour timepoints during dosing, and at 2, 5, 7, 10, 15, 20, 30 and 60 minutes following the end of infusion.

FIG. 5 shows ionized calcium (mmol/L) at the start of infusion, and at 3, 6, 9, 12, 15, 18, 21, 24 and 48 hours after the start of infusion in humans administered KAI-1455 at doses of 18, 54, 81 and 162 mg/kg by intravenous infusion over 12 hours.

FIG. 6 shows total calcium (mg/dL) at the start of infusion, and at 3, 6, 9, 12, 15, 18, 21, 24 and 48 hours after the start of infusion in humans administered KAI-1455 at doses of 18, 54, 81 and 162 mg/kg by intravenous infusion over 12 hours FIG. 7 shows the percent change in calcium levels at the start of infusion, and at 3, 6, 9, 12, 15, 18, 21, 24 and 48 hours after the start of infusion in humans administered KAI-1455 at doses of 18, 54, 81 and 162 mg/kg by intravenous infusion over 12 hours FIG. 8 shows plasma PTH level (pg/mL) at the start of infusion, and at 3, 6, 12, 15, 18, 24 and 48 hours after the start of infusion in humans administered KAI-1455 at doses of 18, 54, 81 and 162 mg/kg by intravenous infusion over 12 hours FIG. 9 shows the percent change in plasma PTH levels at the start of infusion, and at 3, 6, 12, 15, 18, 24 and 48 hours after the start of infusion in humans administered KAI-1455 at doses of 18, 54, 81 and 162 mg/kg by intravenous infusion over 12 hours FIG. 10 shows ionized calcium (mmol/L) at the start of infusion, and at 2, 3, 4, 6, 8, 12, 16 and 36 hours after the start of infusion in humans administered KAI-1455 at doses of 54 and 108 mg/kg by intravenous infusion over 4 hours.

FIG. 11 shows total calcium (mg/dL) at the start of infusion, and at 2, 3, 4, 6, 8, 12, 16 and 36 hours after the start of infusion in humans administered KAI-1455 at doses of 54 and 108 mg/kg/hr by intravenous infusion over 4 hours.

FIG. 12 shows plasma PTH level (pg/mL) at the start of infusion, and at 2, 3, 4, 6, 8, 12, 16 and 36 hours after the start of infusion in humans administered KAI-1455 at doses of 54 and 108 mg/kg/hr by intravenous infusion over 4 hours.

FIG. 13 shows total calcium (mg/dL) and plasma PTH (pg/mL) preinfusion, and at 1, 2, 3 and 4 hour timepoints in anesthetized rats (n=4) administered KP-1524 (SEQ ID NO:9) at a dose rate of 9 mg/kg/hr by intravenous infusion for 3 hours.

FIG. 14 shows total calcium (mg/dL) levels predose and at 1, 2, 3, 4 and 24 hour timepoints in anesthetized rats (n=4) administered KP-9706 (SEQ ID NO:6) at a dose rate of 9 mg/kg/hr by intravenous infusion for 3 hours.

FIG. 15 shows in vitro plasma stability data in rat EDTA plasma for KAI-1455 (SEQ ID NO:7), KP-9706 (SEQ ID NO:6) and KP-9803 (SEQ ID NO:8).

DETAILED DESCRIPTION OF THE INVENTION

The current invention relates to methods of using polycationic peptides to prevent, treat or ameliorate hyperparathyroidism, bone disease and/or other hypercalcemic disorders.

As used herein, the term "hyperparathyroidism" refers to primary, secondary and tertiary hyperparathyroidism, unless otherwise indicated. In a preferred embodiment, a subject having secondary hyperparathyroidism is treated using the calcium modulator peptides of the invention to reduce plasma PTH levels. Untreated SHPT patients with moderately severe hyperparathyroidism often have baseline circulating Intact PTH levels >300 pg/ml, and levels than exceed 600 pg/mL. In a preferred embodiment, the decrease in serum PTH is measured as a decrease in Intact PTH below pretreatment baseline levels.

As used herein, a "calcium modulator peptide" is a peptide comprising one or more polycationic peptides and a total of 3 to 30 amino acids which are positively charged at physiological pH, wherein the positively charged amino acids are contained within the polycationic peptides, and wherein the calcium modulator peptide is capable of decreasing serum PTH and/or calcium levels in a target tissue or tissues, or in a subject. In certain embodiments, the calcium modulator peptide is capable of decreasing serum PTH and/or serum calcium levels when a therapeutically effective amount of the calcium modulator peptide is administered to a subject in need of such treatment. In preferred embodiments, the calcium modulator peptide comprises 5 to 20 amino acids which are positively charged at physiological pH. In particularly preferred embodiments, the calcium modulator peptide comprises 6 to 12 amino acids which are positively charged at physiological pH. The calcium modulator peptides of the present invention comprise a total of about 4 to 35 amino acid residues, including the positively charged amino acid residues.

In certain embodiments, the calcium modulator peptide of the present invention comprises a polycationic peptide and a cargo peptide, each comprising a thiol-containing residue, wherein the thiol-containing residues are linked by a disulfide bond.

In other embodiments, the calcium modulator peptide comprises two polycationic peptides, each comprising a thiol-containing residue, linked by a disulfide bond. In some such embodiments, the first polycationic peptide and the second polycationic peptide are the same, such that formation of a disulfide bond forms a homodimeric structure. In other embodiments, the first polycationic peptide and the second polycationic peptide are different, such that formation of a disulfide bond forms a heterodimeric structure.

In further embodiments, the calcium modulator peptide comprises a single polycationic peptide and at least one thiol-containing residue, wherein the thiol-containing residue contains a free thiol or the thiol moiety is present in a protected form. In some such embodiments, the calcium modulator peptide comprises a single polycationic peptide and two thiol-containing residues which are disulfide bonded to each other, (i.e., the thiol moieties are internally "protected" as a disulfide group), wherein disulfide bond formation provides a cyclic calcium modulator peptide.

As used herein, a "polycationic peptide" refers to a peptide comprising 2 to 30 amino acids which are positively charged at physiological pH, and at least one thiol-containing residue, wherein the polycationic peptide is chemically modified (i.e., "capped") at the peptide's amino terminus, carboxy terminus, or both.

Polycationic peptides can vary in length from 3 to 35 amino acid residues in total, preferably from 5 to 25 amino acid residues in total, and may consist of a single repeating positively charged amino acid residue or may comprise a variety of natural or unnatural amino acid residues. In preferred embodiments, the polycationic peptide comprises from 5 to 20 positively charged amino acids, preferably 5 to 15 positively charged amino acids, more preferably comprises 6 to 12 positively charged amino acids.

In some embodiments, the calcium modulating peptide comprises only one polycationic peptide. In other embodiments, the calcium modulating peptide comprises two polycationic peptides, each of which preferably comprises 3 to 10 positively charged amino acids.

Preferred polycationic peptides include TAT-derived peptides, for example the capped Cys-TAT peptide having the sequence of SEQ ID NO:5 or a truncated peptide having the sequence of SEQ ID NO:29. Also preferred are polycationic peptides comprising 3 to 7 arginine residues. In some embodiments, the arginine residues are sequential, such as the capped polyarginine peptides having the sequences of SEQ ID NOs: 19-26. In other embodiments, the polycationic peptide may comprise 3 to 7 arginine residues which are non-sequential, such as the peptide having SEQ ID NO:32.

As used herein, the term "positively charged amino acids" refers to amino acid residues which are positively charged at physiological pH (~7.4 in plasma).

Positively charged amino acids are independently selected from natural or unnatural amino acids which are positively charged at physiological pH, having either the L- or D-configuration, or racemates thereof, or mixtures thereof having any degree of chiral purity. In some embodiments, the positively charged amino acids are selected from natural amino acids. In other embodiments, the positively charged amino acids are selected from natural and/or unnatural amino acids. In specific embodiments, the positively charged amino acids are independently selected from the group consisting of histidine, lysine, arginine, 2,3-diaminopropionic acid (Dap), 2,4-diaminobutyric acid (Dab), ornithine, and homoarginine.

Once a therapeutic peptide enters the plasma of a subject, it become vulnerable to attack by peptidases. Exopeptidases are typically non-specific enzymes which cleave amino acid residues from the amino or carboxy termini of a peptide or protein. Endopeptidases, which cleave within an amino acid sequence, can also be non-specific; however endopeptidases frequently recognize particular amino sequences (recognition sites) and cleaves the peptide at or near those sites.

One method of protecting peptide compositions from proteolytic degradation involves "chemically modifying" or "capping" the amino and/or carboxy termini of the peptides. As used herein, the terms "chemically modified" or "capped" are used interchangeably to refer to the introduction of a blocking group to the terminus of the peptide via a covalent modification. Suitable blocking groups serve to cap the termini of the peptides without decreasing the biological activity of the peptides.

Without wishing to be bound by theory, it is believed that capping of at least one termini of the polycationic peptide is important for obtaining sufficient plasma stability and exposure to achieve therapeutically relevant levels of PTH and/or calcium reductions in vivo. Such blocking or "capping" groups may be useful to protect the peptides from proteolytic degradation by serum proteases.

Acetylation of the amino termini of the described peptides is a preferred method of protecting the peptides from proteolytic degradation. Amidation of the carboxy termini of the described peptides is also a preferred method of protecting the peptides from proteolytic degradation. However, other capping groups are possible. For example, the amino terminus may be capped by acylation or sulfonylation, to form amides or sulfonamides. Similarly, the carboxy terminus may be esterified, or converted to a secondary amide, and acyl sulfonamide, or the like. In some embodiments, the amino terminus or the carboxy terminus may comprise the site of PEGylation, i.e., the amino or carboxy termini may be chemically modified by reaction with a suitably functionalized PEG.

Protecting peptides from endopeptidases typically involves identification and elimination of an endopeptidase recognition site from a peptide. Protease recognition sites are well known to those of ordinary skill in the art. Thus it is possible to identify a potential endoprotease recognition site and then eliminating that site by altering the amino acid sequence within the recognition site. Residues in the recognition sequence can be moved or removed to destroy the recognition site. Preferably, a conservative substitution is made with one or more of the amino acids which comprise an identified protease recognition site.

In preferred embodiments, the amino terminus of the polycationic peptide(s) is chemically modified by acetylation, to provide an N-acetyl peptide. In further preferred embodiments, the carboxy terminus of the polycationic peptide(s) is chemically modified by amidation to provide a primary carboxamide at the C-terminus. In a particularly preferred embodiments, both the amino terminus and carboxy terminus are capped by acetylation and amidation, respectively.

As used herein, the term "thiol-containing residue" refers to a thiol-containing amino acid or a thiol-containing compound comprising an amino group and/or a carboxy group such that it can be incorporated into a polypeptide, wherein the thiol group may be in protected or unprotected form, and which is capable of forming a disulfide bond when the thiol group is in its free form.

Representative examples of thiol-containing residues include, e.g., cysteine, homocysteine, and mercaptopropionic acid. When the thiol-containing residue contains a chiral center, it may be present in the L- or D-configuration, or as a racemate, or in any degree of chiral purity. In frequent embodiments, the thiol-containing residue(s) comprise cysteine or homocysteine.

The thiol-containing residue may be located at any position along the polycationic peptide chain, including the amino terminus, the carboxy terminus, or some other position. For ease of chemical synthesis, thiol-containing residues are frequently coupled to the peptide chain using a building block containing the thiol moiety in a protected form.

In some embodiments, the thiol-containing residues which form a disulfide bond between the polycationic peptide and the cargo peptide, or between the first and second polycationic peptides, are the same (i.e., cysteine to cysteine, or homocysteine to homocysteine). In other embodiments, the two thiol-containing residues may be different.

In certain embodiments, the thiol-containing amino acid may be in a protected form. Suitable protecting groups for thiol moieties include, for example, thioester derivatives, in particular thioacetyl or thiobenzoyl analogs; thiocarbonates; hemithioacetals, such as 1-ethoxyethyl, methoxymethyl and polyoxymethylene thioethers; and disulfide protecting groups, such as the disulfide formed between the free thiol of a thiol-containing residue and a substituted or unsubstituted thiophenol moiety.

In some embodiments, the thiol protecting group may be cleavable in vivo. Such protected thiol-containing residues may function as prodrugs, masking the free thiol and modifying the physicochemical, pharmacokinetic and/or pharmacodynamic properties of the calcium modulator peptide comprising such a protected thiol-containing residue.

The joining thiol-containing residues can be placed anywhere in the sequence of the polycationic peptide(s) and/or the cargo peptides. For example, the first and second thiol-containing residues may be located at the amino termini of the two polycationic peptides in certain embodiments, or at the amino termini of the polycationic peptide and the cargo peptide in other embodiments. The joining thiol-containing residues can be placed at the carboxy termini of the peptides, or alternatively at the amino terminus of one of the polycationic and cargo peptide, and at the carboxy terminus of the other peptide. Additionally, the joining thiol-containing residues can be placed anywhere within the sequence of either or both of the polycationic peptides and/or the cargo peptide.

In some embodiments, the first thiol-containing residue is located at the amino terminus or the carboxy terminus of the first polycationic or polycationic peptide. In other embodiments, the first thiol-containing residue is located at a position other than the amino terminus or the carboxy terminus of the first polycationic or polycationic peptide. In some embodiments, the second thiol-containing residue is located at the amino terminus or the carboxy terminus of the second polycationic or cargo peptide. In other embodiments, the second thiol-containing residue is located at a position other than the amino terminus or the carboxy terminus of the second polycationic or cargo peptide.

In a preferred embodiment, the first and second thiol-containing residues are both cysteine residues. In other embodiments, homocysteine analogs can also be used to form a disulfide linkage between two polycationic peptides or between a polycationic and cargo peptide. For example, the use of homocysteine in the cargo, the polycationic peptide, or both may be used, and may stabilize the composition and decrease disulfide bond exchange. Other cysteine homologs are also useful for disulfide bond formation. Similarly, stereoisomers of cysteine and homocysteine will inhibit disulfide bond exchange.

In some embodiments, the second thiol-containing residue is another residue in the polycationic peptide, such that formation of a disulfide bond between the first and second thiol-containing residues forms a cyclic polycationic peptide.

As used herein, the term "cargo peptide" refers to a 5-25 amino acid peptide, comprising a second thiol-containing residue. In frequent embodiments, the cargo peptide is covalently linked to the polycationic peptide through formation of an intermolecular disulfide bond between the first and second thiol-containing residues. In some instances, the cargo peptide may contain positively charged amino acid residues. However, the presence of positively charged amino acid residues is not a required feature of a cargo peptide. In certain embodiments, the cargo peptide comprises an isozyme specific PKC modulator peptide.

As used herein, a compound is "isozyme-specific" when it acts on a particular PKC isozyme involved in bone remodeling and/or calcium homeostasis, as opposed to non-specific peptides or compounds that fail to discriminate between PKC isozymes.

As used herein, a "PKC modulator peptide" is defined as a compound capable of activating or inhibiting the activity of a PKC isozyme, either in full or in part, in a target tissue or tissues. A PKC modulator peptide may demonstrate different isozyme specificity, activator or inhibitor activity and/or levels of activator or inhibitor activity (full or part) in different tissues.

In some embodiments, the cargo peptide is a PKC modulator peptide, wherein said PKC modulator peptide comprises an amino acid sequence that comprises greater than 50% sequence identity with a peptide selected from the group consisting of SEQ ID NOs: 1 and 2. In other methods, the PKC modulator peptide comprises an amino acid sequence that comprises between 5 to 9 consecutive residues of a peptide selected from the group consisting of SEQ ID NOs:1 and 2. In certain methods, the PKC modulator peptide comprises an amino acid sequence selected from the group consisting of SEQ ID NOs:1 and 2. In other embodiments, the cargo peptide is a PKC modulator peptide, wherein said PKC modulator peptide comprises an amino acid sequence that comprises greater than 50% sequence identity with a peptide known to have PKC modulating activity.

In other embodiments, the calcium modulator peptide of the present invention comprises an amino acid sequence that comprises greater than 50% sequence identity with a peptide selected from the group consisting of SEQ ID NOs:6, 7, 8, 9, 10, 12, 13, 14, 15, 16, 17, 18, 19, 20, 21, 22, 23, 24, 25, 26, 28, 28, 31, and 32. In further embodiments, the calcium modulator peptide comprises an amino acid sequence that comprises between 6 to 15 consecutive residues of a peptide selected from the group consisting of SEQ ID NOs:6, 7, 8, 9, 10, 12, 13, 14, 15, 16, 17, 18, 19, 20, 21, 22, 23, 24, 25, 26, 28, 28, 31, and 32. In certain methods, the calcium modulator peptide comprises an amino acid sequence selected from the group consisting of SEQ ID NOs: 7, 9, 10, and 12.

In specific embodiments, the calcium modulator peptide comprises a polycationic peptide disulfide bonded to a cargo peptide, as further described herein. In preferred embodiments, the calcium modulator peptide is selected from the peptides having the sequence of SEQ ID NO:7, SEQ ID NO:9, SEQ ID NO:10, or SEQ ID NO:12.

In other embodiments, the calcium modulator peptide comprises a first polycationic peptide disulfide bonded to a second polycationic peptide, as further described herein. In preferred embodiments, the calcium modulator peptide is selected from the peptides having the sequence of SEQ ID NO:13, SEQ ID NO:15, SEQ ID NO:16, SEQ ID NO:17, SEQ ID NO:18.

In other embodiments, the calcium modulator peptide comprises a single polycationic peptide comprising a first thiol-containing residue, wherein the thiol group is present in protected or unprotected form, as further described herein. In some such embodiments, the calcium modulator peptide further comprises a second thiol-containing residue, such that formation of a disulfide bond forms a cyclic peptide. In preferred embodiments, the calcium modulator peptide is selected from the peptides having the sequence of SEQ ID NO:5, SEQ ID NO:14, SEQ ID NOs:19 to 26, SEQ ID NO:29, or SEQ ID NO:32.

KAI-1455 (SEQ ID NO:7) comprises an isozyme-specific PKC modulator peptide as the cargo peptide. Calcium modulating peptides comprising other cargo peptides, e.g., KP-1524 (SEQ ID NO: 9), also significantly decreased total calcium and PTH levels in rats, at levels comparable to KAI-1455 (Examples 11 and 12). Without wishing to be bound by theory, it is possible that the disulfide linkage to the cargo peptide acts as a prodrug to protect the polycationic peptide in vivo, prolonging its duration of action in plasma. Without wishing to be bound by theory, it is possible that the cargo peptide may provide a prodrug form that enhances or stabilizes the calcium and PTH modulation activity Calcium modulating peptides of the present invention comprise at least one thiol-containing residue, wherein the thiol group may be present as a free thiol, a protected thiol or may be disulfide bonded to as second thiol-containing residue. In frequent embodiments, the calcium modulating peptides comprises at least two thiol-containing residues which are disulfide bonded to each other.

Calcium modulating peptides comprising a single thiol-containing residue having a free thiol group demonstrated activity in vitro at levels comparable to that shown for KAI- 1455. For example, a capped TAT-derived peptide having an N-terminal cysteine residue containing a free thiol (SEQ ID NO:5) demonstrated activity comparable to KAI-1455 when tested in vitro.

Calcium modulating peptides comprising a single thiol-containing residue having a free thiol group may themselves be useful in methods of the invention, or the thiol group may be administered as a prodrug, by protecting the free thiol group as further described herein within a protecting group that is cleavable in vivo. Such groups are known in the art for the protection of thiol containing therapeutic agents.

In another aspect, the invention provides a pharmaceutical composition comprising a polycationic peptide (as further described herein) and at least one pharmaceutically acceptable excipient.

In another aspect, the invention provides methods for treating hyperparathyroidism, hypercalcemia and/or bone disease comprising administering a therapeutically effective amount of a calcium modulator peptide as described herein, and further comprising treating the subject with a therapeutically effective amount of an agent selected from the group consisting of antiresorptive bisphosphonate agents, integrin blockers, hormone replacement therapeutic agents, selective estrogen receptor modulators, cathepsin K inhibitors, vitamin D therapy, anti-inflammatory agents, low dose PTH therapy, calcitonin, inhibitors of RANK ligand, antibodies against RANK ligand, osteoprotegrin, adensosine antagonists and ATP proton pump inhibitors.

In another aspect of the invention, the calcium modulator peptide is administered in an amount effective to decrease serum PTH or PTH effect.

In some embodiments, the reduction in serum PTH is at least 1%, 2%, 3%, 4%, 5%, 6%, 7%, 8%, 9%, 10%, 11%, 12%, 13%, 14%, 15%, 16%, 17%, 18%, 19%, 20%, 25% or 30% below baseline pretreatment levels for at least 10 hours post administration of the calcium modulator peptide. In specific embodiments, the reduction in serum PTH is at least 20% at 10 hours post administration. In preferred embodiments, the reduction in serum PTH is 15 to 40%, preferably 20 to 50%, more preferably 30 to 70% below baseline pretreatment levels for at least 48 hours post administration of the calcium modulator peptide.

In another aspect of the invention, the calcium modulator peptide is administered in an amount effective to decrease serum calcium or calcium effect.

In some embodiments, the reduction in serum calcium is at least 1%, 2%, 3%, 4%, 5%, 6%, 7%, 8%, 9%, 10%, 11%, 12%, 13%, 14%, 15%, 16%, 17%, 18%, 19%, 20% or 25% below baseline pretreatment levels for at least 10 hours post administration of the calcium modulator peptide. In preferred embodiments, the reduction in serum calcium is at least 5% at 10 hours post administration. In preferred embodiments, the reduction is serum calcium is 5 to 10%, preferably 5 to 20% below baseline pretreatment levels for at least 48 hours post administration of the calcium modulator peptide.

In another aspect, the invention provides a method for treating hyperparathyroidism and/or hypercalcemia in a subject in need thereof, comprising: administering a therapeutically effective amount of a polycationic peptide comprising an amino acid sequence comprising greater than 50% sequence identity with a peptide selected from the group consisting of SEQ ID NO:7, SEQ ID NO:9, SEQ ID NO:10, or SEQ ID NO:12, whereby serum PTH and/or calcium is reduced.

Within this application, unless otherwise stated, definitions of the terms and illustration of the techniques of this application may be found in any of several well-known references such as: Sambrook, J., et al., Molecular Cloning: A Laboratory Manual, Cold Spring Harbor Laboratory Press (1989); Goeddel, D., ed., Gene Expression Technology, Methods in Enzymology, 185, Academic Press, San Diego, Calif. (1991); "Guide to Protein Purification" in Deutshcer, M. P., ed., Methods in Enzymology, Academic Press, San Diego, Calif. (1989); Innis, et al., PCR Protocols: A Guide to Methods and Applications, Academic Press, San Diego, Calif. (1990); Freshney, R. I., Culture of Animal Cells: A Manual of Basic Technique, 2nd Ed., Alan Liss, Inc. New York, N.Y. (1987); Murray, E. J., ed., Gene Transfer and Expression Protocols, pp. 109-128, The Humana Press Inc., Clifton, N.J. and Lewin, B., Genes VI, Oxford University Press, New York (1997).

The present invention may be understood more readily by reference to the following detailed description of the preferred embodiments of the invention and the Examples included herein. However, before the present methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. It is further to be understood that unless specifically defined herein, the terminology used herein is to be given its traditional meaning as known in the relative art.

As used herein, the singular form "a", "an", and "the" include plural references unless indicated otherwise. For example, "a" modulator peptide includes one of more modulator peptides.

As used herein, a "therapeutically effective amount" is an amount required to produce a desired therapeutic effect. For example, in methods for reducing serum calcium in hypercalcemic subjects, a therapeutically effective amount is the amount required to reduce serum calcium levels by at least 1%, 2%, 3%, 4%, 5%, 6%, 7%, 8%, 9%, 10%, 11%, 12%, 13%, 14%, 15%, 16%, 17%, 18%, 19%, 20% or 25%.

As used herein, "subject" refers to a human or animal subject having hypercalcemia and/or bone disease.

As used herein, "peptide" and "polypeptide" are used interchangeably and refer to a compound made up of a chain of amino acid residues linked by peptide bonds. Unless otherwise indicated, the sequence for peptides is given in the order from the amino terminus to the carboxyl terminus.

To determine the percent homology of two amino acid sequences, the sequences are aligned for optimal comparison purposes (e.g., gaps can be introduced in the sequence of one polypeptide for optimal alignment with the other polypeptide). The amino acid residues at corresponding amino acid positions are then compared. When a position in one sequence is occupied by the same amino acid residue as the corresponding position in the other sequence, then the molecules are identical at that position. As used herein amino acid or nucleic acid "homology" is equivalent to amino acid or nucleic acid "identity". Accordingly, the percent sequence identity between the two sequences is a function of the number of identical positions shared by the sequences (i.e., percent sequence identity=numbers of identical positions/total numbers of positions×100).

For the purposes of the invention, the percent sequence identity between two polypeptide sequences is determined using the Vector NTI 6.0 (PC) software package (InforMax, 7600 Wisconsin Ave., Bethesda, Md. 20814). A gap opening penalty of 10 and a gap extension penalty of 0.1 are used for determining the percent identity of two polypeptides. All other parameters are set at the default settings.

A peptide or peptide fragment is "derived from" a parent peptide or polypeptide if it has an amino acid sequence that is identical or homologous to at least a contiguous sequence of five amino acid residues of the parent peptide or polypeptide.

As used herein, "conservative amino acid substitutions" are substitutions which do not result in a significant change in the activity or tertiary structure of a selected polypeptide or protein. Such substitutions typically involve replacing a selected amino acid residue with a different residue having similar physico-chemical properties. Groupings of amino acids by physico-chemical properties are known to those of skill in the art. For example, families of amino acid residues having similar side chains have been defined in the art, and include basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Another aspect of the invention pertains to the use of isolated polypeptides, and biologically active portions thereof. As used herein, an "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of polypeptides in which the polypeptide is separated from some of the cellular components of the cells in which it is naturally or recombinantly produced.

When the polypeptide or biologically active portion thereof is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of polypeptides in which the polypeptide is separated from chemical precursors or other chemicals that are involved in the synthesis of the polypeptide. In one embodiment, the language "substantially free of chemical precursors or other chemicals" includes preparations of a polypeptide having less than about 30% (by dry weight) of chemical precursors or other chemicals, more preferably less than about 20% chemical precursors or other chemicals, still more preferably less than about 10% chemical precursors or other chemicals, and most preferably less than about 5% chemical precursors or other chemicals. In preferred embodiments, isolated polypeptides, or biologically active portions thereof, lack contaminating polypeptides from the same organism from which the domain polypeptide is derived.

Non-limiting methods for conjugating the polycationic peptide to the cargo peptide include conjugation via a disulfide bond, and synthesis as a single chain or linear polypeptide. The polycationic peptide can also be conjugated to the cargo peptide via a linker. In some embodiments, the linker is a 1-5 amino acid peptide, a 2-4 amino acid peptide, or a 2-3 amino acid peptide.

Peptide Modulators of PKC Isozymes

A variety of peptide modulators of PKC isozymes have been previously described. For example, U.S. Pat. No. 5,783,405 describes a number of peptides which modulate the activity of PKC isozymes, including the beta, theta, delta, epsilon, and gamma isozymes. Pending U.S. patent application Ser. No. 10/843,271 describes delta PKC modulator peptides and derivatives thereof. U.S. Pat. No. 6,165,977 describes epsilon PKC modulation peptides and derivatives thereof. U.S. Pat. No. 6,855,693 describes a variety of modulator peptides and modified fragments from the $\alpha$, $\beta_I$, $\beta_{II}$, $\gamma$, $\delta$, $\epsilon$, $\eta$, $\mu$, $\Theta$, and $\zeta$ isozymes. Each patent and patent application is hereby incorporated by reference in their entirety.

PKC isozyme-specific inhibitor peptides may be derived from specific RACK-binding sites located in the C2/V1 domain of the particular isozyme. Isozyme-specific peptide modulators may be derived from a pseudoRACK ($\psi$RACK) sequence in each PKC isozyme that is similar to a sequence in the corresponding RACK. The $\psi$RACK sequences are believed to form intramolecular interactions with the RACK binding site of the PKC, stabilizing the inactive or "closed" conformation. Peptides which interfere with this intramolecular interaction can destabilize the inactive form, enhancing PKC translocation and RACK binding. Chen et al. *Proc. Nat. Acad. Sci.* 2001; 98:11114-11119.

Isozyme-specific peptide modulators can be conjugated to a carrier moiety that is effective to facilitate transport of the peptides across a cell membrane. Examples of the carrier moiety include, but are not limited to, a TAT-derived peptide, an Antennapedia carrier peptide, and a polyarginine peptide. TAT-conjugated peptides have been reported to be effectively delivered into organs via the circulation, and this mode of delivery may offer advantages over gene targeted delivery, because delivery is immediate and therefore less susceptible to adaptations induced by the signal transduction modulator.

$\Psi\epsilon$RACK, comprising the amino acid sequence HDAPIGYD (SEQ ID NO:1), is an isozyme-selective peptide was designed to bind to and 'stabilize' $\epsilon$PKC in a conformation that exposes the RACK binding site, thereby enabling the binding of $\epsilon$PKC to its RACK. $\psi\epsilon$RACK differs from small molecule activators of PKC (such as diacylglycerol (DAG) or phorbol esters) in several important ways. First, $\psi\epsilon$RACK binds to a different site on $\epsilon$PKC compared to DAG or phorbol esters. Second, $\psi\epsilon$RACK only binds to a site in the $\epsilon$PKC isoform that is unique to that isoform, whereas DAG and phorbol esters bind to a site that is common to all PKCs. This specificity of $\psi\epsilon$RACK confers a significant advantage over non-selective molecules. Finally, $\psi\epsilon$RACK treatment results in modest physiologic shifts in $\epsilon$PKC translocation even when administered for prolonged periods. These data suggest that $\psi\epsilon$RACK potentiates the activity of $\epsilon$PKC but does not directly activate PKC the way PKC is activated by DAG.

Translocation of $\epsilon$PKC has been reported to play a key role in ischemic preconditioning. $\psi\epsilon$RACK (SEQ ID NO:1) demonstrated a cardioprotective effect against ischemia-reperfusion injury in vivo and ex vivo, and reduced the incidence of lethal arrhythmia during ischemia-reperfusion without causing desensitization or downregulation of $\epsilon$PKC.

$\epsilon$PKC has also been reported to play a role in regulating the activation of nervous, endocrine, exocrine, inflammatory, and immune systems. The controlled activation of $\epsilon$PKC may play a protective role in the development of Alzheimer's disease, whereas its uncontrolled chronic activation may result in severe diseases such as malignant tumors and diabetes.

To facilitate transfer across biological membranes, a $\psi\epsilon$RACK peptide containing an N-terminal cysteine, comprising amino acid sequence CHDAPIGYD (SEQ ID NO:2), may be covalently linked to a polycationic peptide.

Epsilon-PKC modulator peptide (SEQ ID NO:6), comprising the peptide of SEQ ID NO:2 conjugated via a disulfide bond to TAT (SEQ ID NO:4), and calcium modulator peptide (SEQ ID NO:7), comprising the peptide of SEQ ID NO:2 conjugated via a disulfide bond to N-acylated C-amidated TAT (SEQ ID NO:5), were prepared. The peptide comprising SEQ ID NO:7, also referred to as KAI-1455 (or KP-1455) herein, has the structure shown below.

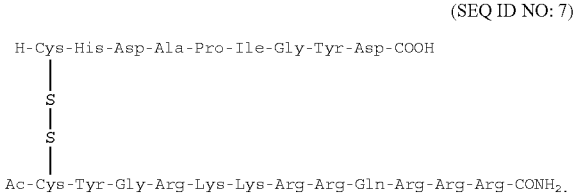

(SEQ ID NO: 7)

```
H-Cys-His-Asp-Ala-Pro-Ile-Gly-Tyr-Asp-COOH
   |
   S
   |
   S
   |
Ac-Cys-Tyr-Gly-Arg-Lys-Lys-Arg-Arg-Gln-Arg-Arg-Arg-CONH₂.
```

It has surprisingly been found that KAI-1455 (SEQ ID NO:7) caused a significant reduction in serum calcium levels in high dose animal toxicology studies. A decrease in serum calcium levels following intravenous infusion of KAI-1455 was observed in three species (rats, dogs and human subjects in clinical setting). The calcium nadir appears to occur at the end of infusion, while calcium suppression may last for more than 24 hours after the end of infusion. The effects on serum calcium are dose dependent and reversible.

In a single escalating-dose study of KAI-1455 (SEQ ID NO:7) administered by 12 hour infusion to male volunteers, significant reductions in ionized and total calcium were observed, with maximal reductions around the EOI. A maximal percent-change in calcium of greater than 15% was observed at the highest concentration (162 mg/kg over 12 hours). During the same study, a dose dependent reduction in plasma PTH level (pg/mL) was observed, with the maximal reductions observed at the EOI. A significant decrease in PTH was observed at the EOI and at 12 hours post-EOI for subjects in the highest dose group (162 mg/kg over 12 hours), with sustained decreases below pretreatment baseline levels still observable 36 hours post-EOI. A maximal percent decrease in plasma PTH level of greater than 40% was observed for subjects in the 81 and 162 mg/kg dose groups, with levels still significantly below baseline 12 hours post-EOI.

No significant change in serum calcium was observed in dogs administered a low dose of KAI-1455 by 3-hour intravenous infusion; however, PTH levels were increased at 2.75 hours, just before the end of infusion. A decrease in serum PTH was observed in dogs with doses of KAI-1455 sufficient to produce hypocalcemia.

Based on the relationship between serum calcium, bone metabolism and PTH, the inventors believe that calcium modulator peptides of the present invention, such as KAI-1455, should be beneficial for the treatment of hyperparathyroidism and various forms of bone disease and/or hypercalcemia. These compounds may have advantages compared to current therapeutic agents, because they may be administered parenterally and may not be associated with gastrointestinal adverse effects, are not metabolized by cytochrome P450 and may result in more effective reductions in serum PTH and calcium.

The methods of the present invention may be used alone or in combination with other approaches for the treatment of hypercalcemia and/or bone disease. Such other approaches include, but are not limited to, treatment with agents such as antiresorptive bisphosphonate agents, such as alendronate and risedronate; integrin blockers, such as $\alpha_v\beta_3$ antagonists; conjugated estrogens used in hormone replacement therapy, such as PREMPRO™, PREMARIN™ and ENDOMETRION™; selective estrogen receptor modulators (SERMs), such as raloxifene, droloxifene, CP-336,156 (Pfizer) and lasofoxifene; cathespin K inhibitors; vitamin D therapy; low dose PTH treatment (with or without estrogen); calcitonin; inhibitors of RANK ligand; antibodies against RANK ligand; osteoprotegrin; adensosine antagonists; and ATP proton pump inhibitors.

While PTH is typically associated with bone resorption, under certain conditions PTH has been found to stimulate the accumulation of osteoblasts and bone growth. PTH's osteogenic action is believed to occur through stimulation of preosteoblast proliferation and the reversion of quiescent lining cells to active osteoblasts. PTH may also function to build bone by increasing osteoblast activity and/or life span by preventing apoptosis. Accordingly, a small increase in PTH may have an anabolic affect, leading to bone growth.

In one embodiment, a calcium modulator peptide is administered at a dose sufficient to decrease both PTH and serum calcium levels. In another embodiment, a calcium modulator peptide is administered at a dose sufficient to decrease PTH without significantly affecting serum calcium levels. In a further embodiment, a calcium modulator peptide is administered at a dose sufficient to increase PTH without significantly affecting serum calcium levels Formulations Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Pharmaceutical compositions of the present invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the compounds of the present invention may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

For example, a polycationic peptide may be delivered to a human in a form of solution that is made by reconstituting a solid form of the drug with liquid. This solution may be further diluted with infusion fluid such as 0.9% sodium chloride injection, 5% dextrose injection and lactated ringer's injection. It is preferred that the reconstituted and diluted solutions be used within 4-6 hours for delivery of maximum potency. Alternatively, a polycationic peptide may be delivered to a human in a form of tablet or capsule.

Injectable depot forms are made by forming microencapsule matrices of the compounds of the present invention in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier. These compounds may be administered to humans and other animals for therapy by any suitable route of administration, including, e.g., subcutaneous injection, subcutaneous depot, intravenous injection, and intravenous or subcutaneous infusion.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of the present invention for a patient, when used for the indicated effects, will range from about 1 mcg to about 5 mg per kilogram of body weight per hour. In other embodiments, the dose will range from about 5 mcg to about 2.5 mg per kilogram of body weight per hour. In further embodiments, the dose will range from about 5 mcg to about 1 mg per kilogram of body weight per hour.

If desired, the effective daily dose of the active compound may be administered as two, three, four, five, six or more sub-doses administered separately at appropriate intervals throughout the day, optionally, in unit dosage forms. In one embodiment, the compound is administered as one dose per day. In further embodiments, the compound is administered continuously, as through intravenous or other routes. In other embodiments, the compound is administered less frequently than daily, such as weekly or less.

While it is possible for a compound of the present invention to be administered alone, it is preferable to administer the compound as a pharmaceutical formulation (composition).

The subject receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy thus includes sequential, simultaneous and separate administration of the active compound in a way that the therapeutical effects of the first administered one is not entirely disappeared when the subsequent is administered.

Possible Routes of Administration for Disclosed Compounds

These compounds may be administered to humans and other animals for therapy by any suitable route of administration. As used herein, the term "route" of administration is intended to include, but is not limited to subcutaneous injection, subcutaneous depot, intravenous injection, intravenous or subcutaneous infusion, intraocular injection, intradermal injection, intramuscular injection, intraperitoneal injection, intratracheal administration, intraadiposal administration, intraarticular administration, intrathecal administration, epidural administration, inhalation, intranasal administration, oral administration, sublingual administration, buccal administration, rectal administration, vaginal administration, intracisternal administration and topical administration, or administration via local delivery (for example by catheter or stent). The polycationic peptides may also be administered or coadministered in slow release dosage forms. The disclosed compounds have efficacy when administered systemically.

As described above, the methods of the present invention may be used alone or in combination with other approaches for the treatment of hypercalcemia and/or bone disease. Such other approaches include, but are not limited to, treatment with agents such as bisphosphonate agents, integrin blockers, hormone replacement therapy, selective estrogen receptor modulators, cathepsin K inhibitors, vitamin D therapy, anti-inflammatory agents, low dose PTH therapy (with or without estrogen), calcitonin, inhibitors of RANK ligand, antibodies against RANK ligand, osteoprotegrin, adensosine antagonists and ATP proton pump inhibitors.

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

A combination treatment of the present invention as defined herein may be achieved by way of the simultaneous, sequential or separate administration of the individual components of said treatment.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and a carrier suitable for coating said implantable device. In still another aspect, the present invention includes an implantable device coated with a composition comprising a compound of the present invention as described generally above, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121, herein incorporated by reference in their entirety. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Potential Clinical Markers for Determining Treatment Efficacy

Determination of the effectiveness of a method of treatment of the present invention may be determined by a variety of methods.

Normal levels of serum calcium are in the range of 8.0 to 10.8 mg/dL (2.0 to 2.7 mmol/L). In certain cases, the efficacy of treatment may be determined by measurement of serum and urinary markers related to calcium, including but not limited to, total and ionized serum calcium, albumin, serum PTH, PTHrP, phosphate, vitamin D, and magnesium.

In other cases, efficacy may be determined by measurement of bone mineral density (BMD), or by measurement of biochemical markers for bone formation and/or bone resorption in serum or urine. Potential bone formation markers include, but are not limited to, total alkaline phosphatase, bone alkaline phosphatase, osteocalcin, under-carboxylated osteocalcin, C-terminal procollagen type I propeptide, and N-terminal procollagen type I propeptide. Potential bone resorption markers include, but are not limited, hydroxyproline, hydroxylysine, glycosyl-galactosyl hydroxylysine, galactosyl hydroxylysine, pyridinoline, deoxypyridinoline, N-terminal crosslinking telopeptide of type I collagen, C-terminal crosslinking telopeptide of type I collagen, C-terminal crosslinking telopeptide of type I collagen generated by MMPs, bone sialoprotein, acid phosphatase and tartrate-resistant acid phosphatase.

It is expected that when a method of treatment of the present invention is administered to a subject in need thereof, said method of treatment will produce an effect, as measured by, for example, one or more of: total serum calcium, ionized serum calcium, albumin, serum PTH, PTHrP, phosphate, vitamin D, magnesium, bone mineral density (BMD), total alkaline phosphatase, bone alkaline phosphatase, osteocalcin, under carboxylated osteocalcin, C-terminal procollagen type I propeptide, N-terminal procollagen type I propeptide, hydroxyproline, hydroxylysine, glycosyl-galactosyl hydroxylysine, galactosyl hydroxylysine, pyridinoline, deoxypyridinoline, N-terminal crosslinking telopeptide of type I collagen, C-terminal crosslinking telopeptide of type I collagen, C-terminal crosslinking telopeptide of type I collagen generated by MMPs, bone sialoprotein, acid phosphatase and tartrate-resistant acid phosphatase. Effects include prophylactic treatment as well as treatment of existing disease.

A biologically effective molecule may be operably linked to the peptide of the invention with a covalent bond or a non-covalent interaction. In specific embodiments, the operably linked biologically effective molecules can alter the pharmacokinetics of the peptides of the above described embodiments of the invention by virtue of conferring properties to the peptide as part of a linked molecule. Some of the properties that the biologically effective molecules can confer on the peptides include, but are not limited to: delivery of a peptide to a discrete location within the body; concentrating the activity of a peptide at a desired location in the body and reducing its effects elsewhere; reducing side effects of treatment with a peptide; changing the permeability of a peptide; changing the bioavailability or the rate of delivery to the body of a peptide; changing the length of the effect of treatment with a peptide; altering the stability of the peptide; altering the rate of the onset and the decay of the effects of a peptide; providing a permissive action by allowing a peptide to have an effect.

In a further aspect, the calcium modulating peptides of the present invention may be conjugated to polyethylene glycol (PEG). The selected PEG may be of any convenient molecular weight, and may be linear or branched, and may be optionally conjugated through a linker. The average molecular weight of PEG will preferably range from about 2 kiloDalton (kDa) to about 100 kDa, more preferably from about 5 kDa to about 40 kDa.

The calcium modulating peptides may be conjugated to PEG through a suitable amino acid residue located at any position on the cargo peptide and/or the polycationic peptide or peptides. Polycationic and cargo peptides as further described herein may optionally contain an additional amino acid residue to which PEG is conjugated, including for example, an additional basic residue, such as lysine.

PEGylated peptides are known in the art to increase plasma half-life of conjugated peptides. A variety of methods are known in the art for the formation of PEGylated peptides. For example, the PEG moiety can be linked to the amino termini, the carboxy termini or through a sidechain of the claimed peptide, optionally through the presence of a linking group. In other embodiments, the PEG moiety may be linked to the sulfur of a thiol-containing amino acid, such as cysteine, or may be coupled to the sidechain of a basic amino acid, such as lysine or arginine.

The PEG groups will generally be attached to the peptides of the invention by acylation or reductive alkylation through a reactive group on the PEG moiety (e.g., an aldehyde, amino, thiol, ester, or carboxylic acid group) to a reactive group on the inventive compound (e.g., an aldehyde, amino, ester, acid or thiol group), which may be located at the amino terminus, carboxy terminus, or a sidechain position of the polycationic or cargo peptide. One approach for preparation of PEGylation of synthetic peptides consists of combining through a conjugate linkage in solution, a peptide and a PEG moiety, each bearing a functional group that is mutually reactive towards the other. Peptides can be easily prepared using conventional solution or solid phase synthesis techniques. Conjugation of the peptide and PEG is typically done in aqueous phase and may be monitored by reverse phase HPLC. The PEGylated peptides can be readily purified and characterized, using standard techniques known to one of skill in the art.

One or more individual residues of the inventive peptides may also be modified with various derivatizing agents known to react with specific sidechains or terminal residues. For example, lysinyl residues and amino terminal residues may be reacted with succinic anhydride or other similar carboxylic acid anhydrides which reverses the charge on the lysinyl or amino residue. Other suitable reagents include, e.g., imidoesters such as methyl picolinimidate; pyridoxal; pyridoxal phosphate; chloroborohydride; trinitrobenzenesulfonic acid; O-methylisourea; 2,4-pentanedione; and transaminase-catalyzed reaction with glyoxalate. Arginyl residues may be modified by reaction with conventional agents such as phenylglyoxal, 2,3-butanedione, 1,2-cyclohexanedione, and ninhydrin.

In addition, the polycationic peptides of the present invention may be modified to include non-cationic residues that provide immunogenic residues useful for the development of antibodies for bioanalytical ELISA measurements, as well as to evaluate immunogenicity. For example, the polycationic peptides may be modified by incorporation of tyrosine and/or glycine residues. Specific modifications of tyrosyl residues are of particular interest for introducing spectral labels into tyrosyl residues. Non-limiting examples include reaction with aromatic diazonium compounds or tetranitromethane. Most commonly, N-acetylimidazole and tetranitromethane are used to form O-acetyl tyrosyl and 3-nitro derivatives, respectively.

Kits Comprising the Disclosed Compounds

The invention also provides kits for carrying out the therapeutic regimens of the invention. Such kits comprise therapeutically effective amounts of a polycationic peptide having activity as a CaSR modulator, in pharmaceutically acceptable form, alone or in combination with other agents, in pharmaceutically acceptable form. Preferred pharmaceutical forms include peptides in combination with sterile saline, dextrose solution, buffered solution, or other pharmaceutically acceptable sterile fluid. Alternatively, the composition may be lyophilized or desiccated. In this instance, the kit may further comprise a pharmaceutically acceptable solution, preferably sterile, to form a solution for injection purposes. In another embodiment, the kit may further comprise a needle or syringe, preferably packaged in sterile form, for injecting the composition. In other embodiments, the kit further comprises an instruction means for administering the composition to a subject. The instruction means can be a written insert, an audiotape, an audiovisual tape, or any other means of instructing the administration of the composition to a subject.

In one embodiment, the kit comprises (i) a first container containing a calcium modulator peptide having activity as a CaSR modulator; and (ii) instruction means for use.

In another embodiment, the kit comprises (i) a first container containing a calcium modulator peptide having activity as a CaSR modulator; (ii) a second container containing an anticalcemic agent; and (iii) instruction means for use.

In one embodiment, the anticalcemic agent is and agent selected from the group consisting of bisphosphonate agents, hormone replacement therapeutic agents, vitamin D therapy, low dose PTH (with or without estrogen), and calcitonin.

In related aspects, the invention provides articles of manufacture that comprise the contents of the kits described above. For instance, the invention provides an article of manufacture comprising an effective amount of a calcium modulator peptide having activity as a CaSR modulator, alone or in combination with other agents, and instruction means indicating use for treating diseases described herein.

Polypeptides of the present invention are referred to herein by their SEQ ID NO: or by an internal reference number, designated as a KAI-number and/or a KP-number, which are used interchangeably herein. For example, the peptide having SEQ ID NO:7 may be variously referred to herein as KAI-1455 or KP-1455. It will be understood by one of skill in the art that such numbers may be used interchangeably and refer to the same polypeptide sequence.

Unless otherwise specified, all documents referred to herein are incorporated by reference in their entirety.

EXAMPLES

The following examples are offered to illustrate but not to limit the invention. The principle features of the invention can be employed in various embodiments without departing from the scope of the invention. Various modifications may be made by the skilled person without departing from the true spirit and scope of the invention.

Example 1

Preparation of Test and Vehicle/Control Articles

An appropriate quantity of KAI-1455 (SEQ ID NO:7) was dissolved in a solution of 32.5 mg/mL mannitol and 32.5 mg/mL sucrose in Water for Injection (supplied by ITR) to achieve a stock concentration of 10 mg/mL of KAI-1455. The pH was adjusted to ~5, if necessary. The stock solution was diluted with sterile Saline for Injection to achieve the final dose solution concentrations. The solutions were filtered into a sterile container/bag, via 0.22 pm PVDF filter(s) (Millipore) prior to administration to the animals, and kept refrigerated until shortly before dosing, then allowed to warm to room temperature.

The solution of vehicle control was prepared by taking an appropriate volume of the 32.5 mg/mL mannitol/32.5 mg/mL sucrose solution in WFI and diluting this approximately 4.44-fold with SF1 (i.e., the same dilution ratio as for the high-dose solution of test article).

Example 2

Single-Dose Continuous Intravenous Infusion Toxicity and Toxicokinetic/Tissue Distribution Study of KAI-1455 in Rats with a 14-Day Recovery Period The study was conducted in Sprague Dawley rats (strain Crl:CD(SD)) obtained from Charles River Laboratories, Raleigh, N.C. A total of 42 rats (21 male and 21 female) were included in the study, with an n=3 per group. The average body weight range at the onset of treatment was 7-11 kg. The average age range at the start of treatment was 6-7 weeks for catheterization and 10-12 weeks for initiation of treatment. Average weight at initiation of treatment was 100 to 400 grams.

Administration of the Test and Control/Vehicle Articles:

Animals were catheterized via a femoral vein by the supplier. The appropriate dose was administered by intravenous infusion via a catheter implanted in a femoral vein. KAI-1455 (SEQ ID NO:7) was administered to rats by continuous intravenous infusion at doses of 10, 20 and 45 mg/kg over 24 hours, and at 45 mg/kg over 6 hours. All animals were dosed as a single continuous dose for approximately 6 or 24 hours. The dose volume was 20 mL/kg; dosing rates were 0.83 mL/kg/hour for animals given a 24-hour infusion, and 3.33 mL/kg/hour for animals given a 6-hour infusion. Sterile saline solution was infused at the maintenance rate during the predose period. Individual animal absolute dose volumes were based on the Day 1 body weight. Animals were disconnected from infusion following completion of the final dose. Catheters for the animals were cut, tied off, and left in place after the final dose.

An external pumping device was utilized to deliver the target dose volume for each animal over the specified dosing interval. A tether and harness device was employed to maintain infusion via the pump.

Results:

Animals administered KAI-1455 at 45 mg/kg over 24 hours became moribund due to extreme hypocalcemia and were euthanized on day 2. All other dose groups had normal calcium levels 24-42 hours post-end of infusion. Animals administered KAI-1455 at 20 mg/kg showed a dose dependent decrease in serum calcium on day 3 post-dosing. Calcium levels in these animals returned to normal by day 14, demonstrating that the decrease in total serum calcium caused by treatment with KAI-1455 is reversible. Serum calcium levels are given in Table 1.

TABLE 1

Total Serum Calcium (mg/dL) 2, 3 and 14 days after the end of infusion.

| Dose (mg/kg) | Infusion duration (hrs) | Males - Serum Calcium (mg/dL) | | | Females - Serum Calcium (mg/dL) | | |
|---|---|---|---|---|---|---|---|
| | | Day 2 | Day 3 | Day 14 | Day 2 | Day 3 | Day 14 |
| 0 | | | 10.8 | 10.8 | | 11.0 | 11.0 |
| 10 | 24 | | 11.0 | | | 11.1 | |
| 20 | 24 | | 10.4 | 11.1 | | 10.5 | 11.1 |
| 45 | 24 | 6.9 | | | 6.9 | | |
| 45 | 6 | | 10.3 | | | 10.8 | |

A pronounced increase in serum phosphate levels was observed 24-hours post-EOI in rats receiving KAI-1455 at 45 mg/kg over 24 hours. A possible sustained increase in serum phosphate was observed in the 20 mg/kg dose group. All other dose groups had normal serum phosphate 24-42 hours post-EOI (data not shown).

Example 3

A Single-dose (24-Hour) Continuous Intravenous Infusion Toxicity and Toxicokinetic/Tissue Distribution Study of KAI-1455 in Beagle Dogs The study was conducted in beagle dogs obtained from Marshall BioResources, Inc. A total of 24 dogs were included in the study (12 males, 12 females), with n=3/sex per group. The average body weight range at the onset of treatment was 7-11 kg. The average age range at the start of treatment was 7-11 months old.

Administration of the Test and Control/Vehicle Articles:

KAI-1455 (SEQ ID NO:7) and control articles were administered over a single 24-hour period by intravenous infusion at a dose rate of 0.83 mL/kg/hour, via a disposable indwelling catheter (Abbocath® or Angiocath®) inserted into one of the cephalic or saphenous veins and connected to an infusion pump by means of medical-grade tubing. The actual volume (mL) infused was calculated based on the most recent practical body weight of each animal.

KAI-1455 was administered at doses of 10, 20 and 40 mg/kg over 24 hours. Serum calcium levels (mmol/L) were determined on day 3, 24 hours post-end of infusion (EOI).

Prior to the start of the infusion, the infusion line of each dog was pre-filled with the appropriate dosing solution to ensure that dosing of the animal started as soon as the as the infusion pump was turned on. This ensured that the whole dose was given to the animals. The infusion bags were changed at appropriate intervals (if necessary) and the weights were recorded prior to the start and at the end of the infusion.

Results:

A dose dependent decrease in total serum calcium was observed 24 hours post-end of infusion. Serum calcium levels are shown in Table 2.

TABLE 2

Total Serum Calcium levels 24 hours post-dosing.

| Dose (mg/kg over 24 hours) | Males - Serum Calcium (mmol/L) | | | Females - Serum Calcium (mmol/L) | | |
|---|---|---|---|---|---|---|
| | Pre-dose | 24-hours post-dose | % change | Pre-dose | 24-hours post-dose | % change |
| Placebo | 2.83 | 2.77 | 2.12 | 2.84 | 2.81 | 1.06 |
| 10 | 2.83 | 2.60 | 9.09 | 2.81 | 2.53 | 9.96 |

TABLE 2-continued

Total Serum Calcium levels 24 hours post-dosing.

| Dose (mg/kg over 24 hours) | Males - Serum Calcium (mmol/L) | | | Females - Serum Calcium (mmol/L) | | |
|---|---|---|---|---|---|---|
| | Pre-dose | 24-hours post-dose | % change | Pre-dose | 24-hours post-dose | % change |
| 20 | 2.86 | 2.32 | 20.00 | 2.84 | 2.40 | 15.49 |
| 40 | 2.90 | 1.93 | 33.45 | 2.41 | 2.10 | 12.86 |

Example 4

A Safety Pharmacology Study of KAI-1455 Administered as a 12-Hour Intravenous Infusion to Beagle Dogs KAI-1455 (SEQ ID NO:7) was administered to beagle dogs by continuous intravenous infusion at doses of 1, 5 and 12.5 mg/kg over 12 hours (n=3 per dose). The affect on serum calcium was determined at the 12 hour time point, immediately following the end of infusion (EOI), and at 24 hours post-EOI.

Results:

A dose dependent reduction in serum calcium was observed at EOI. The maximal calcium decrease was observed at the EOI. Partial recovery of calcium levels was observed 24 hours post-EOI, with animals still showing a measurable decrease in serum calcium over baseline in the 12.5 mg/kg dose group. Serum calcium levels are shown in Table 3.

TABLE 3

Total Serum Calcium (mg/dL) predose, at the end of infusion (EOI), and 12 hours post-EOI.

| Dose (mg/kg) | Infusion duration (hrs) | 0 hrs | 12 hrs (EOI) | 36 hrs (24 hrs post-EOI) | % Change at EOI |
|---|---|---|---|---|---|
| 1 | 12 | 10.6 | 10.4 | | −2.2 |
| 5 | 12 | 10.6 | 9.6 | | −9.7 |
| 12.5 | 12 | 10.5 | 8.8 | 9.5 | −15.9 |

A dose dependent increase in serum phosphate level was observed at the EOI and at 24 hours post-EOI. Serum phosphate levels are shown in Table 4.

TABLE 4

Serum Phosphate (mg/dL) predose and at the end of infusion (EOI)

| Dose (mg/kg) | Infusion duration (hrs) | 0 hrs | 12 hrs (EOI) | % Change |
|---|---|---|---|---|
| 1 | 12 | 4.7 | 4.4 | −7.0 |
| 5 | 12 | 4.6 | 5.4 | 17.3 |
| 12.5 | 12 | 4.5 | 6.4 | 39.6 |

A significant decrease in PTH was observed at the EOI and at 24 hours post-EOI for animals in the 12.5 mg/kg dose group. The plasma PTH level decreased to about 15% of baseline pretreatment level at the EOI, with a sustained decrease of about 50% of baseline pretreatment level at 24 house post-EOI. PTH levels (pg/mL) are shown in Table 5.

TABLE 5

PTH (pg/mL) pre-dose and at the end of infusion

| Dose (mg/kg) | Infusion duration (hrs) | 0 hrs | 12 hrs (EOI) |
|---|---|---|---|
| 12.5 | 12 | 68.7 | 10.2 |

The relationship between PTH, serum calcium, and serum phosphate levels is shown in FIG. 1. A decrease in calcium levels coincides with an increase in serum phosphate and a decrease in PTH.

Example 5

Single-Dose Calcium Infusion Study of KAI-1455 in Sprague Dawley Rats

The study was designed to investigate the time course of changes in serum calcium during an approximate 24-hour intravenous infusion of a single dose of KAI-1455 (SEQ ID NO:7) at 45 mg/kg and explore the potential for calcium supplementation to ameliorate clinical signs associated with toxicity of KAI-1455 infusion in rats.

The study was conducted in Sprague Dawley rats (strain Crl:CD(SD)IGS BR) obtained from Charles River Laboratories, Hollister, Calif. A total of 20 rats (n=5/sex per group) were included in the study. The average age range at the start of treatment was 5-8 weeks (at receipt). Average weight at initiation of treatment was 160 to 380 grams.

Administration of the Test and Control/Vehicle Articles:

Animals were catheterized in the jugular vein by the supplier. Animals were assigned to groups and treated according to Table 6.

TABLE 6

| | | | Group Assignments | | | |
|---|---|---|---|---|---|---|
| Treatment Group | Test Article | Dose Level (mg/kg) | Dose concentration (mg/mL) | Dose volume (mL/kg) | Number of animals | |
| | | | | | Male | Female |
| 1 | KAI-1455 | 45 | 2.25/0.75** | 10/30*** | 5 | 5 |
| 2 | KAI-1455* | 45 | 2.25/0.75** | 10/30*** | 5 | 5 |

The total intravenous infusion time was ~24 hours.
*During the second ~12 hour infusion, Group 2 received an infusate containing calcium (mixed with the KAI-1455 dosing solution) at a final concentration of 0.8 mg/mL elemental calcium.
**The final concentration of test article in the infusate for the first 12-hour portion of the infusion was ~2.25 mg/mL, and for the second 12-hour infusion was ~0.75 mg/mL.
***For the first 12-hours of infusion, the infusion rate was ~0.83 mL/kg/hour (~10 mL/kg total volume), and for the second 12-hour infusion period, the infusion rate was ~2.5 mL/kg/hour (~30 mL/kg total volume).

Absolute dose volumes for individual animals were calculated based on the most recent body weight.

Three test article dosing solutions were prepared for the study. For administration during the first 12 hours of infusion, a single solution was prepared for both groups by dilution of the 10 mg/mL stock solution with SFI to obtain a final KAI-1455 concentration of 2.25 mg/mL. The first set of dosing syringes was filled from this solution for infusion.

For Group 1, a dosing solution for administration during the second 12 hours of infusion was prepared by dilution of the 10 mg/mL stock solution with SFI to obtain a final KAI-1455 concentration of 0.75 mg/mL. The second set of dosing syringes for Group 1 was filled from this solution for infusion.

For Group 2, the dosing solution for administration during the second 12 hours of infusion contained KAI-1455 at a concentration of 0.75 mg/mL, along with calcium gluconate at a final concentration of 0.8 mg/mL of elemental calcium. The solution was prepared by first diluting the 10 mg/mL stock solution into a larger volume of required SFI and then adding the appropriate amount of calcium gluconate followed by addition of more SFI to reach the desired volume. The second set of dosing syringes for Group 2 was filled from this solution for infusion.

Commercially available 10% calcium gluconate injection was used for calcium supplementation. The solution contains 9 mg of elemental calcium per mL. The desired final concentration of elemental calcium in the dosing solutions for Group 2 administered during the second 12-hour infusion is ~0.8 mg/mL.

Blood Collection and Sampling Method:

Blood was collected by venipuncture from the peripheral vein of restrained conscious animals. At each timepoint (except for termination timepoint), approximately 1.1 mL of blood was collected from overnight-fasted animals. Ionized calcium, PTH, and total serum calcium was measured for all animals pre-infusion, 12 hours from initiation of study (prior to initiation of calcium supplementation), at the completion of infusion, and at necropsy.

Results:

At the 12 hour timepoint, prior to the start of the calcium infusion, mean total calcium for all animals had declined from 10.5 mg/dL to 8.0 mg/dL. During the second 12 hours of infusion, mean total calcium further declined to 6.8 mg/dL in the rats that received KAI-1455 alone and to 7.6 mg/dL in the rats that received KAI-1455 and calcium (FIG. 8). None of the 8 rats that received KAI-1455 and calcium supplementation died (2 rats died prior to the start of the calcium infusion; one related to the 12 hour blood draw and the other at 5 hours after the start of infusion), whereas 3 of the 10 rats (30%) that received KAI-1455 alone died. Calcium supplementation (2 mg/kg/hr) by intravenous infusion during the latter half of a 24-hour KAI-1455 infusion partially attenuated the reduction in serum calcium associated with KAI-1455, which was sufficient to prevent the mortality associated with high-dose KAI-1455 infusion. The observed calcium drop recovered by 48 hours (24 hours post-EOI).

Example 6

Single-Dose Calcium Infusion Study of KAI-1455 in Beagle Dogs

The dose-response and time course for hypocalcemia, as well as the potential to prevent hypocalcemia and ameliorate clinical signs of toxicity by providing calcium supplementation were studied in dogs.

Three dogs were administered doses of 12.5, 1.0 and 5 mg/kg (infused over 12 hours) consecutively (with appropriate washout periods between doses), in order to thoroughly characterize the dose-response for hypocalcemia and other endpoints and to investigate the relationships between changes in serum calcium, clinical signs, PTH, QT prolongation, and other effects on the animals.

Following this phase of the study, the same dogs were used to explore the potential for calcium supplementation to prevent or ameliorate toxicity. In this latter phase, all three dogs received 25 mg/kg of KAI-1455 over 12 hours (i.e., a dose that was previously associated with apparent moribundity), but they were supplemented at the onset of infusion with calcium gluconate, infused concurrently with KAI-1455 at a rate of 2 mg elemental calcium/kg/hr (i.e., the same rate that was used in the rat calcium supplementation study, described above). Serum calcium was monitored every 3 hours during the infusion and periodically after the infusion.

Results:

A slight rise in calcium during the KAI-1455 infusion while receiving calcium supplementation tended to normalize by the end of the 12-hour infusion, following which calcium levels began to fall (FIG. 2). At ~3 hours post EOI, the animals began to exhibit symptoms of hypocalcemia. Calcium infusion was restarted and continued for ~3 hours, upon which the animals' symptoms promptly resolved. The calcium concentration measured at 24 hours after the KAI-1455 infusion had again regressed to a sub-normal level, indicating that the effect of KAI-1455 was still ongoing (albeit much less pronounced) following the additional calcium supplementation. Serum phosphate levels increased during the 12 hour infusion, and remained above baseline at 6 hours post-EOI (FIG. 3).

Example 7

Table of SEQ ID NOs

TABLE 7

Peptide sequences and corresponding SEQ ID NOs

| Peptide sequence | SEQ ID NO: |
|---|---|
| HDAPIGYD | SEQ ID NO: 1 |
| CHDAPIGYD | SEQ ID NO: 2 |
| YGRKKRRQRRR | SEQ ID NO: 3 |
| CYGRKKRRQRRR | SEQ ID NO: 4 |
| Ac-CYGRKKRRQRRR-NH$_2$ | SEQ ID NO: 5 |
| CHDAPIGYD<br>\|<br>CYGRKKRRQRRR | SEQ ID NO: 6<br>(KAI-9706) |
| CHDAPIGYD<br>\|<br>Ac-CYGRKKRRQRRR-NH$_2$ | SEQ ID NO: 7<br>(KAI-1455) |
| CSFNSYELGSL<br>\|<br>CYGRKKRRQRRR | SEQ ID NO: 8<br>(KAI-9803) |
| CPDYHDAGI<br>\|<br>Ac-CYGRKKRRQRRR-NH$_2$ | SEQ ID NO: 9<br>(KAI-1524) |
| CEAVSLKPT<br>\|<br>Ac-CYGRKKRRQRRR-NH$_2$ | SEQ ID NO: 10<br>(KAI-1586) |
| EAVSLKPTGGYGRKKRRQRRR-NH$_2$ | SEQ ID NO: 11<br>(KAI-1633) |
| CRFARKGALRQKNV<br>\|<br>Ac-CYGRRARRRARR-NH$_2$ | SEQ ID NO: 12<br>(KAI-1655)<br>SEQ ID NO: 35 |
| Ac-CYGRKKRRQRRR-NH$_2$<br>\|<br>Ac-CYGRKKRRQRRR-NH$_2$ | SEQ ID NO: 13 |
| ├──────────────┤<br>Ac-CYGRKKRRQRRRC-NH$_2$ | SEQ ID NO: 14 |
| Ac-CRRR-NH$_2$<br>\|<br>Ac-CYGRKKR-NH$_2$ | SEQ ID NO: 15<br>SEQ ID NO: 36 |
| Ac-CYGRKKR-NH$_2$<br>\|<br>Ac-CYGRKKR-NH$_2$ | SEQ ID NO: 16 |
| Ac-CRRR-NH$_2$<br>\|<br>Ac-CRRR-NH$_2$ | SEQ ID NO: 17 |
| Ac-CRRRR-NH$_2$<br>\|<br>Ac-CRRRR-NH$_2$ | SEQ ID NO: 18 |
| Ac-CRRR-NH$_2$ | SEQ ID NO: 19 |
| Ac-CRRRR-NH$_2$ | SEQ ID NO: 20 |
| Ac-CRRRRRRR-NH$_2$ | SEQ ID NO: 21 |
| Ac-CRRRRRRRR-NH$_2$ | SEQ ID NO: 22 |
| Ac-CRRRRRRRRR-NH$_2$ | SEQ ID NO: 23 |
| Ac-CRRRRRRRRRR-NH$_2$ | SEQ ID NO: 24 |

TABLE 7-continued

Peptide sequences and corresponding SEQ ID NOs

| Peptide sequence | SEQ ID NO: |
|---|---|
| Ac-CRRRRRRRRRRR-NH$_2$ | SEQ ID NO: 25 |
| Ac-CRRRRRRRRRRRR-NH$_2$ | SEQ ID NO: 26 |
| YGRKKR | SEQ ID NO: 27 |
| CYGRKKR | SEQ ID NO: 28 |
| Ac-CYGRKKR-NH$_2$ | SEQ ID NO: 29 |
| YGRRARRRARR | SEQ ID NO: 30 |
| CYGRRARRRARR | SEQ ID NO: 31 |
| Ac-CYGRRARRRARR-NH$_2$ | SEQ ID NO: 32 |
| CRRR | SEQ ID NO: 33 |
| CRRRR | SEQ ID NO: 34 |

Example 8

Single Ascending Dose Study of KAI-1455 in Human Volunteers

Study Design:

A double blinded, randomized, placebo controlled single ascending dose study of KAI-1455 (SEQ ID NO:7) was conducted in healthy human volunteers. The initial study design required the administration of KAI-1455 (SEQ ID NO:7) by intravenous infusion over 12 hours to seven cohorts, with an initial dose of 1 mg/kg. Dose escalation was dependent on the safety of the preceding dose. Each cohort was randomly assigned 4 young, male subjects (n=4). Cohorts were randomized so that 3 subjects received the active drug and one subject received placebo.

Subjects were monitored for a one-week follow-up period between the dose cohorts. Study endpoints, including clinical and laboratory safety, pharmacokinetics, serum ionized calcium (iCa), total calcium, phosphate, and plasma PTH, were determined for each subject.

Results:

KAI-1455 was generally safe and well tolerated at doses ranging from 1-162 mg/kg over 12 hours. KAI-1455 was associated with dose dependent decreases in serum calcium and plasma PTH. The reductions in serum calcium and plasma PTH reached a nadir at the end of infusion (EOI) but remained suppressed for up to 36 hours following the end of infusion at the highest dose. Dose rates of ≤0.1 mg/kg/hour were associated with <10% mean maximal decrease in serum calcium with 12-hour infusions.

Plasma Pharmacokinetics:

Doses of 18, 54, 81 and 162 mg/kg of KAI-1455 (SEQ ID NO:7) were administered to healthy male volunteers by intravenous infusion over 12 hours. The plasma concentration (ng/mL) of KAI-1455 was determined at the 1, 3, 6, 9, and 12 hour timepoints during the 12 hour infusion, and was measured for up to one hour following the end-of-infusion (EOI). At the highest dose, a sustained plasma concentration of about 100 ng/mL was achieved from the 9-12 hour timepoints, which gradually returned to baseline by about 30 minutes post-EOI (FIG. 4).

Ionized Calcium by Treatment Group:

Serum ionized calcium (mmol/L) was determined at the start of infusion, and at 3, 6, 9, 12, 15, 18, 21, 24 and 48 hours after the start of infusion. A dose dependent reduction in ionized calcium was observed, with the maximal calcium decreases observed at about the 15 and 18 hour timepoints (i.e., 3 to 6 hours post-EOI). At the highest dose, the maximal calcium decrease was maintained for 12 hours post-EOI. Partial recovery of calcium levels was observed at 12 hours post-EOI, with subjects still showing a significant decrease in ionized calcium over baseline at 12 and 36 hours post-EOI in the 54, 81, and 162 mg/kg dose groups (FIG. 5).

Total Calcium by Treatment Group:

Total calcium level (mg/dL) was determined at the start of infusion, and at 3, 6, 9, 12, 15, 18, 21, 24 and 48 hours after the start of infusion. A dose dependent reduction in total calcium was also observed, with the maximal calcium decreases observed at about the 15 and 18 hour timepoints (i.e., 3 to 6 hours post-EOI). At the highest dose, the maximal calcium decrease was maintained for 12 hours post-EOI. Partial recovery of calcium levels was observed at 12 hours post-EOI, with subjects still showing a significant decrease in total calcium over baseline at 12 and 36 hours post-EOI in the 54, 81, and 162 mg/kg dose groups (FIG. 6).

Percent Change in Calcium by Treatment Group:

The percent change in calcium was determined for each treatment group. The maximal percent change was observed at about the 15 and 18 hour timepoints (i.e., 3 to 6 hours post-EOI). In the 162 mg/kg dose group, a maximal percent reduction in calcium of greater than 15% was observed (FIG. 7).

Plasma PTH by Treatment Group:

Plasma PTH level (pg/mL) by treatment group were determined at the start of infusion, and at 3, 6, 12, 15, 18, 24 and 48 hours after the start of infusion. The maximal reduction in plasma PTH was observed at the EOI. A significant decrease in PTH was observed at the EOI and at 12 hours post-EOI for subjects in the 162 mg/kg dose group, with sustained decreases below pretreatment baseline levels still observable 36 hours post-EOI (FIG. 8).

Percent Change in Plasma PTH by Treatment Group:

The percent change in plasma PTH level was determined for each treatment group. The maximal percent change was observed at the EOI. A maximal percent change in plasma PTH level of greater than 40% was observed for subjects in the 81 and 162 mg/kg dose groups, with levels still significantly below baseline 12 hours post-EOI, with PTH levels returning towards baseline at 36 hours post-EOI (FIG. 9).

Example 9

4 Hour Infusion Study of KAI-1455 in Human Volunteers

Study Design:

Two additional cohorts were administered KAI-1455 (SEQ ID NO:7) at doses of 54 or 108 mg/kg by intravenous infusion for 4 hours. Cohorts were enrolled after the maximum tolerated dose was defined for the 12-hour infusions. Each cohort was randomly assigned 4 young, male subjects (n=4). Cohorts were randomized so that 3 subjects received the active drug and one subject received placebo.

Subjects were monitored for 36 hours following the end of infusion (EOI). Study endpoints, including ionized calcium (iCa), and plasma PTH, were determined for each treatment group. Dose rates of ≤0.2 mg/kg/hour were associated with <10% mean maximal decrease in serum calcium with 4-hour infusions.

Ionized Calcium by Treatment Group:

Serum ionized calcium (mmol/L) was determined at the start of infusion, and at 2, 3, 4, 6, 8, 12, 16, and 36 hours after the start of infusion. A dose dependent reduction in ionized calcium was observed, with the maximal ionized calcium reduction observed at about 4 hours post-EOI for the 54 mg/kg dose group, and 12 hours post-EOI for the 108 mg/kg dose group (FIG. 10).

Total Calcium by Treatment Group:

The reduction in total calcium (mg/dL) was likewise determined at the start of infusion, and at 2, 3, 4, 6, 8, 12, 16, and 36 hours after the start of infusion. A dose dependent reduction in ionized calcium was observed, with the maximal total calcium reduction observed at about 8 hours post-EOI for the 54 mg/kg dose group, and 12 hours post-EOI for the 108 mg/kg dose group, with a significant reduction in total calcium observed at 32 hours post-EOI for the 108 mg/kg dose group (FIG. 11).

Plasma PTH by Treatment Group:

Plasma PTH level (pg/mL) by treatment group were determined at the start of infusion, and at 2, 3, 4, 6, 8, 12, 16, and 36 hours after the start of infusion. The maximal reduction in plasma PTH was observed at the EOI. A significant decrease in plasma PTH was observed at the EOI and at 8 hours post-EOI for subjects in the 108 mg/kg dose group (FIG. 12).

Example 10

4 Hour Infusion Study of KP-1524 in Anesthetized Rats

Study Design:

The study was designed to determine the effect of the cargo peptide on the ability of the calcium modulator peptide to reduce total calcium and/or plasma PTH levels.

Materials and Methods:

KP-1524 (SEQ ID NO: 9) was administered at a dose rate of 9 mg/kg by intravenous infusion for 3 hours to rats (n=4) anesthetized with isoflurane. Control animals (n=4) were infused with saline. Blood samples were taken preinfusion, and at 1, 2, 3 and 4 hour timepoints. Total calcium (mg/dL) and PTH (pg/mL) were determined.

Results:

Treatment animals showed a significant decrease in total calcium and PTH levels. The maximal reduction in total calcium (mg/dL) and was observed at 1 hour post-EOI (FIG. 13(A)). The maximal reduction in plasma PTH (pg/mL) and was observed by the 2 hour timepoint, and a significant reduction in plasma PTH persisted at 1 hour post-EOI (FIG. 13(B)). The increase in plasma PTH levels observed in the saline treated animals is presumably due to diuresis.

Example 11

3 Hour Infusion Study of KAI-1455 and KP-1524 in Anesthetized Rats

Materials and Methods:

KAI-1455 (SEQ ID NO:7) and KP-1524 (SEQ ID NO: 9) were administered at a dose rate of 9 mg/kg by intravenous infusion for 3 hours to rats (n=3) anesthetized with isoflurane. Control animals (n=2) were infused with saline. Blood samples were taken preinfusion, and at 1, 2, 3, 6 and 24 hour timepoints. Total calcium (mg/dL) and PTH (pg/mL) were determined.

Results:

Treatment animals showed a significant decrease in total calcium and PTH levels, with maximal reductions observed around the EOI. The reduction in total calcium was maintained for up to 4 hours post-EOI for both KAI-1455 and KP-1524, and the reductions in total calcium and PTH were comparable for the two peptides (data not shown).

Example 12

3 Hour Infusion Study of KAI-9706 in Anesthetized Rats

Study Design:

The study was designed to determine the contribution of the capping group on the cationic peptide to the reductions in calcium and plasma PTH.

Materials and Methods:

KP-9706 (SEQ ID NO: 6) was administered at a dose rate of 9 mg/kg by intravenous infusion for 3 hours to rats (n=4) anesthetized with isoflurane. Control animals (n=4) were infused with saline. Blood samples were taken preinfusion, and at 1, 2, 3, 4 and 24 hour timepoints. Total calcium (mg/dL) and PTH (pg/mL) were determined.

Results:

KP-9706 did not show a reduction in total calcium (FIG. 14) or plasma PTH levels (data not shown).

Example 13

In Vitro Plasma Stability in Rat EDTA Plasma

Materials and Methods:

In vitro plasma stability in rat EDTA plasma was determined for KAI-1455 (SEQ ID NO:7), KP-9706 (SEQ ID NO:6) and KP-9803 (SEQ ID NO:8)

Results:

The capped calcium modulator peptide, KAI-1455 (SEQ ID NO:7), was substantially more stable in plasma than either of the uncapped peptides, KP-9706 (SEQ ID NO:6) and KP-9803 (SEQ ID NO:8). KAI-1455 demonstrated a half-life ($t_{1/2}$) of ca. 50 minutes in rat EDTA plasma. KP-9706 (SEQ ID NO:6) and KP-9803 (SEQ ID NO:8) demonstrated half-lives of ca. 5 and 10 minutes, respectively (FIG. 15). Similar results were observed in human and dog plasma (data not shown).

Example 14

3 Hour Infusion Study of KAI-1586 and KAI-1633 in Anesthetized Rats

Study Design:

The study was designed to determine the contribution of the disulfide bond and/or cysteine residue on the calcium modulator peptide to the reductions in total calcium and plasma PTH.

Materials and Methods:

KAI-1633 (SEQ ID NO:11) was administered at a dose rate of 9 mg/kg by intravenous infusion for 3 hours to rats (n=3) anesthetized with isoflurane. Control animals (n=4) were infused with saline. Blood samples were taken preinfusion, and at 1, 2, 3, 4 and 24 hour timepoints for determination of total calcium (mg/dL) and PTH (pg/mL).

Results:

KAI-1633 did not show a reduction in total calcium or plasma PTH levels (data not shown). The steady state plasma concentration for KAI-1633 at 9 mg/kg was determined by ELISA to be about 3500 ng/mL. By comparison, the steady state plasma concentration for KAI-1455 at 9 mg/kg was determined by ELISA to be about 2200 ng/mL. The steady state pharmacokinetic data suggest that KAI-1455 and KAI-1633 demonstrate similar systemic exposure. The observed differences in efficacy at reducing total calcium and plasma PTH cannot be solely attributed to differences in pharmacokinetics between the two compounds.

Example 15

Representative Embodiments

The following representative embodiments are included to illustrate but not to limit the invention.

1. A method for decreasing parathyroid hormone (PTH) levels in a subject, comprising:

administering a therapeutically effective amount of a calcium modulator peptide to a subject in need thereof, whereby serum PTH is reduced;

wherein the calcium modulator peptide comprises:

a) a polycationic peptide comprising 5 to 20 amino acids which are positively charged at physiological pH, an amino terminus, a carboxy terminus, and a first thiol-containing residue;

wherein the polycationic peptide is chemically modified at the amino terminus, the carboxy terminus, or both; and b) a cargo peptide comprising a second thiol-containing residue;

wherein the second thiol-containing residue is disulfide bonded to the first thiol-containing residue.

2. The method of embodiment 1, wherein the therapeutically effective amount of the calcium modulator peptide is sufficient to reduce serum PTH by at least 20% for at least 10 hours post-administration of the calcium modulator peptide.

3. The method of embodiment 1, wherein the therapeutically effective amount of the calcium modulator peptide is sufficient to reduce serum PTH by 30% to 70% for at least 48 hours post-administration of the calcium modulator peptide.

4. The method of embodiment 1, wherein the subject is afflicted with primary hyperparathyroidism, secondary hyperparathyroidism, tertiary hyperparathyroidism, hypercalcemia of malignancy, metastatic bone disease, Paget's disease, osteoarthritis, rheumatoid arthritis, osteomalacia, chondrocalcinosis, achondroplasia, osteochondritis, osteogenesis imperfecta, congenital hypophosphatasia, fibromatous lesions, fibrous dysplasia, multiple myeloma, osteolytic bone disease, periprosthetic osteolysis, periodontal disease, osteoporosis, abnormal bone turnover, or high turnover bone disease.

5. The method of embodiment 4, wherein the subject is afflicted with secondary hyperparathyroidism.

6. A method for decreasing parathyroid hormone (PTH) levels in a subject, comprising:

administering a therapeutically effective amount of a calcium modulator peptide to a subject in need thereof, whereby serum PTH is reduced;

wherein the calcium modulator peptide comprises:

a) a first polycationic peptide comprising at least 3 amino acids which are positively charged at physiological pH, a first amino terminus, a first carboxy terminus, and a first thiol-containing residue; wherein the first polycationic peptide is chemically modified at the first amino terminus, the first carboxy terminus, or both; and b) a second polycationic peptide comprising at least 3 amino acids which are positively charged at physiological pH, a second amino terminus, a second carboxy terminus, and a second thiol-containing residue; wherein the second polycationic peptide is chemically modified at the second amino terminus, the second carboxy terminus, or both;

wherein the calcium modulator peptide comprises 6 to 30 amino acids which are positively charged at physiological pH.

7. The method of embodiment 6, wherein the therapeutically effective amount of the calcium modulator peptide is sufficient to reduce serum PTH by at least 20% for at least 10 hours post-administration of the calcium modulator peptide.

8. The method of embodiment 6, wherein the therapeutically effective amount of the calcium modulator peptide is sufficient to reduce serum PTH by 30% to 70% for at least 48 hours post-administration of the calcium modulator peptide.

9. The method of embodiment 6, wherein the subject is afflicted with primary hyperparathyroidism, secondary hyperparathyroidism, tertiary hyperparathyroidism, hypercalcemia of malignancy, metastatic bone disease, Paget's disease, osteoarthritis, rheumatoid arthritis, osteomalacia, chondrocalcinosis, achondroplasia, osteochondritis, osteogenesis imperfecta, congenital hypophosphatasia, fibromatous lesions, fibrous dysplasia, multiple myeloma, osteolytic bone disease, periprosthetic osteolysis, periodontal disease, osteoporosis, abnormal bone turnover, or high turnover bone disease.

10. The method of embodiment 9, wherein the subject is afflicted with secondary hyperparathyroidism.

11. A method for decreasing parathyroid hormone (PTH) levels in a subject, comprising:
    administering a therapeutically effective amount of a calcium modulator peptide to a subject in need thereof, whereby serum PTH is reduced;
    wherein the calcium modulator peptide comprises:
    a polycationic peptide comprising 5 to 20 amino acids which are positively charged at physiological pH, an amino terminus, a carboxy terminus, and a first thiol-containing residue;
    wherein the polycationic peptide is chemically modified at the amino terminus, the carboxy terminus, or both; and
    wherein the first thiol-containing residue contains a thiol group which may be present as a free thiol or in a protected form.

12. The method of embodiment 11, wherein the therapeutically effective amount of the calcium modulator peptide is sufficient to reduce serum PTH by at least 20% for at least 10 hours post-administration of the calcium modulator peptide.

13. The method of embodiment 11, wherein the therapeutically effective amount of the calcium modulator peptide is sufficient to reduce serum PTH by 30% to 70% for at least 48 hours post-administration of the calcium modulator peptide.

14. The method of embodiment 11, wherein the subject is afflicted with primary hyperparathyroidism, secondary hyperparathyroidism, tertiary hyperparathyroidism, hypercalcemia of malignancy, metastatic bone disease, Paget's disease, osteoarthritis, rheumatoid arthritis, osteomalacia, chondrocalcinosis, achondroplasia, osteochondritis, osteogenesis imperfecta, congenital hypophosphatasia, fibromatous lesions, fibrous dysplasia, multiple myeloma, osteolytic bone disease, periprosthetic osteolysis, periodontal disease, osteoporosis, abnormal bone turnover, or high turnover bone disease.

15. The method of embodiment 14, wherein the subject is afflicted with secondary hyperparathyroidism.

16. A method for treating hypercalcemia, comprising:
    administering a therapeutically effective amount of a calcium modulator peptide to a subject in need thereof, whereby serum calcium is reduced;
    wherein the calcium modulator peptide comprises:
    a) a polycationic peptide comprising 5 to 20 amino acids which are positively charged at physiological pH, an amino terminus, a carboxy terminus, and a first thiol-containing residue;
    wherein the polycationic peptide is chemically modified at the amino terminus, the carboxy terminus, or both; and
    b) a cargo peptide comprising a second thiol-containing residue;
    wherein the second thiol-containing residue is disulfide bonded to the first thiol-containing residue.

17. The method of embodiment 16, wherein the therapeutically effective amount of the calcium modulator peptide is sufficient to reduce serum calcium by at least 5% for at least 10 hours post-administration of the calcium modulator peptide.

18. The method of embodiment 16, wherein the therapeutically effective amount of the calcium modulator peptide is sufficient to reduce serum calcium by 5% to 20% for at least 48 hours post-administration of the calcium modulator peptide.

19. A method for treating hypercalcemia, comprising:
    administering a therapeutically effective amount of a calcium modulator peptide to a subject in need thereof, whereby serum calcium is reduced;
    wherein the calcium modulator peptide comprises:
    a) a first polycationic peptide comprising at least 3 amino acids which are positively charged at physiological pH, a first amino terminus, a first carboxy terminus, and a first thiol-containing residue; wherein the first polycationic peptide is chemically modified at the first amino terminus, the first carboxy terminus, or both; and
    b) a second polycationic peptide comprising at least 3 amino acids which are positively charged at physiological pH, a second amino terminus, a second carboxy terminus, and a second thiol-containing residue; wherein the second polycationic peptide is chemically modified at the second amino terminus, the second carboxy terminus, or both;
    wherein the calcium modulator peptide comprises 6 to 16 amino acids which are positively charged at physiological pH.

20. The method of embodiment 19, wherein the therapeutically effective amount of the calcium modulator peptide is sufficient to reduce serum calcium by at least 5% for at least 10 hours post-administration of the calcium modulator peptide.

21. The method of embodiment 19, wherein the therapeutically effective amount of the calcium modulator peptide is sufficient to reduce serum calcium by 5% to 20% for at least 48 hours post-administration of the calcium modulator peptide.

22. A method for treating hypercalcemia, comprising:
    administering a therapeutically effective amount of a calcium modulator peptide to a subject in need thereof, whereby serum calcium is reduced;
    wherein the calcium modulator peptide comprises:
    a polycationic peptide comprising 5 to 20 amino acids which are positively charged at physiological pH, an amino terminus, a carboxy terminus, and a first thiol-containing residue;
    wherein the polycationic peptide is chemically modified at the amino terminus, the carboxy terminus, or both; and
    wherein the first thiol-containing residue contains a thiol group which may be present as a free thiol or in a protected form.

23. The method of embodiment 22, wherein the therapeutically effective amount of the calcium modulator peptide is sufficient to reduce serum calcium by at least 5% for at least 10 hours post-administration of the calcium modulator peptide.

24. The method of embodiment 22, wherein the therapeutically effective amount of the calcium modulator peptide is sufficient to reduce serum calcium by 5% to 20% for at least 48 hours post-administration of the calcium modulator peptide.

25. A calcium modulator peptide comprising:
a) a polycationic peptide comprising 5 to 20 amino acids which are positively charged at physiological pH, an amino terminus, a carboxy terminus, and a first thiol-containing residue;
wherein the polycationic peptide is chemically modified at the amino terminus, the carboxy terminus, or both; and
b) a cargo peptide comprising a second thiol-containing residue;
wherein the second thiol-containing residue is disulfide bonded to the first thiol-containing residue.

26. The calcium modulator peptide of embodiment 25, wherein the positively charged amino acids are independently selected from the group consisting of arginine, lysine, histidine, 2,3-diaminopropionic acid (Dap), 2,4-diaminobutyric acid (Dab), ornithine, and homoarginine.

27. The calcium modulator peptide of embodiment 25, wherein the first thiol-containing residue is located at the amino terminus or the carboxy terminus of the polycationic peptide.

28. The calcium modulator peptide of embodiment 25, wherein the first thiol-containing residue is located at a position other than the amino terminus or the carboxy terminus of the polycationic peptide.

29. The calcium modulator peptide of embodiment 25, wherein the second thiol-containing residue is located at the amino terminus or the carboxy terminus of the cargo peptide.

30. The calcium modulator peptide of embodiment 25, wherein the second thiol-containing residue is located at a position other than the amino terminus or the carboxy terminus of the cargo peptide.

31. The calcium modulator peptide of embodiment 25, wherein the amino terminus of the polycationic peptide is chemically modified as an acetamide.

32. The calcium modulator peptide of embodiment 25, wherein the carboxy terminus of the polycationic peptide is chemically modified as a primary carboxamide.

33. The calcium modulator peptide of embodiment 25, wherein the polycationic peptide comprises the sequence of SEQ ID NO:5, SEQ ID NO: 21, SEQ ID NO: 22, SEQ ID NO: 23, SEQ ID NO: 24, SEQ ID NO: 25, SEQ ID NO: 26, or SEQ ID NO: 32.

34. The calcium modulator peptide of embodiment 25 having the sequence of SEQ ID NO:7, SEQ ID NO: 9, SEQ ID NO: 10, or SEQ ID NO:12.

35. The calcium modulator peptide of embodiment 25, wherein the amino terminus of the polycationic peptide is chemically modified as an acetamide and the carboxy terminus of the polycationic peptide is chemically modified as a primary carboxamide.

36. The calcium modulator peptide of embodiment 25, wherein each of the first thiol-containing residue and the second thiol-containing residue is independently selected from the group consisting of cysteine, homocysteine and mercaptopropionic acid.

37. The calcium modulator peptide of embodiment 25 which is conjugated to polyethylene glycol (PEG).

38. A pharmaceutical composition comprising the calcium modulator peptide of embodiment 25 and at least one pharmaceutically acceptable excipient.

39. A calcium modulator peptide comprising:
a) a first polycationic peptide comprising at least 3 amino acids which are positively charged at physiological pH, a first amino terminus, a first carboxy terminus, and a first thiol-containing residue; wherein the first polycationic peptide is chemically modified at the first amino terminus, the first carboxy terminus, or both; and
b) a second polycationic peptide comprising at least 3 amino acids which are positively charged at physiological pH, a second amino terminus, a second carboxy terminus, and a second thiol-containing residue; wherein the second polycationic peptide is chemically modified at the second amino terminus, the second carboxy terminus, or both;
wherein the calcium modulator peptide comprises 6 to 16 amino acids which are positively charged at physiological pH.

40. The calcium modulator peptide of embodiment 39, wherein the positively charged amino acids are independently selected from the group consisting of histidine, lysine, arginine, 2,3-diaminopropionic acid (Dap), 2,4-diaminobutyric acid (Dab), ornithine, and homoarginine.

41. The calcium modulator peptide of embodiment 39, wherein the first thiol-containing residue is located at the first amino terminus or the first carboxy terminus of the first polycationic peptide.

42. The calcium modulator peptide of embodiment 39, wherein the first thiol-containing residue is located at a position other than the first amino terminus or the first carboxy terminus of the first polycationic peptide.

43. The calcium modulator peptide of embodiment 39, wherein the second thiol-containing residue is located at the second amino terminus or the second carboxy terminus of the second polycationic peptide.

44. The calcium modulator peptide of embodiment 39, wherein the second thiol-containing residue is located at a position other than the second amino terminus or the second carboxy terminus of the second polycationic peptide.

45. The calcium modulator peptide of embodiment 39, wherein each of the first polycationic peptide and the second polycationic peptide independently comprises the sequence having SEQ ID NO: 4, SEQ ID NO:5, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 28, SEQ ID NO: 29, SEQ ID NO: 31, SEQ ID NO: 32, SEQ ID NO: 33 or SEQ ID NO: 34.

46. The calcium modulator peptide of embodiment 39, wherein the first polycationic peptide and the second polycationic peptide are the same.

47. The calcium modulator peptide of embodiment 39, wherein the first polycationic peptide and the second polycationic peptide are different.

48. The calcium modulator peptide of embodiment 39, wherein the amino terminus of one or both of the first polycationic peptide and the second polycationic peptide is chemically modified as an acetamide.

49. The calcium modulator peptide of embodiment 39, wherein the carboxy terminus of one or both of the first polycationic peptide and the second polycationic peptide is chemically modified as a primary carboxamide.

50. The calcium modulator peptide of embodiment 39, wherein both the first polycationic peptide and the second polycationic peptide are chemically modified at the amino terminus as an acetamide and are chemically modified at the carboxy terminus as a primary carboxamide.

51. The calcium modulator peptide of embodiment 39, wherein the first thiol-containing residue and the second thiol-containing residue are independently selected from the group consisting of cysteine, homocysteine and mercaptopropionic acid.

52. The calcium modulator peptide of embodiment 39, having the amino acid sequence of SEQ ID NO:13, SEQ ID NO:15, SEQ ID NO:16, SEQ ID NO:17, or SEQ ID NO:18.

53. The polycationic peptide of embodiment 39, which is conjugated to polyethylene glycol (PEG).

54. A pharmaceutical composition comprising the polycationic peptide of embodiment 39 and at least one pharmaceutically acceptable excipient.

55. A calcium modulator peptide comprising:
a polycationic peptide comprising 5 to 20 amino acids which are positively charged at physiological pH, an amino terminus, a carboxy terminus, and a first thiol-containing residue;
wherein the polycationic peptide is chemically modified at the amino terminus, the carboxy terminus, or both; and
wherein the first thiol-containing residue contains a thiol group which may be present as a free thiol or in a protected form.

56. The calcium modulator peptide of embodiment 55, wherein the positively charged amino acids are independently selected from the group consisting of histidine, lysine, arginine, 2,3-diaminopropionic acid (Dap), 2,4-diaminobutyric acid (Dab), ornithine, and homoarginine.

57. The calcium modulator peptide of embodiment 55, wherein the first thiol-containing residue is located at the amino terminus or the carboxy terminus of the polycationic peptide.

58. The calcium modulator peptide of embodiment 55, wherein the first thiol-containing residue is located at a position other than the amino terminus or the carboxy terminus of the polycationic peptide.

59. The calcium modulator peptide of embodiment 55, wherein the first thiol-containing residue contains a free thiol group.

60. The calcium modulator peptide of embodiment 55, wherein the first thiol-containing residue contains a thiol group protected as a thioester, thiocarbonate, hemithioacetal, or disulfide derivative.

61. The calcium modulator peptide of embodiment 55, wherein the amino terminus of the polycationic peptide is chemically modified as an acetamide.

62. The calcium modulator peptide of embodiment 55, wherein the carboxy terminus of the polycationic peptide is chemically modified as a primary carboxamide.

63. The calcium modulator peptide of embodiment 55, wherein the amino terminus of the polycationic peptide is chemically modified as an acetamide and the carboxy terminus of the polycationic peptide is chemically modified as a primary carboxamide.

64. The calcium modulator peptide of embodiment 55, wherein the polycationic peptide comprises the sequence of SEQ ID NO: 5, SEQ ID NO: 21, SEQ ID NO: 22, SEQ ID NO: 23, SEQ ID NO: 24, SEQ ID NO: 25, SEQ ID NO: 26 or SEQ ID NO: 32.

65. The calcium modulator peptide of embodiment 55, further comprising a second thiol-containing residue which is disulfide bonded to the first thiol-containing residue.

66. The calcium modulator peptide of embodiment 55, comprising the sequence of SEQ ID NO:14.

67. The calcium modulator peptide of embodiment 55, wherein the first thiol-containing residue and the second thiol-containing residue are independently selected from the group consisting of cysteine, homocysteine and mercaptopropionic acid.

68. The calcium modulator peptide of embodiment 55 which is conjugated to polyethylene glycol (PEG).

69. A pharmaceutical composition comprising the calcium modulator peptide of embodiment 55 and at least one pharmaceutically acceptable excipient.

The invention claimed is:

1. A method for treating hyperparathyroidism in a subject in need thereof, comprising:
    administering a therapeutically effective amount of a calcium modulator to the subject;
    wherein the calcium modulator comprises:
    a) a first peptide consisting of SEQ ID NO:4; and
    b) a second peptide, wherein the second peptide consists of CHDAPIGYD (SEQ ID NO:7) or CPDYHDAGI (SEQ ID NO:9);
    wherein the cysteine residue of the first peptide is disulfide bonded to the cysteine residue of the second peptide.

2. The method of claim 1, wherein the therapeutically effective amount of the calcium modulator is sufficient to reduce serum PTH by at least 20% for at least 10 hours post-administration of the calcium modulator.

3. The method of claim 1, wherein the therapeutically effective amount of the calcium modulator is sufficient to reduce serum PTH by 30% to 70% for at least 48 hours post-administration of the calcium modulator.

4. The method of claim 1, wherein the hyperparathyroidism is secondary hyperparathyroidism.

* * * * *

SEQUENCE LISTING

```
<160> NUMBER OF SEQ ID NOS: 36

<210> SEQ ID NO 1
<211> LENGTH: 8
<212> TYPE: PRT
<213> ORGANISM: Homo sapiens

<400> SEQUENCE: 1

His Asp Ala Pro Ile Gly Tyr Asp
1               5

<210> SEQ ID NO 2
<211> LENGTH: 9
<212> TYPE: PRT
<213> ORGANISM: Artificial
<220> FEATURE:
<223> OTHER INFORMATION: synthetic construct

<400> SEQUENCE: 2

Cys His Asp Ala Pro Ile Gly Tyr Asp
1               5

<210> SEQ ID NO 3
<211> LENGTH: 11
<212> TYPE: PRT
<213> ORGANISM: Human immunodeficiency virus 1
```

```
<400> SEQUENCE: 3

Tyr Gly Arg Lys Lys Arg Arg Gln Arg Arg Arg
1               5                   10

<210> SEQ ID NO 4
<211> LENGTH: 12
<212> TYPE: PRT
<213> ORGANISM: Artificial
<220> FEATURE:
<223> OTHER INFORMATION: synthetic modified Human immunodeficiency
      virus 1

<400> SEQUENCE: 4

Cys Tyr Gly Arg Lys Lys Arg Arg Gln Arg Arg Arg
1               5                   10

<210> SEQ ID NO 5
<211> LENGTH: 12
<212> TYPE: PRT
<213> ORGANISM: Artificial
<220> FEATURE:
<223> OTHER INFORMATION: synthetic construct

<400> SEQUENCE: 5

Cys Tyr Gly Arg Lys Lys Arg Arg Gln Arg Arg Arg
1               5                   10

<210> SEQ ID NO 6
<211> LENGTH: 9
<212> TYPE: PRT
<213> ORGANISM: Artificial
<220> FEATURE:
<223> OTHER INFORMATION: synthetic construct of a PKC peptide linked to
      a TAT derived peptide through a disulfide bond
<220> FEATURE:
<221> NAME/KEY: DISULFID
<222> LOCATION: (1)..(1)
<223> OTHER INFORMATION: linked to the N-terminus of SEQ ID NO:4 through
      a disulfide bond

<400> SEQUENCE: 6

Cys His Asp Ala Pro Ile Gly Tyr Asp
1               5

<210> SEQ ID NO 7
<211> LENGTH: 9
<212> TYPE: PRT
<213> ORGANISM: Artificial
<220> FEATURE:
<223> OTHER INFORMATION: synthetic construct of a PKC peptide linked to
      a TAT derived peptide through a disulfide bond
<220> FEATURE:
<221> NAME/KEY: DISULFID
<222> LOCATION: (1)..(1)
<223> OTHER INFORMATION: linked to the N-terminus of SEQ ID NO:4 through
      a disulfide bond

<400> SEQUENCE: 7

Cys His Asp Ala Pro Ile Gly Tyr Asp
1               5

<210> SEQ ID NO 8
<211> LENGTH: 11
<212> TYPE: PRT
<213> ORGANISM: Artificial
<220> FEATURE:
<223> OTHER INFORMATION: synthetic construct of a PKC peptide linked to
      a TAT derived peptide through a disulfide bond
<220> FEATURE:
```

```
<221> NAME/KEY: DISULFID
<222> LOCATION: (1)..(1)
<223> OTHER INFORMATION: linked to the N-terminus of SEQ ID NO:4 through
      a disulfide bond

<400> SEQUENCE: 8

Cys Ser Phe Asn Ser Tyr Glu Leu Gly Ser Leu
1               5                   10

<210> SEQ ID NO 9
<211> LENGTH: 9
<212> TYPE: PRT
<213> ORGANISM: Artificial
<220> FEATURE:
<223> OTHER INFORMATION: synthetic construct of a PKC peptide linked to
      a TAT derived peptide through a disulfide bond
<220> FEATURE:
<221> NAME/KEY: DISULFID
<222> LOCATION: (1)..(1)
<223> OTHER INFORMATION: linked to the N-terminus of SEQ ID NO:4 through
      a disulfide bond

<400> SEQUENCE: 9

Cys Pro Asp Tyr His Asp Ala Gly Ile
1               5

<210> SEQ ID NO 10
<211> LENGTH: 9
<212> TYPE: PRT
<213> ORGANISM: Artificial
<220> FEATURE:
<223> OTHER INFORMATION: synthetic construct of a PKC peptide linked to
      a TAT derived peptide through a disulfide bond
<220> FEATURE:
<221> NAME/KEY: DISULFID
<222> LOCATION: (1)..(1)
<223> OTHER INFORMATION: linked to the N-terminus of SEQ ID NO:4 through
      a disulfide bond

<400> SEQUENCE: 10

Cys Glu Ala Val Ser Leu Lys Pro Thr
1               5

<210> SEQ ID NO 11
<211> LENGTH: 21
<212> TYPE: PRT
<213> ORGANISM: Artificial
<220> FEATURE:
<223> OTHER INFORMATION: synthetic construct of a PKC peptide linked to
      a TAT derived peptide

<400> SEQUENCE: 11

Glu Ala Val Ser Leu Lys Pro Thr Gly Gly Tyr Gly Arg Lys Lys Arg
1               5                   10                  15

Arg Gln Arg Arg Arg
            20

<210> SEQ ID NO 12
<211> LENGTH: 14
<212> TYPE: PRT
<213> ORGANISM: Artificial
<220> FEATURE:
<223> OTHER INFORMATION: synthetic construct of a PKC peptide linked to
      a TAT derived peptide through a disulfide bond
<220> FEATURE:
<221> NAME/KEY: DISULFID
<222> LOCATION: (1)..(1)
<223> OTHER INFORMATION: linked to the N-terminus of SEQ ID NO:35
      through a disulfide bond
```

```
<400> SEQUENCE: 12

Cys Arg Phe Ala Arg Lys Gly Ala Leu Arg Gln Lys Asn Val
1               5                   10

<210> SEQ ID NO 13
<211> LENGTH: 12
<212> TYPE: PRT
<213> ORGANISM: Artificial
<220> FEATURE:
<223> OTHER INFORMATION: synthetic construct of a PKC peptide linked to
      a TAT derived peptide through a disulfide bond
<220> FEATURE:
<221> NAME/KEY: DISULFID
<222> LOCATION: (1)..(1)
<223> OTHER INFORMATION: linked to the N-terminus of SEQ ID NO:4 through
      a disulfide bond

<400> SEQUENCE: 13

Cys Tyr Gly Arg Lys Lys Arg Arg Gln Arg Arg Arg
1               5                   10

<210> SEQ ID NO 14
<211> LENGTH: 13
<212> TYPE: PRT
<213> ORGANISM: Artificial
<220> FEATURE:
<223> OTHER INFORMATION: synthetic construct

<400> SEQUENCE: 14

Cys Tyr Gly Arg Lys Lys Arg Arg Gln Arg Arg Arg Cys
1               5                   10

<210> SEQ ID NO 15
<211> LENGTH: 4
<212> TYPE: PRT
<213> ORGANISM: Artificial
<220> FEATURE:
<223> OTHER INFORMATION: synthetic construct of a polycationic peptide
      linked to a TAT derived peptide through a disulfide bond
<220> FEATURE:
<221> NAME/KEY: DISULFID
<222> LOCATION: (1)..(1)
<223> OTHER INFORMATION: linked to the N-terminus of SEQ ID NO:36
      through a disulfide bond

<400> SEQUENCE: 15

Cys Arg Arg Arg
1

<210> SEQ ID NO 16
<211> LENGTH: 7
<212> TYPE: PRT
<213> ORGANISM: Artificial
<220> FEATURE:
<223> OTHER INFORMATION: synthetic construct of a TAT derived peptide
      linked to a TAT derived peptide through a disulfide bond
<220> FEATURE:
<221> NAME/KEY: DISULFID
<222> LOCATION: (1)..(1)
<223> OTHER INFORMATION: linked to the N-terminus of SEQ ID NO:36
      through a disulfide bond

<400> SEQUENCE: 16

Cys Tyr Gly Arg Lys Lys Arg
1               5

<210> SEQ ID NO 17
<211> LENGTH: 8
<212> TYPE: PRT
```

```
<213> ORGANISM: Artificial
<220> FEATURE:
<223> OTHER INFORMATION: synthetic construct of a polycationic peptide
      linked to a polycationic peptide through a disulfide bond
<220> FEATURE:
<221> NAME/KEY: DISULFID
<222> LOCATION: (1)..(1)
<223> OTHER INFORMATION: linked to the N-terminus of SEQ ID NO:19
      through a disulfide bond

<400> SEQUENCE: 17

Cys Arg Arg Arg Cys Arg Arg Arg
1               5

<210> SEQ ID NO 18
<211> LENGTH: 5
<212> TYPE: PRT
<213> ORGANISM: Artificial
<220> FEATURE:
<223> OTHER INFORMATION: synthetic construct of a polycationic peptide
      linked to a polycationic peptide through a disulfide bond
<220> FEATURE:
<221> NAME/KEY: DISULFID
<222> LOCATION: (1)..(1)
<223> OTHER INFORMATION: linked to the N-terminus of SEQ ID NO:20
      through a disulfide bond

<400> SEQUENCE: 18

Cys Arg Arg Arg Arg
1               5

<210> SEQ ID NO 19
<211> LENGTH: 4
<212> TYPE: PRT
<213> ORGANISM: Artificial
<220> FEATURE:
<223> OTHER INFORMATION: synthetic construct

<400> SEQUENCE: 19

Cys Arg Arg Arg
1

<210> SEQ ID NO 20
<211> LENGTH: 5
<212> TYPE: PRT
<213> ORGANISM: Artificial
<220> FEATURE:
<223> OTHER INFORMATION: synthetic construct

<400> SEQUENCE: 20

Cys Arg Arg Arg Arg
1               5

<210> SEQ ID NO 21
<211> LENGTH: 8
<212> TYPE: PRT
<213> ORGANISM: Artificial
<220> FEATURE:
<223> OTHER INFORMATION: synthetic construct

<400> SEQUENCE: 21

Cys Arg Arg Arg Arg Arg Arg Arg
1               5

<210> SEQ ID NO 22
<211> LENGTH: 9
<212> TYPE: PRT
<213> ORGANISM: Artificial
<220> FEATURE:
```

```
<223> OTHER INFORMATION: synthetic construct

<400> SEQUENCE: 22

Cys Arg Arg Arg Arg Arg Arg Arg
1               5

<210> SEQ ID NO 23
<211> LENGTH: 10
<212> TYPE: PRT
<213> ORGANISM: Artificial
<220> FEATURE:
<223> OTHER INFORMATION: synthetic construct

<400> SEQUENCE: 23

Cys Arg Arg Arg Arg Arg Arg Arg Arg Arg
1               5                   10

<210> SEQ ID NO 24
<211> LENGTH: 11
<212> TYPE: PRT
<213> ORGANISM: Artificial
<220> FEATURE:
<223> OTHER INFORMATION: synthetic construct

<400> SEQUENCE: 24

Cys Arg Arg Arg Arg Arg Arg Arg Arg Arg Arg
1               5                   10

<210> SEQ ID NO 25
<211> LENGTH: 12
<212> TYPE: PRT
<213> ORGANISM: Artificial
<220> FEATURE:
<223> OTHER INFORMATION: synthetic construct

<400> SEQUENCE: 25

Cys Arg Arg Arg Arg Arg Arg Arg Arg Arg Arg Arg
1               5                   10

<210> SEQ ID NO 26
<211> LENGTH: 13
<212> TYPE: PRT
<213> ORGANISM: Artificial
<220> FEATURE:
<223> OTHER INFORMATION: synthetic construct

<400> SEQUENCE: 26

Cys Arg Arg Arg Arg Arg Arg Arg Arg Arg Arg Arg Arg
1               5                   10

<210> SEQ ID NO 27
<211> LENGTH: 6
<212> TYPE: PRT
<213> ORGANISM: Human immunodeficiency virus 1

<400> SEQUENCE: 27

Tyr Gly Arg Lys Lys Arg
1               5

<210> SEQ ID NO 28
<211> LENGTH: 7
<212> TYPE: PRT
<213> ORGANISM: Artificial
<220> FEATURE:
<223> OTHER INFORMATION: synthetic modified Human immunodeficiency
      virus 1
```

```
<400> SEQUENCE: 28

Cys Tyr Gly Arg Lys Lys Arg
1               5

<210> SEQ ID NO 29
<211> LENGTH: 7
<212> TYPE: PRT
<213> ORGANISM: Artificial
<220> FEATURE:
<223> OTHER INFORMATION: synthetic modified Human immunodeficiency
      virus 1

<400> SEQUENCE: 29

Cys Tyr Gly Arg Lys Lys Arg
1               5

<210> SEQ ID NO 30
<211> LENGTH: 11
<212> TYPE: PRT
<213> ORGANISM: Artificial
<220> FEATURE:
<223> OTHER INFORMATION: synthetic construct

<400> SEQUENCE: 30

Tyr Gly Arg Arg Ala Arg Arg Arg Ala Arg Arg
1               5                   10

<210> SEQ ID NO 31
<211> LENGTH: 12
<212> TYPE: PRT
<213> ORGANISM: Artificial
<220> FEATURE:
<223> OTHER INFORMATION: synthetic construct

<400> SEQUENCE: 31

Cys Tyr Gly Arg Arg Ala Arg Arg Arg Ala Arg Arg
1               5                   10

<210> SEQ ID NO 32
<211> LENGTH: 12
<212> TYPE: PRT
<213> ORGANISM: Artificial
<220> FEATURE:
<223> OTHER INFORMATION: synthetic construct

<400> SEQUENCE: 32

Cys Tyr Gly Arg Arg Ala Arg Arg Arg Ala Arg Arg
1               5                   10

<210> SEQ ID NO 33
<211> LENGTH: 4
<212> TYPE: PRT
<213> ORGANISM: Artificial
<220> FEATURE:
<223> OTHER INFORMATION: synthetic construct

<400> SEQUENCE: 33

Cys Arg Arg Arg
1

<210> SEQ ID NO 34
<211> LENGTH: 5
<212> TYPE: PRT
<213> ORGANISM: Artificial
<220> FEATURE:
<223> OTHER INFORMATION: synthetic construct
```

```
<400> SEQUENCE: 34

Cys Arg Arg Arg Arg
1               5

<210> SEQ ID NO 35
<211> LENGTH: 12
<212> TYPE: PRT
<213> ORGANISM: Artificial
<220> FEATURE:
<223> OTHER INFORMATION: synthetic construct

<400> SEQUENCE: 35

Cys Tyr Gly Arg Arg Ala Arg Arg Arg Ala Arg Arg
1               5                   10

<210> SEQ ID NO 36
<211> LENGTH: 7
<212> TYPE: PRT
<213> ORGANISM: Artificial
<220> FEATURE:
<223> OTHER INFORMATION: synthetic construct

<400> SEQUENCE: 36

Cys Tyr Gly Arg Lys Lys Arg
1               5
```